United States Patent
Yang et al.

(10) Patent No.: US 10,927,358 B2
(45) Date of Patent: Feb. 23, 2021

(54) ENDOGLUCANASE COMPOSITIONS AND METHODS

(71) Applicant: Fornia BioSolutions, Inc., Hayward, CA (US)

(72) Inventors: Jie Yang, Foster City, CA (US); Khin Oo, Daly City, CA (US); Goutami Banerjee, Hayward, CA (US); Xiyun Zhang, San Ramon, CA (US); Wenhua Lu, Dublin, CA (US); Stephen Joshua Macaso Millet, Tracy, CA (US); Tatsuya Fukushima, Fremont, CA (US); Eric Lin Hu, Millbrae, CA (US); Imad N. Sawaya, Redwood City, CA (US); Marielle De Jesus Palatino, Stockton, CA (US)

(73) Assignee: Fornia BioSolutions, Inc., Hayward, CA (US)

( * ) Notice: Subject to any disclaimer, the term of this patent is extended or adjusted under 35 U.S.C. 154(b) by 0 days.

(21) Appl. No.: 16/744,016

(22) Filed: Jan. 15, 2020

(65) Prior Publication Data
US 2020/0231955 A1 Jul. 23, 2020

Related U.S. Application Data

(60) Provisional application No. 62/793,065, filed on Jan. 16, 2019.

(51) Int. Cl.
*C12N 9/00* (2006.01)
*C12N 9/42* (2006.01)

(52) U.S. Cl.
CPC .... *C12N 9/2437* (2013.01); *C12Y 302/01004* (2013.01)

(58) Field of Classification Search
CPC .............................. C12N 9/2434; C12N 9/244
USPC ......................................................... 435/209
See application file for complete search history.

(56) References Cited

U.S. PATENT DOCUMENTS

| | | |
|---|---|---|
| 3,664,961 A | 5/1972 | Norris |
| 5,443,750 A | 8/1995 | Convents et al. |
| 5,948,672 A | 9/1999 | Rasmussen et al. |
| 5,958,082 A | 9/1999 | Lund et al. |
| 6,001,639 A | 12/1999 | Schulein et al. |
| 7,256,032 B2 | 8/2007 | Valtakari et al. |
| 8,198,068 B2 * | 6/2012 | Wu ................... D06B 11/0096 435/225 |
| 10,294,484 B2 * | 5/2019 | Brevnova ................. C12P 7/06 |
| 2013/0323822 A1 * | 12/2013 | Brevnova ............ C12N 9/2482 435/254.21 |

FOREIGN PATENT DOCUMENTS

| | | |
|---|---|---|
| EP | 0238216 A1 | 9/1987 |
| WO | WO 1994/07998 A1 | 4/1994 |
| WO | WO 2004/053039 | 6/2004 |
| WO | WO 2010/120557 A1 | 10/2010 |
| WO | WO 2013/096244 A1 | 6/2013 |
| WO | WO 2013/164340 A1 | 11/2013 |
| WO | WO 2016/106432 A2 | 6/2016 |
| WO | WO 2017/106676 A1 | 6/2017 |

OTHER PUBLICATIONS

Annex to Form PCT/ISA/206, Communication Relating to the Results of the Partial International Search for International application No. PCT/US2020/013734, dated Apr. 21, 2020, 11 pages.
Kusuya et al., "Aspergillus udagawae strain IFM 46973T", Nov. 11, 2011, Database UniProt , XP55683765, retrieved from EBI accession No. A0A0K8LETO_9EURO, Database accession No. A0A0K8LETO sequence.
Agrawal et al., "Bio-Stoning of Demin—an Environmental-Friendly Approach", Current Trends in Biomedical Engineering & Biosciences. 2017. 3(3):1-3.
International Search Report and Written Opinion for International Application No. PCT/US2020/013734, dated Aug. 5, 2020, 19 pages.

\* cited by examiner

*Primary Examiner* — Tekchand Saidha
(74) *Attorney, Agent, or Firm* — Morgan, Lewis & Bockius LLP

(57) ABSTRACT

The invention is directed to novel variant endoglucanases.

18 Claims, 24 Drawing Sheets

Specification includes a Sequence Listing.

FIGURE 2

SP (Signal Peptide): AA 1-16 (*Bold and Italicized*)
CD (Catalytic Domain; GH12): AA 30-234

```
       1                                                  50
EG140  MKTFAIFGAL FSSALAQTLC NQYGTYSNGR YTVNNNLWGQ GSGSGSQCTY
EG185  MKTFAILGAL FSCALAQTLC DQYATYSNGR YTVNNNLWGK SSGSGSQCTY 51                                                 100
EG140  VDSISNSGVA WHTTWTWSGG DNQVKSYANS QVALTKKHVS QIGSIPTTVQ
EG185  VDSISNSGVG WHTTWTWSGG DNQVKSYANS QVSLTKKLVS QIGSIPTTVQ 101                                                 150
EG140  WSYDNTNIRA DVAYDLFTAA DINHVTYSGD YELMIWLARY GGVQPIGSRI
EG185  WSYDNTNTRA DVAYDLFTAA DINHVTYSGD YELMIWLARY GSVQPIGSQI 151                                                 200
EG140  GTANIAGHTW ELWYGGSTQK TYSFVSATPI TSFSGDVMDF WRYLTNNHGY
EG185  DTASIGGHTW QLWYGGSTQK TYSFVSATPI TSFSGDVMDF WDYLTSRHGY 201              234
EG140  PASSQYLINM QFGTEPFTGG RATMKVSKFT ASVN
EG185  PASSQYLINM QFGTEPFTGG PATLRVSQWT ASVN
```

FIGURE 3A

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG140 G1P (CL00078795) | Alias |
|---|---|---|---|---|---|---|
| CL00088147 | 1.03 | 0.04 | 1.24 | 0.16 | G25D/A161G/M172K/H182Q/M194L/K212N | |
| CL00088163 | 1.10 | 0.08 | 1.33 | 0.10 | N12S/G25D/Q65G/S160A/A161G/V171I/Y184F/M194L/K212N | |
| CL00088174 | 0.85 | 0.09 | 1.10 | 0.03 | G25D/N138T/V171I/W175F/H182Q/Y184F | |
| CL00088217 | 0.99 | 0.01 | 1.19 | 0.06 | G25D/N138T/I139V/M194L | |
| CL00088245 | 1.04 | 0.04 | 1.17 | 0.04 | H182Q/K212N | |
| CL00088269 | 1.00 | 0.02 | 1.01 | 0.02 | G25D/A161G/T214S | |
| CL00088274 | 1.05 | 0.07 | 1.04 | 0.08 | N12S/G25D/A161G/H182Q/Y184F/M194L/K212N/T214S | |
| CL00088284 | 1.12 | 0.00 | 1.24 | 0.10 | G25D/N138T/H182Q/K212N | |
| CL00088347 | 1.08 | 0.01 | 1.06 | 0.12 | N12S/G25D/A44S/I139V | |
| CL00088382 | 1.12 | 0.07 | 1.23 | 0.18 | G25D/N138T/K212N | |
| CL00088384 | 0.98 | 0.03 | 1.26 | 0.06 | G25D/V171I/W175F/M194L/K212N | |
| CL00088394 | 1.14 | 0.04 | 1.30 | 0.11 | G25D/A161G/K212N | |
| CL00088403 | 1.02 | 0.04 | 1.05 | 0.01 | V171I/Y184F | |
| CL00088404 | 1.08 | 0.04 | 1.16 | 0.06 | G25D/A44S/A161G | |
| CL00088420 | 1.04 | 0.03 | 1.20 | 0.09 | G25D/M172K/H182Q | |
| CL00088425 | 1.19 | 0.04 | 1.36 | 0.09 | G25D/A44S/V171I/M172K/H182Q/K212N | G1V1 |
| CL00088436 | 1.11 | 0.00 | 1.18 | 0.05 | G25D/V171I/M172K/H182Q/M194L | |
| CL00088453 | 1.02 | 0.02 | 1.15 | 0.02 | H182Q/M194L | |
| CL00088465 | 1.02 | 0.03 | 1.33 | 0.14 | G25D/K212N | G1V2 |
| CL00088472 | 1.05 | 0.01 | 1.20 | 0.03 | N12S/G25D/N138T/A161G/K212N | |

Figure 3B

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG140 G1P (CL00078795) | Alias |
|---|---|---|---|---|---|---|
| CL00088499 | 1.20 | 0.04 | 1.32 | 0.02 | G25D/H182Q/Y184F/M194L/K212N | |
| CL00088540 | 1.19 | 0.02 | 1.23 | 0.04 | N12S/G25D/N40S/I139V/V171I/M172K/H182Q/Y184F/M194L/K212N/T214S | |
| CL00088551 | 0.98 | 0.03 | 1.18 | 0.08 | K212N | |
| CL00088553 | 1.08 | 0.09 | 1.36 | 0.06 | N12S/G25D/H182Q/K212N | G1V3 |
| CL00088586 | 1.00 | 0.04 | 1.17 | 0.04 | G25D/N40S/A44S/N138T/A161G/V171I/W175F/Y184F/M194L/K212N | |
| CL00088589 | 0.95 | 0.04 | 1.01 | 0.05 | N12S/N40S/Y184F/T214S | |
| CL00088614 | 1.09 | 0.04 | 1.13 | 0.16 | N12S/G25D/A44S/Q65G | |
| CL00088621 | 1.03 | 0.03 | 1.13 | 0.04 | G25D/A161G/M194L/T214S | |
| CL00088786 | 1.10 | 0.01 | 1.19 | 0.06 | A44S/N138T/I139V/V171I/H182Q/Y184F/M194L/K212N | |
| CL00088830 | 1.20 | 0.05 | 1.33 | 0.03 | G25D/Y184F/M194L/K212N | |
| CL00088957 | 1.08 | 0.04 | 1.09 | 0.09 | I139V | |
| CL00098537 | 0.88 | 0.04 | 1.15 | 0.09 | N12S/G13P/D55P/M172K/R205P/K212N | |
| CL00098621 | 1.05 | 0.04 | 1.19 | 0.18 | N12S/G25D/D55P/V171I/M172K/S187P | |
| CL00098643 | 1.09 | 0.06 | 1.26 | 0.20 | G25D/S187P | |
| CL00098656 | 1.20 | 0.05 | 1.40 | 0.15 | G13P/G25D/D55P/A161P/S187P/R205P/K212N | |
| CL00098688 | 1.16 | 0.02 | 1.47 | 0.10 | G25D/D55P | |
| CL00098767 | 1.01 | 0.07 | 1.16 | 0.17 | N12S/R133P/A161P/V171I/S187P/K212N | |
| CL00098774 | 1.12 | 0.04 | 1.32 | 0.14 | N12S/G25D | |
| CL00098778 | 1.01 | 0.03 | 1.28 | 0.08 | G13P/G25D/D55P/V171I/S187P/R205P | |

Figure 3C

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG140 G1P (CL00078795) | Alias |
|---|---|---|---|---|---|---|
| CL00098790 | 1.11 | 0.04 | 1.42 | 0.08 | G13P/G25D/V171I/M172K/S187P/R205P/K212N | |
| CL00098799 | 1.08 | 0.04 | 1.35 | 0.10 | G25D/D55P/R205P | G1V4 (G2P) |
| CL00098969 | 0.95 | 0.05 | 1.17 | 0.19 | G25D/V171I/M172K | |
| CL00099092 | 1.07 | 0.03 | 1.18 | 0.04 | G25D/R133P | |
| CL00099164 | 1.05 | 0.07 | 1.12 | 0.03 | N12S/G25D/V171I/M172K | |
| CL00099182 | 1.04 | 0.04 | 1.18 | 0.03 | N12S/G25D/H182Q/R205P | |
| CL00099241 | 1.16 | 0.06 | 1.34 | 0.03 | N12S/G25D/A161P/S187P/K212N | |
| CL00099247 | 1.02 | 0.04 | 1.27 | 0.15 | G25D/D55P/V171I/M172K/R205P | |
| CL00099270 | 1.02 | 0.02 | 1.12 | 0.05 | D55P/R205P | |
| CL00099318 | 1.02 | 0.03 | 1.15 | 0.10 | N12S/R205P | |
| CL00099337 | 0.99 | 0.06 | 1.20 | 0.13 | N12S/G25D/T69P/R133P/V171I/M172K/R205P/K212N | |
| CL00105062 | 1.19 | 0.17 | 1.46 | 0.12 | S166N | |
| CL00105075 | 1.18 | 0.09 | 1.51 | 0.07 | G25S | |
| CL00105084 | 1.30 | 0.02 | 1.50 | 0.10 | S166V | |
| CL00105086 | 1.39 | 0.06 | 1.41 | 0.06 | S211F | |
| CL00105098 | 1.11 | 0.04 | 1.16 | 0.04 | S166I | |
| CL00105277 | 1.03 | 0.03 | 1.11 | 0.08 | T50R | |
| CL00105757 | 0.93 | 0.09 | 1.28 | 0.05 | T179L | |
| CL00105759 | 1.09 | 0.07 | 1.46 | 0.08 | T179Y/R205Y | |

Figure 3D

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG140 G1P (CL00078795) | Alias |
|---|---|---|---|---|---|---|
| CL00105783 | 1.11 | 0.08 | 1.27 | 0.13 | N181S | |
| CL00105795 | 1.31 | 0.05 | 1.42 | 0.11 | R205P | |
| CL00106014 | 1.13 | 0.05 | 1.45 | 0.11 | T69D | |
| CL00107553 | 1.31 | 0.10 | 1.46 | 0.15 | N12E | |
| CL00107614 | 1.15 | 0.02 | 1.27 | 0.02 | R14S | |
| CL00107743 | 1.01 | 0.03 | 1.14 | 0.04 | H182E | |
| CL00107845 | 1.07 | 0.06 | 1.17 | 0.08 | R176H | |
| CL00107990 | 1.17 | 0.06 | 1.22 | 0.15 | N12G | |
| CL00108046 | 1.14 | 0.03 | 1.16 | 0.08 | N12D | |
| CL00108054 | 1.37 | 0.11 | 1.57 | 0.19 | R176Q | |
| CL00108133 | 1.16 | 0.01 | 1.40 | 0.07 | T165Y | |
| CL00108201 | 1.05 | 0.03 | 1.12 | 0.07 | D88H | |
| CL00108273 | 1.09 | 0.04 | 1.13 | 0.06 | A161R | |
| CL00108444 | 1.05 | 0.04 | 1.13 | 0.05 | N12T | |
| CL00108503 | 1.03 | 0.05 | 1.12 | 0.19 | V217Q | |
| CL00108577 | 1.05 | 0.06 | 1.37 | 0.19 | T48N | |
| CL00108589 | 1.18 | 0.04 | 1.34 | 0.04 | D88N | |
| CL00108629 | 1.00 | 0.04 | 1.29 | 0.10 | R176L | |
| CL00108633 | 1.16 | 0.05 | 1.27 | 0.04 | T165D | |
| CL00108670 | 1.14 | 0.08 | 1.31 | 0.14 | K71S | |

Figure 3E

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG140 G1P (CL00078795) | Alias |
|---|---|---|---|---|---|---|
| CL00108692 | 0.97 | 0.05 | 1.24 | 0.09 | T165R | |
| CL00108795 | 1.30 | 0.04 | 1.39 | 0.10 | H182T | |
| CL00108915 | 1.20 | 0.04 | 1.33 | 0.11 | G126S | |
| CL00108944 | 1.30 | 0.00 | 1.49 | 0.03 | G126K | |
| CL00108961 | 1.12 | 0.03 | 1.21 | 0.05 | A104D | |
| CL00108990 | 1.09 | 0.02 | 1.14 | 0.05 | D173P | |
| CL00109131 | 1.45 | 0.02 | 1.74 | 0.02 | G126T | |
| CL00109167 | 1.22 | 0.06 | 1.44 | 0.10 | G126R | |
| CL00109311 | 1.09 | 0.03 | 1.24 | 0.08 | A44D | |
| CL00109380 | 1.03 | 0.07 | 1.13 | 0.02 | D173E | |
| CL00109404 | 1.07 | 0.03 | 1.15 | 0.01 | D173L | |
| CL00109472 | 1.25 | 0.02 | 1.38 | 0.01 | G126V | |
| CL00109480 | 1.11 | 0.11 | 1.27 | 0.09 | G126A | |
| CL00109552 | 1.18 | 0.04 | 1.28 | 0.05 | G126P | |
| CL00109670 | 1.20 | 0.03 | 1.29 | 0.03 | G126N | |
| CL00109740 | 1.27 | 0.03 | 1.34 | 0.10 | G126I | |
| CL00109802 | 1.07 | 0.05 | 1.12 | 0.07 | T152N | |
| CL00110649 | 1.10 | 0.05 | 1.28 | 0.10 | Q128R | |
| CL00110672 | 1.01 | 0.05 | 1.17 | 0.03 | Q128F | |

Figure 3F

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG140 G1P (CL00078795) | Alias |
| --- | --- | --- | --- | --- | --- | --- |
| CL00110768 | 0.97 | 0.03 | 1.10 | 0.03 | N218G | |
| CL00110778 | 1.04 | 0.04 | 1.11 | 0.10 | S86L | |
| CL00110802 | 1.04 | 0.03 | 1.10 | 0.06 | T207E | |
| CL00110817 | 1.08 | 0.09 | 1.13 | 0.04 | G169S | |
| CL00111003 | 0.99 | 0.01 | 1.14 | 0.10 | S86Q | |
| CL00111168 | 0.98 | 0.00 | 1.14 | 0.03 | N218S | |

FIGURE 4A

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG140 G1P (CL00078795) | Alias |
|---|---|---|---|---|---|---|
| CL00111228 | 1.09 | 0.02 | 1.22 | 0.03 | N12E/G25D/D55I/G126V/T136M/T165D/R205P | |
| CL00111246 | 1.18 | 0.04 | 1.39 | 0.06 | N12E/G25D/D55I/G126S/T136Y/R205P/T207E/N218S | |
| CL00111290 | 1.22 | 0.02 | 1.30 | 0.08 | N12E/G25S/D55P/N181S/R205P | |
| CL00111306 | 1.06 | 0.01 | 1.24 | 0.04 | N12E/G25D/D55I/P80G/G126I/T136M/R205P | |
| CL00111333 | 1.12 | 0.04 | 1.42 | 0.04 | N12E/G25D/D55P/G126K/E145A/T165D/R205P | |
| CL00111397 | 1.07 | 0.05 | 1.42 | 0.10 | N12E/G25D/D55I/G126T/T136M/T165Y/T179L/R205P | |
| CL00111472 | 1.12 | 0.02 | 1.33 | 0.03 | N12E/G25S/D55P/P80G/G126T/T136Y/T165Y/R205P/T207E | |
| CL00111476 | 1.19 | 0.03 | 1.41 | 0.03 | N12E/G25S/D55P/G126T/R205P/T207E | |
| CL00111493 | 1.21 | 0.09 | 1.36 | 0.04 | N12E/G25D/D55P/G126N/T136Y/T165Y/T179Y/N181S/R205P/T207E | |
| CL00111499 | 1.15 | 0.06 | 1.38 | 0.10 | N12E/G25S/D55P/P80G/G126R/T136Y/R205P | |
| CL00111500 | 1.19 | 0.05 | 1.46 | 0.04 | G25D/D55P/G126T/T165Y/R205P | |
| CL00111502 | 1.06 | 0.04 | 1.36 | 0.11 | N12E/G25S/D55I/G126K/T165D/R205P | |
| CL00111511 | 1.10 | 0.02 | 1.21 | 0.01 | N12E/G25S/D55P/G126I/T136Y/R205P | |
| CL00111519 | 1.12 | 0.02 | 1.21 | 0.04 | G25D/D55P/G126K/T136Y/T179Y/N181S/R205P | |
| CL00111527 | 1.15 | 0.02 | 1.34 | 0.03 | N12E/G25D/D55I/G126R/R205P | |
| CL00111541 | 1.09 | 0.04 | 1.41 | 0.09 | N12E/G25S/D55P/G126N/R205P/T207E | |
| CL00111545 | 1.09 | 0.01 | 1.16 | 0.04 | N12E/G25D/D55P/P80G/E145A/R205P/T207E | |
| CL00111555 | 1.10 | 0.04 | 1.18 | 0.09 | G25D/D55P/T136Y/T165Y/R205P/T207E | |
| CL00111562 | 1.05 | 0.02 | 1.38 | 0.02 | N12E/G25S/D55P/G126R/T136Y/T165Y/R205P | |
| CL00111564 | 1.05 | 0.01 | 1.18 | 0.08 | N12E/G25D/D55P/P80G/R205P | |

Figure 4B

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG140 G1P (CL00078795) | Alias |
|---|---|---|---|---|---|---|
| CL00111567 | 1.13 | 0.01 | 1.19 | 0.05 | G25D/D55I/G126K/R205Y | |
| CL00111570 | 1.14 | 0.06 | 1.31 | 0.04 | N12E/G25S/D55P/G126R/R205P/T207E | |
| CL00111588 | 1.15 | 0.01 | 1.35 | 0.07 | G25D/D55P/G126T/T136Y/T165Y/R205P/N218S | |
| CL00111593 | 1.18 | 0.05 | 1.28 | 0.02 | N12E/G25D/D55P/G126N/R205P | |
| CL00111598 | 1.09 | 0.02 | 1.36 | 0.08 | N12E/G25D/D55P/G126K/R205P | |
| CL00111607 | 1.12 | 0.01 | 1.21 | 0.05 | N12E/G25D/D55P/T165D/R205Y | |
| CL00111642 | 1.23 | 0.02 | 1.41 | 0.08 | N12E/G25D/D55I/P80G/G126R/R205P/T207E | |
| CL00111656 | 1.03 | 0.03 | 1.36 | 0.04 | N12E/G25S/D55P/G126K/T165D/R205P | |
| CL00111659 | 1.19 | 0.10 | 1.68 | 0.10 | G25D/D55P/G126V/T136Y/R205P/T207E | |
| CL00111673 | 1.02 | 0.00 | 1.18 | 0.12 | G25D/D55P/T179L/N181S/R205P/T207E | |
| CL00111678 | 1.00 | 0.01 | 1.14 | 0.04 | N12E/G25S/D55P/T165Y/R205P/N218S | |
| CL00111698 | 1.25 | 0.10 | 1.78 | 0.05 | N12E/G25D/D55I/G126V/T136M/R205P/N218S | |
| CL00111714 | 1.02 | 0.10 | 1.17 | 0.07 | G25S/D55P/G126R/T136M/E145A/R205P | |
| CL00111731 | 1.22 | 0.03 | 1.50 | 0.06 | N12E/G25D/D55I/G126T/T136M/R205Y | |
| CL00111771 | 1.02 | 0.07 | 1.22 | 0.01 | N12E/G25S/D55P/G126V/E145A/T179Y/R205P | |
| CL00111772 | 1.03 | 0.04 | 1.37 | 0.07 | N12E/G25S/D55P/G126T/T165Y/R205P | |
| CL00111797 | 1.04 | 0.07 | 1.15 | 0.08 | G25S/D55P/G126R/R205P/N218S | |
| CL00111817 | 1.19 | 0.03 | 1.55 | 0.09 | N12E/G25S/D55P/G126T/T136Y/R205P/T207E | G2V1 (G3P) |
| CL00111848 | 1.10 | 0.02 | 1.37 | 0.08 | N12E/G25S/D55I/G126R/T136M/T165Y/R205P/T207E/N218S | |

Figure 4C

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG140 G1P (CL00078795) | Alias |
|---|---|---|---|---|---|---|
| CL00111859 | 1.07 | 0.02 | 1.38 | 0.13 | N12E/G25S/D55P/G126S/T136M/T165Y/R205Y | |
| CL00111886 | 0.13 | 0.01 | 0.18 | 0.04 | N12D/G25D/D55P/S86A/E145M/I164T/D173P/R205P/T207E | |
| CL00111943 | 1.24 | 0.05 | 1.42 | 0.07 | N12E/G25D/A44D/D55P/S86H/Q128F/R205P | |
| CL00111975 | 1.11 | 0.03 | 1.15 | 0.03 | G25S/D55P/G126I/D173N/R205P/T207E | |
| CL00112047 | 1.05 | 0.03 | 1.20 | 0.05 | N12D/G25S/A44D/D55P/S86Q/R176H/S187N/R205P/K212E | |
| CL00112058 | 1.28 | 0.01 | 1.56 | 0.01 | N12D/G25D/A44D/D55P/Q128R/E145A/D173E/R205P | |
| CL00112063 | 1.18 | 0.05 | 1.24 | 0.06 | N12D/G25D/A44D/D55P/S86A/E145A/R205P/T207E | |
| CL00112128 | 1.08 | 0.02 | 1.10 | 0.06 | N12D/G25S/D55P/T136Y/G169T/R176H/R205P/K212E | |
| CL00112338 | 1.31 | 0.04 | 1.59 | 0.06 | N12E/G25D/D55P/S86Q/A104D/G126T/E145A/D173E/R205P/K212E | |
| CL00112344 | 1.05 | 0.01 | 1.10 | 0.01 | G25D/A44D/D55P/I164T/R205P | |
| CL00112504 | 1.10 | 0.01 | 1.20 | 0.06 | N12T/G25D/D55P/S86A/A104D/Q128R/T165Y/R176H/R205P/K212E/N218S | |
| CL00112510 | 1.18 | 0.03 | 1.19 | 0.05 | N12D/G25D/D55P/P80G/S86A/Q128R/I164T/D173E/R205P/K212E | |
| CL00112566 | 1.18 | 0.02 | 1.34 | 0.13 | N12D/G25S/D55P/Q128R/T165Y/R176H/R205P/K212E | |
| CL00112574 | 1.10 | 0.01 | 1.25 | 0.04 | N12G/G25D/A44D/D55P/Q128R/I164T/D173E/R205P | |
| CL00112612 | 1.08 | 0.03 | 1.15 | 0.06 | N12T/G25D/D55P/G126K/E145A/T165D/D173E/R205P | |
| CL00112645 | 1.11 | 0.00 | 1.20 | 0.00 | G25D/A44D/D55P/Q128R/R205P/T207E | |
| CL00112695 | 1.05 | 0.03 | 1.10 | 0.11 | G25S/D55P/G126S/T165D/G169S/T179Y/R205P/K212E | |
| CL00112727 | 1.18 | 0.06 | 1.22 | 0.06 | G25S/A44D/D55P/P80G/S86A/G126K/Q128R/R205P/K212E | |
| CL00112798 | 1.10 | 0.01 | 1.15 | 0.04 | G25S/D55P/P80G/G126T/R205P | |

Figure 4D

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG140 G1P (CL00078795) | Alias |
|---|---|---|---|---|---|---|
| CL00112926 | 1.04 | 0.03 | 1.10 | 0.06 | N12T/G25D/D55I/P80G/G126S/T152Q/S187N/R205P | |
| CL00112940 | 1.05 | 0.02 | 1.11 | 0.10 | G25S/D55P/G126K/T136R/T152Q/R176H/T179Y/R205P/K212E | |
| CL00112972 | 1.07 | 0.00 | 1.20 | 0.06 | G25D/D55P/G126T/T165Y/R176H/R205P | |
| CL00113074 | 1.12 | 0.01 | 1.15 | 0.03 | N12D/G25D/D55P/S86Q/A104D/E145A/R205P/T207E/N218S | |
| CL00113111 | 1.10 | 0.06 | 1.27 | 0.06 | G25D/A44D/D55P/A104D/Q128R/E145A/T165D/R176H/R205P/K212E | |
| CL00118595 | 1.30 | 0.14 | 1.09 | 0.07 | G25D/D55P/R205P/K212N | G2V2 |

FIGURE 5A

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG140 G1P (CL00078795) | Alias |
|---|---|---|---|---|---|---|
| CL00115231 | 1.29 | 0.04 | 1.37 | 0.07 | N12E/G25S/D55R/G126T/T136Y/R205P/T207E | |
| CL00115365 | 1.07 | 0.03 | 1.13 | 0.05 | N12E/V17I/G25S/D55P/G126T/T136Y/R205P/T207E | |
| CL00115432 | 1.21 | 0.17 | 1.23 | 0.05 | N12E/G25S/V35I/D55P/G126T/T136Y/R205P/T207E | |
| CL00115551 | 1.02 | 0.06 | 1.13 | 0.02 | N12E/G25S/D55P/G126T/V127I/T136Y/R205P/T207E | |
| CL00115863 | 1.43 | 0.07 | 1.44 | 0.05 | N12E/G25S/G42S/D55P/G126T/T136Y/R205P/T207E | |
| CL00115899 | 1.12 | 0.04 | 1.14 | 0.06 | N12E/G25S/D55P/Y124F/G126T/T136Y/R205P/T207E | |
| CL00116195 | 0.95 | 0.06 | 1.13 | 0.05 | N12E/G25S/D55P/S78T/G126T/T136Y/R205P/T207E | |
| CL00116739 | 1.14 | 0.04 | 1.20 | 0.14 | N12D/G25D/A44D/D55P/S86Q/G126T/T136Y/R176H/S187N/R205P/T207E | |
| CL00116799 | 1.03 | 0.04 | 1.13 | 0.05 | N12T/G25D/D55P/G126T/T136Y/S187N/R205P/T207E/K212E | |
| CL00116883 | 1.16 | 0.03 | 1.17 | 0.06 | N12D/G25D/D55P/G126T/T136Y/R205P/T207E | |
| CL00116899 | 1.08 | 0.03 | 1.14 | 0.08 | N12D/G25D/D55P/S86Q/G126T/T136Y/R205P/T207E | |
| CL00116988 | 1.07 | 0.02 | 1.17 | 0.09 | N12D/G25S/D55P/S86Q/G126T/T136Y/T165Y/S187N/R205P/T207E/K212E | |
| CL00118439 | 1.38 | 0.09 | 1.49 | 0.08 | N12E/G25S/S28N/D55P/G126T/T136Y/R205P/T207E | |
| CL00118543 | 1.02 | 0.01 | 1.11 | 0.02 | N12E/G25S/S39Y/D55P/G126T/T136Y/R205P/T207E | |
| CL00118596 | 1.03 | 0.07 | 1.06 | 0.08 | N12E/G25S/D55P/G126T/T136Y/R205P/T207E/K212N | G3V1 (G4P) |
| CL00120907 | | | 1.30 | | N12T/G25S/A44D/D55P/S86Q/G126N/T136M/R176H/S187N/R205P/T207E/K212E | |

Figure 5B

| Colony Tracking Number | PF AVG at pH4. 5, 50°C, 3hr | PF STD at pH4. 5, 50°C, 3hr | PF AVG at pH6. 5, 50°C, 3hr | PF STD at pH6. 5, 50°C, 3hr | AA Mutation w.r.t. EG140 G1P (CL00078795) | Alias |
|---|---|---|---|---|---|---|
| CL00120911 | | | 1.26 | | N12E/G25D/D55P/G126T/T136Y/S187N/R205P/T207E/K212E | |
| CL00121090 | | | 1.30 | | N12D/G25D/D55P/G126T/T136M/S187N/R205P/T207E | |
| CL00121097 | | | 1.38 | | N12D/G25D/D55P/A104D/G126T/T136Y/S187N/R205P/T207E/K212E | |
| CL00121159 | | | 1.22 | | N12T/G25D/D55P/S86Q/G126T/T136M/R176H/S187N/R205P/T207E/K212E | |
| CL00121195 | | | 1.21 | | N12D/G25S/A44D/D55P/S86Q/A104D/G126T/T136Y/R205P/T207E | |
| CL00121214 | | | 1.28 | | N12E/G25D/D55P/S86Q/G126T/T136M/D173L/R176H/R205P/T207E | |
| CL00121237 | | | 1.28 | | N12D/G25D/D55P/G126T/T136Y/R205P/T207E/K212E | |
| CL00121308 | | | 1.25 | | N12D/G25D/A44D/D55P/G126T/T136Y/S187N/R205P/T207E/K212E | |
| CL00121428 | | | 1.28 | | N12E/G25D/A44D/D55P/G126S/T136Y/S187N/R205P/T207E | |
| CL00121572 | | | 1.40 | | N12D/G25D/A44D/D55P/G126T/T136Y/S187N/R205P/T207E | |
| CL00121596 | | | 1.33 | | N12D/G25D/A44D/D55P/S86Q/G126K/T136Y/D173E/R176H/S187N/R205P/T207E | |

FIGURE 6A

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG185 G1P (CL00066590) | Alias |
|---|---|---|---|---|---|---|
| CL00085614 | 1.07 | 0.03 | 1.20 | 0.08 | N12S/R14P/S25D/T92I | |
| CL00085641 | 1.03 | 0.03 | 1.04 | 0.01 | T92I/Y184F | |
| CL00085648 | 1.29 | 0.14 | 1.57 | 0.04 | R14P/S25D/T92I/S138T/A161G/M172K/W175F/H182Q/Y184F/Q212N | |
| CL00085699 | 1.13 | 0.05 | 1.06 | 0.04 | N12S/I139V | |
| CL00085703 | 1.27 | 0.03 | 1.18 | 0.06 | T92I/I139V/H182Q/Y184F | |
| CL00085735 | 1.38 | 0.06 | 1.49 | 0.03 | N12S/S25D/T92I/M172K/Y184F/M194L | G1V1 |
| CL00085741 | 1.25 | 0.06 | 1.40 | 0.09 | R14P/S25D/N40S/G44S/S160A/A161G/V171I/Y184F | |
| CL00085746 | 0.98 | 0.02 | 1.07 | 0.09 | N12S/S138T/I139V/A161G/M172K/W175F/H182Q/Y184F | |
| CL00085835 | 1.35 | 0.03 | 1.53 | 0.16 | S25D/Q65G/T92I/H182Q/Y184F/M194L/Q212N | G1V2 |
| CL00085864 | 1.30 | 0.05 | 1.44 | 0.03 | N12S/R14P/S25D/S138T/S160A/Y184F | |
| CL00085883 | 1.30 | 0.04 | 1.40 | 0.11 | N12S/S25D/N40S/G44S/S138T/I139V/H182Q | |
| CL00085944 | 0.78 | 0.05 | 1.04 | 0.09 | N12S/R14P/S25D/Q65G/V171I/M172K/W175F/H182Q/Y184F | |
| CL00085945 | 0.80 | 0.02 | 1.19 | 0.02 | N12S/R14P/S25D/G44S/T92I/S138T/I139V/S160A/A161G/W175F | |
| CL00085956 | 1.05 | 0.02 | 1.13 | 0.11 | S160A/Q212N | |
| CL00085980 | 1.21 | 0.08 | 1.26 | 0.05 | N12S/R14P/S25D/S138T/A161G/Y184F | |
| CL00085981 | 0.80 | 0.13 | 1.06 | 0.11 | R14P/T92I/A161G/V171I/W175F/Y184F | |
| CL00085991 | 1.07 | 0.02 | 0.96 | 0.04 | T92I/A161G/H182Q/Y184F | |
| CL00085992 | 1.16 | 0.09 | 1.22 | 0.03 | R14P/A161G/H182Q/Y184F | |
| CL00085993 | 1.03 | 0.05 | 1.39 | 0.16 | R14P/S25D/N40S/G44S/S160A/A161G/M172K | G1V3 |
| CL00086003 | 1.03 | 0.03 | 1.08 | 0.08 | N12S/A161G/H182Q/Y184F | |

Figure 6B

| Colony Tracking Number | PF AVG at pH4.5, 50°C, 3hr | PF STD at pH4.5, 50°C, 3hr | PF AVG at pH6.5, 50°C, 3hr | PF STD at pH6.5, 50°C, 3hr | AA Mutation w.r.t. EG185 G1P (CL00066590) | Alias |
|---|---|---|---|---|---|---|
| CL00086005 | 1.04 | 0.06 | 0.95 | 0.11 | N12S/R14P/T92I/A161G/V171I/Y184F | |
| CL00086019 | 1.06 | 0.06 | 1.20 | 0.06 | S25D/N40S/T92I/S138T/S160A/A161G/V171I/H182Q/Y184F | |
| CL00086022 | 1.02 | 0.09 | 1.14 | 0.13 | R14P/S25D/N40S/G44S | |
| CL00086023 | 1.06 | 0.05 | 0.91 | 0.12 | Y184F | |
| CL00086025 | 1.16 | 0.08 | 1.19 | 0.04 | N12S/R14P/S25D/T92I/S138T/A161G | |
| CL00086026 | 0.87 | 0.11 | 1.06 | 0.03 | N12S/R14P/G44S/T92I/M194L | |
| CL00086121 | 1.14 | 0.09 | 1.21 | 0.02 | R14P/S25D/N40S/S138T/Q212N | |
| CL00086184 | 1.26 | 0.04 | 1.23 | 0.10 | N12S/S25D/N40S/G44S/Q65G | |
| CL00086189 | 1.13 | 0.03 | 1.16 | 0.07 | S25D/G44S/S138T/I139V | |
| CL00086213 | 1.03 | 0.02 | 1.09 | 0.12 | S25D/H182Q | |
| CL00086234 | 1.23 | 0.05 | 1.25 | 0.02 | R14P/S25D/G44S | |
| CL00086262 | 1.36 | 0.07 | 1.48 | 0.08 | N12S/S25D/N40S/G44S/T92I/M172K/H182Q/Q212N | |
| CL00086419 | 1.08 | 0.04 | 1.10 | 0.05 | R14P/S25D/N40S/G44S/A161G/V171I/Y184F | |
| CL00086425 | 0.92 | 0.07 | 1.01 | 0.07 | N12S/R14P/S25D/A161G/M172K/W175F/Y184F | |
| CL00086442 | 1.03 | 0.01 | 1.09 | 0.05 | N12S/R14P/S25D/N40S/G44S/T92I/I139V | |

FIGURE 7A

| Position | Residue in EG140 | Particular EG140 variants | Residue in EG185 | Particular EG185 variants |
|---|---|---|---|---|
| 12 | N | S | N | S |
| 14 |  |  | R | P |
| 25 | G | D | S | D |
| 40 | N | S | N | S |
| 44 | A | S | G | S |
| 65 | Q | G | Q | G |
| 92 |  |  | T | I |
| 138 | N | T | S | T |
| 139 | I | V | I | V |
| 160 | S | A | S | A |
| 161 | A | G | A | G |
| 171 | V | I | V | I |
| 172 | M | K | M | K |
| 175 | W | F | W | F |
| 182 | H | Q | H | Q |
| 184 | Y | F | Y | F |
| 194 | M | L | M | L |
| 212 | K | N | M | N |
| 214 | T | S | Q |  |
| 12 | N | D, E, G, T |  |  |
| 25 | G | S |  |  |
| 44 | A | D |  |  |
| 55 | D | I, P |  |  |
| 80 | P | G |  |  |

Figure 7B

| Position | Residue in EG140 | Particular EG140 variants | Residue in EG185 | Particular EG185 variants |
|---|---|---|---|---|
| 86 | S | A, H, Q | | |
| 104 | A | D | | |
| 126 | G | I, K, N, R, S, T, V | | |
| 128 | Q | F, R | | |
| 136 | T | M, R, Y | | |
| 145 | E | A, M | | |
| 152 | T | Q | | |
| 164 | I | T | | |
| 165 | T | D, Y | | |
| 169 | G | S, T | | |
| 173 | D | E, N, P | | |
| 176 | R | H | | |
| 179 | T | L, Y | | |
| 181 | N | S | | |
| 187 | S | N | | |
| 205 | R | P, Y | | |
| 207 | T | E | | |
| 212 | K | E | | |
| 218 | N | S | | |

FIGURE 8A

EG140 G1P amino acid sequence SEQ ID NO:1
QTLCNQYGTYSNGRYTVNNNLWGQGSGSGSQCTYVDSISNSGVAWHTTWTWSGGDNQV
KSYANSQVALTKKHVSQIGSIPTTVQWSYDNTNIRADVAYDLFTAADINHVTYSGDYELMI
WLARYGGVQPIGSRIGTANIAGHTWELWYGGSTQKTYSFVSATPITSFSGDVMDFWRYLT
NNHGYPASSQYLINMQFGTEPFTGGRATMKVSKFTASVN**

EG140 G1P nucleic acid sequence SEQ ID NO:2
CAAACCCTCTGTAACCAGTATGGCACCTACAGCAACGGCCGGTATACAGTCAACAACA
ACCTCTGGGGTCAGGGCTCCGGCTCCGGCTCCCAATGCACCTACGTTGATAGCATCTCC
AACTCCGGCGTGGCGTGGCACACGACCTGGACGTGGTCTGGCGGCGATAACCAGGTCA
AGAGCTACGCCAACTCGCAGGTCGCCCTTACCAAGAAGCATGTCAGCCAGATCGGCAG
TATCCCAACCACCGTGCAGTGGAGCTACGATAACACCAACATTCGTGCGGACGTAGCG
TACGATCTGTTCACAGCTGCGGATATCAACCATGTAACCTACAGCGGGGATTATGAAC
TGATGATTTGGCTCGCCCGCTACGGTGGCGTCCAGCCCATCGGCTCGCGGATTGGCACT
GCCAATATTGCCGGCCATACGTGGGAGCTGTGGTACGGCGGCAGTACCCAGAAGACGT
ACAGCTTTGTCTCTGCCACCCCGATCACCTCATTCAGTGGAGATGTCATGGACTTTTGG
CGCTATCTGACCAACAACCATGGCTACCCTGCTTCGAGCCAGTACCTGATCAATATGC
AATTCGGGACTGAGCCGTTCACTGGCGGTCGTGCCACCATGAAAGTGTCGAAGTTCAC
TGCCAGTGTAAACTAATAG EG140 G1V1 amino acid sequence SEQ ID NO:3
QTLCNQYGTYSNGRYTVNNNLWGQDSGSGSQCTYVDSISNSGVSWHTTWTWSGGDNQV
KSYANSQVALTKKHVSQIGSIPTTVQWSYDNTNIRADVAYDLFTAADINHVTYSGDYELMI
WLARYGGVQPIGSRIGTANIAGHTWELWYGGSTQKTYSFVSATPITSFSGDIKDFWRYLTN
NQGYPASSQYLINMQFGTEPFTGGRATMKVSNFTASVN**

EG140 G1V1 nucleic acid sequence SEQ ID NO:4
CAAACCCTCTGTAACCAGTATGGCACCTACAGCAACGGCCGGTATACAGTCAACAACA
ACCTCTGGGGTCAGGATTCCGGCTCCGGCTCCCAATGCACCTACGTTGATAGCATCTCC
AACTCCGGCGTGTCCTGGCACACGACCTGGACGTGGTCTGGCGGCGATAACCAGGTCA
AGAGCTACGCCAACTCGCAGGTCGCCCTTACCAAGAAGCATGTCAGCCAGATCGGCAG
TATCCCAACCACCGTGCAGTGGAGCTACGATAACACCAACATTCGTGCGGACGTAGCG
TACGATCTGTTCACAGCTGCGGATATCAACCATGTAACCTACAGCGGGGATTATGAAC
TGATGATTTGGCTCGCCCGCTACGGTGGCGTCCAGCCCATCGGCTCGCGGATTGGCACT
GCCAATATTGCCGGCCATACGTGGGAGCTGTGGTACGGCGGCAGTACCCAGAAGACGT
ACAGCTTTGTCTCTGCCACCCCGATCACCTCATTCAGTGGAGATATCAAGGACTTTTGG
CGCTATCTGACCAACAACCAGGGCTACCCTGCTTCGAGCCAGTACCTGATCAATATGC
AATTCGGGACTGAGCCGTTCACTGGCGGTCGTGCCACCATGAAAGTGTCGAACTTCAC
TGCCAGTGTAAACTAATAG EG140 G1V2 amino acid sequence SEQ ID NO:5
QTLCNQYGTYSNGRYTVNNNLWGQDSGSGSQCTYVDSISNSGVAWHTTWTWSGGDNQV
KSYANSQVALTKKHVSQIGSIPTTVQWSYDNTNIRADVAYDLFTAADINHVTYSGDYELMI
WLARYGGVQPIGSRIGTANIAGHTWELWYGGSTQKTYSFVSATPITSFSGDVMDFWRYLT
NNHGYPASSQYLINMQFGTEPFTGGRATMKVSNFTASVN**

FIGURE 8B

EG140 G1V2 nucleic acid sequence SEQ ID NO:6
CAAACCCTCTGTAACCAGTATGGCACCTACAGCAACGGCCGGTATACAGTCAACAACA
ACCTCTGGGGTCAGGATTCCGGCTCCGGCTCCCAATGCACCTACGTTGATAGCATCTCC
AACTCCGGCGTGGCGTGGCACACGACCTGGACGTGGTCTGGCGGCGATAACCAGGTCA
AGAGCTACGCCAACTCGCAGGTCGCCCTTACCAAGAAGCATGTCAGCCAGATCGGCAG
TATCCCAACCACCGTGCAGTGGAGCTACGATAACACCAACATTCGTGCGGACGTAGCG
TACGATCTGTTCACAGCTGCGGATATCAACCATGTAACCTACAGCGGGGATTATGAAC
TGATGATTTGGCTCGCCCGCTACGGTGGCGTCCAGCCCATCGGCTCGCGGATTGGCACT
GCCAATATTGCCGGCCATACGTGGGAGCTGTGGTACGGCGGCAGTACCCAGAAGACGT
ACAGCTTTGTCTCTGCCACCCCGATCACCTCATTCAGTGGAGATGTCATGGACTTTTGG
CGCTATCTGACCAACAACCATGGCTACCCTGCTTCGAGCCAGTACCTGATCAATATGC
AATTCGGGACTGAGCCGTTCACTGGCGGTCGTGCCACCATGAAAGTGTCGAACTTCAC
TGCCAGTGTAAACTAATAG EG140 G1V3 amino acid sequence SEQ ID NO:7
QTLCNQYGTYSSGRYTVNNNLWGQDSGSGSQCTYVDSISNSGVAWHTTWTWSGGDNQV
KSYANSQVALTKKHVSQIGSIPTTVQWSYDNTNIRADVAYDLFTAADINHVTYSGDYELMI
WLARYGGVQPIGSRIGTANIAGHTWELWYGGSTQKTYSFVSATPITSFSGDVMDFWRYLT
NNQGYPASSQYLINMQFGTEPFTGGRATMKVSNFTASVN**

EG140 G1V3 nucleic acid sequence SEQ ID NO:8
CAAACCCTCTGTAACCAGTATGGCACCTACAGCTCCGGCCGGTATACAGTCAACAACA
ACCTCTGGGGTCAGGATTCCGGCTCCGGCTCCCAATGCACCTACGTTGATAGCATCTCC
AACTCCGGCGTGGCGTGGCACACGACCTGGACGTGGTCTGGCGGCGATAACCAGGTCA
AGAGCTACGCCAACTCGCAGGTCGCCCTTACCAAGAAGCATGTCAGCCAGATCGGCAG
TATCCCAACCACCGTGCAGTGGAGCTACGATAACACCAACATTCGTGCGGACGTAGCG
TACGATCTGTTCACAGCTGCGGATATCAACCATGTAACCTACAGCGGGGATTATGAAC
TGATGATTTGGCTCGCCCGCTACGGTGGCGTCCAGCCCATCGGCTCGCGGATTGGCACT
GCCAATATTGCCGGCCATACGTGGGAGCTGTGGTACGGCGGCAGTACCCAGAAGACGT
ACAGCTTTGTCTCTGCCACCCCGATCACCTCATTCAGTGGAGATGTCATGGACTTTTGG
CGCTATCTGACCAACAACCAGGGCTACCCTGCTTCGAGCCAGTACCTGATCAATATGC
AATTCGGGACTGAGCCGTTCACTGGCGGTCGTGCCACCATGAAAGTGTCGAACTTCAC
TGCCAGTGTAAACTAATAG EG185 G1P amino acid sequence SEQ ID NO:9
QTLCDQYATYSNGRYTVNNNLWGKSSGSGSQCTYVDSISNSGVGWHTTWTWSGGDNQV
KSYANSQVSLTKKLVSQIGSIPTTVQWSYDNTNTRADVAYDLFTAADINHVTYSGDYELMI
WLARYGSVQPIGSQIDTASIGGHTWQLWYGGSTQKTYSFVSATPITSFSGDVMDFWDYLT
SRHGYPASSQYLINMQFGTEPFTGGPATLRVSQWTASVN**

FIGURE 8C

EG185 G1P nucleic acid sequence SEQ ID NO:10
CAAACCCTCTGCGACCAGTATGCCACCTACAGCAACGGCCGGTATACCGTCAACAATA
ACCTCTGGGGCAAGAGCTCCGGCTCCGGCTCCCAATGCACATACGTCGACAGCATCTC
CAACTCCGGCGTAGGCTGGCATACGACCTGGACGTGGTCCGGCGGCGACAACCAGGTC
AAAAGCTACGCCAACTCTCAGGTCTCCCTGACCAAGAAGCTTGTTAGCCAAATCGGCA
GTATCCCAACCACCGTGCAGTGGAGCTACGATAATACCAACACCCGCGCAGACGTAGC
CTACGATCTGTTCACAGCTGCTGATATCAACCATGTCACCTACAGCGGGGACTATGAA
CTGATGATCTGGCTCGCTCGTTATGGTAGCGTCCAACCCATCGGCTCGCAGATAGACA
CCGCTAGCATTGGCGGCCATACCTGGCAGCTGTGGTACGGCGGCAGTACCCAGAAGAC
GTACAGCTTTGTCTCTGCCACCCCGATCACCTCCTTCAGTGGCGATGTCATGGACTTTT
GGGACTATCTGACCAGCAGGCATGGTTACCCTGCTTCGAGCCAGTACCTGATCAATAT
GCAATTTGGGACTGAACCGTTCACGGGCGGTCCTGCCACCTTGAGGGTGTCGCAGTGG
ACCGCCAGTGTGAACTAATGA EG185 G1V1 amino acid sequence SEQ ID NO:11
QTLCDQYATYSSGRYTVNNNLWGKDSGSGSQCTYVDSISNSGVGWHTTWTWSGGDNQV
KSYANSQVSLTKKLVSQIGSIPTTVQWSYDNTNIRADVAYDLFTAADINHVTYSGDYELMI
WLARYGSVQPIGSQIDTASIGGHTWQLWYGGSTQKTYSFVSATPITSFSGDVKDFWDYLTS
RHGFPASSQYLINLQFGTEPFTGGPATLRVSQWTASVN**

EG185 G1V1 nucleic acid sequence SEQ ID NO:12
CAAACCCTCTGCGACCAGTATGCCACCTACAGCTCCGGCCGGTATACCGTCAACAATA
ACCTCTGGGGCAAGGATTCCGGCTCCGGCTCCCAATGCACATACGTCGACAGCATCTC
CAACTCCGGCGTAGGCTGGCATACGACCTGGACGTGGTCCGGCGGCGACAACCAGGTC
AAAAGCTACGCCAACTCTCAGGTCTCCCTGACCAAGAAGCTTGTTAGCCAAATCGGCA
GTATCCCAACCACCGTGCAGTGGAGCTACGATAATACCAACATCCGCGCAGACGTAGC
CTACGATCTGTTCACAGCTGCTGATATCAACCATGTCACCTACAGCGGGGACTATGAA
CTGATGATCTGGCTCGCTCGTTATGGTAGCGTCCAACCCATCGGCTCGCAGATAGACA
CCGCTAGCATTGGCGGCCATACCTGGCAGCTGTGGTACGGCGGCAGTACCCAGAAGAC
GTACAGCTTTGTCTCTGCCACCCCGATCACCTCCTTCAGTGGCGATGTCAAGGACTTTT
GGGACTATCTGACCAGCAGGCATGGTTTCCCTGCTTCGAGCCAGTACCTGATCAATCTG
CAATTTGGGACTGAACCGTTCACGGGCGGTCCTGCCACCTTGAGGGTGTCGCAGTGGA
CCGCCAGTGTGAACTAATGA EG185 G1V2 amino acid sequence SEQ ID NO:13
QTLCDQYATYSNGRYTVNNNLWGKDSGSGSQCTYVDSISNSGVGWHTTWTWSGGDNQV
KSYANSGVSLTKKLVSQIGSIPTTVQWSYDNTNIRADVAYDLFTAADINHVTYSGDYELMI
WLARYGSVQPIGSQIDTASIGGHTWQLWYGGSTQKTYSFVSATPITSFSGDVMDFWDYLT
SRQGFPASSQYLINLQFGTEPFTGGPATLRVSNWTASVN**

FIGURE 8D

EG185 G1V2 nucleic acid sequence SEQ ID NO:14
CAAACCCTCTGCGACCAGTATGCCACCTACAGCAACGGCCGGTATACCGTCAACAATA
ACCTCTGGGGCAAGGATTCCGGCTCCGGCTCCCAATGCACATACGTCGACAGCATCTC
CAACTCCGGCGTAGGCTGGCATACGACCTGGACGTGGTCCGGCGGCGACAACCAGGTC
AAAAGCTACGCCAACTCTGGCGTCTCCCTGACCAAGAAGCTTGTTAGCCAAATCGGCA
GTATCCCAACCACCGTGCAGTGGAGCTACGATAATACCAACATCCGCGCAGACGTAGC
CTACGATCTGTTCACAGCTGCTGATATCAACCATGTCACCTACAGCGGGGACTATGAA
CTGATGATCTGGCTCGCTCGTTATGGTAGCGTCCAACCCATCGGCTCGCAGATAGACA
CCGCTAGCATTGGCGGCCATACCTGGCAGCTGTGGTACGGCGGCAGTACCCAGAAGAC
GTACAGCTTTGTCTCTGCCACCCCGATCACCTCCTTCAGTGGCGATGTCATGGACTTTT
GGGACTATCTGACCAGCAGGCAGGGTTTCCCTGCTTCGAGCCAGTACCTGATCAATCT
GCAATTTGGGACTGAACCGTTCACGGGCGGTCCTGCCACCTTGAGGGTGTCGAACTGG
ACCGCCAGTGTGAACTAATGA EG185 G1V3 amino acid sequence SEQ ID NO:15
QTLCDQYATYSNGPYTVNNNLWGKDSGSGSQCTYVDSISSSGVSWHTTWTWSGGDNQV
KSYANSQVSLTKKLVSQIGSIPTTVQWSYDNTNTRADVAYDLFTAADINHVTYSGDYELMI
WLARYGSVQPIGSQIDTASIGGHTWQLWYGGSTQKTYSFVAGTPITSFSGDVKDFWDYLT
SRHGYPASSQYLINMQFGTEPFTGGPATLRVSQWTASVN**

EG185 G1V3 nucleic acid sequence SEQ ID NO:16
CAAACCCTCTGCGACCAGTATGCCACCTACAGCAACGGCCCCTATACCGTCAACAATA
ACCTCTGGGGCAAGGATTCCGGCTCCGGCTCCCAATGCACATACGTCGACAGCATCTC
CTCCTCCGGCGTATCCTGGCATACGACCTGGACGTGGTCCGGCGGCGACAACCAGGTC
AAAAGCTACGCCAACTCTCAGGTCTCCCTGACCAAGAAGCTTGTTAGCCAAATCGGCA
GTATCCCAACCACCGTGCAGTGGAGCTACGATAATACCAACACCCGCGCAGACGTAGC
CTACGATCTGTTCACAGCTGCTGATATCAACCATGTCACCTACAGCGGGGACTATGAA
CTGATGATCTGGCTCGCTCGTTATGGTAGCGTCCAACCCATCGGCTCGCAGATAGACA
CCGCTAGCATTGGCGGCCATACCTGGCAGCTGTGGTACGGCGGCAGTACCCAGAAGAC
GTACAGCTTTGTCGCCGGCACCCCGATCACCTCCTTCAGTGGCGATGTCAAGGACTTTT
GGGACTATCTGACCAGCAGGCATGGTTACCCTGCTTCGAGCCAGTACCTGATCAATAT
GCAATTTGGGACTGAACCGTTCACGGGCGGTCCTGCCACCTTGAGGGTGTCGCAGTGG
ACCGCCAGTGTGAACTAATGA EG140 signal peptide amino acid sequence SEQ ID NO:17
*MKTFAIFGALFSSALA*

EG185 signal peptide amino acid sequence SEQ ID NO:18
*MKTFAILGALFSCALA*

EG140 G2P amino acid sequence SEQ ID NO:19
QTLCNQYGTYSNGRYTVNNNLWGQDSGSGSQCTYVDSISNSGVAWHTTWTWSGGPNQV
KSYANSQVALTKKHVSQIGSIPTTVQWSYDNTNIRADVAYDLFTAADINHVTYSGDYELMI
WLARYGGVQPIGSRIGTANIAGHTWELWYGGSTQKTYSFVSATPITSFSGDVMDFWRYLT
NNHGYPASSQYLINMQFGTEPFTGGPATMKVSKFTASVN**

FIGURE 8E

EG140 G2P nucleic acid sequence SEQ ID NO:20
CAAACCCTCTGTAACCAGTATGGCACCTACAGCAACGGCCGGTATACAGTCAACAACA
ACCTCTGGGGTCAGGACTCCGGCTCCGGCTCCCAATGCACCTACGTTGATAGCATCTCC
AACTCCGGCGTGGCGTGGCACACGACCTGGACGTGGTCTGGCGGCCCTAACCAGGTCA
AGAGCTACGCCAACTCGCAGGTCGCCCTTACCAAGAAGCATGTCAGCCAGATCGGCAG
TATCCCAACCACCGTGCAGTGGAGCTACGATAACACCAACATTCGTGCGGACGTAGCG
TACGATCTGTTCACAGCTGCGGATATCAACCATGTAACCTACAGCGGGGATTATGAAC
TGATGATTTGGCTCGCCCGCTACGGTGGCGTCCAGCCCATCGGCTCGCGGATTGGCACT
GCCAATATTGCCGGCCATACGTGGGAGCTGTGGTACGGCGGCAGTACCCAGAAGACGT
ACAGCTTTGTCTCTGCCACCCCGATCACCTCATTCAGTGGAGATGTCATGGACTTTTGG
CGCTATCTGACCAACAACCATGGCTACCCTGCTTCGAGCCAGTACCTGATCAATATGC
AATTCGGGACTGAGCCGTTCACTGGCGGTCCTGCCACCATGAAAGTGTCGAAGTTCAC
TGCCAGTGTAAACTAATAG EG140 G3P amino acid sequence SEQ ID NO:21
QTLCNQYGTYSEGRYTVNNNLWGQSSGSGSQCTYVDSISNSGVAWHTTWTWSGGPNQV
KSYANSQVALTKKHVSQIGSIPTTVQWSYDNTNIRADVAYDLFTAADINHVTYSGDYELMI
WLARYGTVQPIGSRIGYANIAGHTWELWYGGSTQKTYSFVSATPITSFSGDVMDFWRYLT
NNHGYPASSQYLINMQFGTEPFTGGPAEMKVSKFTASVN**

EG140 G3P nucleic acid sequence SEQ ID NO:22
CAAACCCTCTGTAACCAGTATGGCACCTACAGCGAAGGCCGGTATACAGTCAACAACA
ACCTCTGGGGTCAGTCCTCCGGCTCCGGCTCCCAATGCACCTACGTTGATAGCATCTCC
AACTCCGGCGTGGCGTGGCACACGACCTGGACGTGGTCTGGCGGCCCTAACCAGGTCA
AGAGCTACGCCAACTCGCAGGTCGCCCTTACCAAGAAGCATGTCAGCCAGATCGGCAG
TATCCCAACCACCGTGCAGTGGAGCTACGATAACACCAACATTCGTGCGGACGTAGCG
TACGATCTGTTCACAGCTGCGGATATCAACCATGTAACCTACAGCGGGGATTATGAAC
TGATGATTTGGCTCGCCCGCTACGGTACCGTCCAGCCCATCGGCTCGCGGATTGGCTAT
GCCAATATTGCCGGCCATACGTGGGAGCTGTGGTACGGCGGCAGTACCCAGAAGACGT
ACAGCTTTGTCTCTGCCACCCCGATCACCTCATTCAGTGGAGATGTCATGGACTTTTGG
CGCTATCTGACCAACAACCATGGCTACCCTGCTTCGAGCCAGTACCTGATCAATATGC
AATTCGGGACTGAGCCGTTCACTGGCGGTCCTGCCGAAATGAAAGTGTCGAAGTTCAC
TGCCAGTGTAAACTAATAG EG140 G4P amino acid sequence SEQ ID NO:23
QTLCNQYGTYSEGRYTVNNNLWGQSSGSGSQCTYVDSISNSGVAWHTTWTWSGGPNQV
KSYANSQVALTKKHVSQIGSIPTTVQWSYDNTNIRADVAYDLFTAADINHVTYSGDYELMI
WLARYGTVQPIGSRIGYANIAGHTWELWYGGSTQKTYSFVSATPITSFSGDVMDFWRYLT
NNHGYPASSQYLINMQFGTEPFTGGPAEMKVSNFTASVN**

FIGURE 8F

EG140 G4P nucleic acid sequence SEQ ID NO:24
CAAACCCTCTGTAACCAGTATGGCACCTACAGCGAAGGCCGGTATACAGTCAACAACA
ACCTCTGGGGTCAGTCCTCCGGCTCCGGCTCCCAATGCACCTACGTTGATAGCATCTCC
AACTCCGGCGTGGCGTGGCACACGACCTGGACGTGGTCTGGCGGCCCTAACCAGGTCA
AGAGCTACGCCAACTCGCAGGTCGCCCTTACCAAGAAGCATGTCAGCCAGATCGGCAG
TATCCCAACCACCGTGCAGTGGAGCTACGATAACACCAACATTCGTGCGGACGTAGCG
TACGATCTGTTCACAGCTGCGGATATCAACCATGTAACCTACAGCGGGGATTATGAAC
TGATGATTTGGCTCGCCCGCTACGGTACCGTCCAGCCCATCGGCTCGCGGATTGGCTAT
GCCAATATTGCCGGCCATACGTGGGAGCTGTGGTACGGCGGCAGTACCCAGAAGACGT
ACAGCTTTGTCTCTGCCACCCCGATCACCTCATTCAGTGGAGATGTCATGGACTTTTGG
CGCTATCTGACCAACAACCATGGCTACCCTGCTTCGAGCCAGTACCTGATCAATATGC
AATTCGGGACTGAGCCGTTCACTGGCGGTCCTGCCGAAATGAAAGTGTCGAACTTCAC
TGCCAGTGTAAACTAATAG

SEQUENCE LISTING

```
<160> NUMBER OF SEQ ID NOS: 24

<210> SEQ ID NO 1
<211> LENGTH: 218
<212> TYPE: PRT
<213> ORGANISM: Artificial Sequence
<220> FEATURE:
<223> OTHER INFORMATION: Synthetic Endoglucanase (Wild type, CL00078795
      EG140 G1P)

<400> SEQUENCE: 1

Gln Thr Leu Cys Asn Gln Tyr Gly Thr Tyr Ser Asn Gly Arg Tyr Thr
1               5                   10                  15

Val Asn Asn Leu Trp Gly Gln Gly Ser Gly Ser Gln Cys
            20                  25                  30

Thr Tyr Val Asp Ser Ile Ser Asn Ser Gly Val Ala Trp His Thr Thr
        35                  40                  45

Trp Thr Trp Ser Gly Gly Asp Asn Gln Val Lys Ser Tyr Ala Asn Ser
    50                  55                  60

Gln Val Ala Leu Thr Lys Lys His Val Ser Gln Ile Gly Ser Ile Pro
65                  70                  75                  80

Thr Thr Val Gln Trp Ser Tyr Asp Asn Thr Asn Ile Arg Ala Asp Val
                85                  90                  95

Ala Tyr Asp Leu Phe Thr Ala Ala Asp Ile Asn His Val Thr Tyr Ser
            100                 105                 110

Gly Asp Tyr Glu Leu Met Ile Trp Leu Ala Arg Tyr Gly Gly Val Gln
        115                 120                 125

Pro Ile Gly Ser Arg Ile Gly Thr Ala Asn Ile Ala Gly His Thr Trp
    130                 135                 140

Glu Leu Trp Tyr Gly Gly Ser Thr Gln Lys Thr Tyr Ser Phe Val Ser
145                 150                 155                 160

Ala Thr Pro Ile Thr Ser Phe Ser Gly Asp Val Met Asp Phe Trp Arg
                165                 170                 175

Tyr Leu Thr Asn Asn His Gly Tyr Pro Ala Ser Ser Gln Tyr Leu Ile
            180                 185                 190

Asn Met Gln Phe Gly Thr Glu Pro Phe Thr Gly Gly Arg Ala Thr Met
        195                 200                 205

Lys Val Ser Lys Phe Thr Ala Ser Val Asn
    210                 215

<210> SEQ ID NO 2
<211> LENGTH: 660
<212> TYPE: DNA
<213> ORGANISM: Artificial Sequence
<220> FEATURE:
<223> OTHER INFORMATION: Synthetic Endoglucanase (Wild type, CL00078795
      EG140 G1P)

<400> SEQUENCE: 2
caaaccctct gtaaccagta tggcacctac agcaacggcc ggtatacagt caacaacaac        60
```

-continued

```
ctctggggtc agggctccgg ctccggctcc caatgcacct acgttgatag catctccaac      120
tccggcgtgg cgtggcacac gacctggacg tggtctggcg gcgataacca ggtcaagagc      180
tacgccaact cgcaggtcgc ccttaccaag aagcatgtca gccagatcgg cagtatccca      240
accaccgtgc agtggagcta cgataacacc aacattcgtg cggacgtagc gtacgatctg      300
ttcacagctg cggatatcaa ccatgtaacc tacagcgggg attatgaact gatgatttgg      360
ctcgcccgct acggtggcgt ccagcccatc ggctcgcgga ttggcactgc caatattgcc      420
ggccatacgt gggagctgtg gtacggcggc agtacccaga agacgtacag ctttgtctct      480
gccaccccga tcacctcatt cagtggagat gtcatggact tttggcgcta tctgaccaac      540
aaccatggct accctgcttc gagccagtac ctgatcaata tgcaattcgg gactgagccg      600
ttcactggcg gtcgtgccac catgaaagtg tcgaagttca ctgccagtgt aaactaatag      660
```

<210> SEQ ID NO 3
<211> LENGTH: 218
<212> TYPE: PRT
<213> ORGANISM: Artificial Sequence
<220> FEATURE:
<223> OTHER INFORMATION: Synthetic Endoglucanase (CL00088425 EG140 G1V1)

<400> SEQUENCE: 3

```
Gln Thr Leu Cys Asn Gln Tyr Gly Thr Tyr Ser Asn Gly Arg Tyr Thr
 1               5                  10                  15

Val Asn Asn Asn Leu Trp Gly Gln Asp Ser Gly Ser Gly Ser Gln Cys
            20                  25                  30

Thr Tyr Val Asp Ser Ile Ser Asn Ser Gly Val Ser Trp His Thr Thr
        35                  40                  45

Trp Thr Trp Ser Gly Gly Asp Asn Gln Val Lys Ser Tyr Ala Asn Ser
    50                  55                  60

Gln Val Ala Leu Thr Lys Lys His Val Ser Gln Ile Gly Ser Ile Pro
65                  70                  75                  80

Thr Thr Val Gln Trp Ser Tyr Asp Asn Thr Asn Ile Arg Ala Asp Val
                85                  90                  95

Ala Tyr Asp Leu Phe Thr Ala Ala Asp Ile Asn His Val Thr Tyr Ser
            100                 105                 110

Gly Asp Tyr Glu Leu Met Ile Trp Leu Ala Arg Tyr Gly Gly Val Gln
        115                 120                 125

Pro Ile Gly Ser Arg Ile Gly Thr Ala Asn Ile Ala Gly His Thr Trp
    130                 135                 140

Glu Leu Trp Tyr Gly Gly Ser Thr Gln Lys Thr Tyr Ser Phe Val Ser
145                 150                 155                 160

Ala Thr Pro Ile Thr Ser Phe Ser Gly Asp Ile Lys Asp Phe Trp Arg
                165                 170                 175

Tyr Leu Thr Asn Asn Gln Gly Tyr Pro Ala Ser Ser Gln Tyr Leu Ile
            180                 185                 190

Asn Met Gln Phe Gly Thr Glu Pro Phe Thr Gly Gly Arg Ala Thr Met
        195                 200                 205

Lys Val Ser Asn Phe Thr Ala Ser Val Asn
    210                 215
```

<210> SEQ ID NO 4
<211> LENGTH: 660
<212> TYPE: DNA
<213> ORGANISM: Artificial Sequence
<220> FEATURE:

<223> OTHER INFORMATION: Synthetic Endoglucanase (CL00088425 EG140 G1V1)

<400> SEQUENCE: 4

```
caaaccctct gtaaccagta tggcacctac agcaacggcc ggtatacagt caacaacaac    60
ctctggggtc aggattccgg ctccggctcc caatgcacct acgttgatag catctccaac   120
tccggcgtgt cctggcacac gacctggacg tggtctggcg gcgataacca ggtcaagagc   180
tacgccaact cgcaggtcgc ccttaccaag aagcatgtca gccagatcgg cagtatccca   240
accaccgtgc agtggagcta cgataacacc aacattcgtg cggacgtagc gtacgatctg   300
ttcacagctg cggatatcaa ccatgtaacc tacagcgggg attatgaact gatgatttgg   360
ctcgcccgct acggtggcgt ccagcccatc ggctcgcgga ttggcactgc caatattgcc   420
ggccatacgt gggagctgtg gtacggcggc agtacccaga gacgtacag ctttgtctct    480
gccaccccga tcacctcatt cagtggagat atcaaggact tttggcgcta tctgaccaac   540
aaccagggct accctgcttc gagccagtac ctgatcaata tgcaattcgg gactgagccg   600
ttcactggcg gtcgtgccac catgaaagtg tcgaacttca ctgccagtgt aaactaatag   660
```

<210> SEQ ID NO 5
<211> LENGTH: 218
<212> TYPE: PRT
<213> ORGANISM: Artificial Sequence
<220> FEATURE:
<223> OTHER INFORMATION: Synthetic Endoglucanase (CL00088465 EG140 G1V2)

<400> SEQUENCE: 5

```
Gln Thr Leu Cys Asn Gln Tyr Gly Thr Tyr Ser Asn Gly Arg Tyr Thr
1               5                   10                  15

Val Asn Asn Leu Trp Gly Gln Asp Ser Gly Ser Gly Ser Gln Cys
            20                  25                  30

Thr Tyr Val Asp Ser Ile Ser Asn Ser Gly Val Ala Trp His Thr Thr
        35                  40                  45

Trp Thr Trp Ser Gly Gly Asp Asn Gln Val Lys Ser Tyr Ala Asn Ser
    50                  55                  60

Gln Val Ala Leu Thr Lys Lys His Val Ser Gln Ile Gly Ser Ile Pro
65                  70                  75                  80

Thr Thr Val Gln Trp Ser Tyr Asp Asn Thr Asn Ile Arg Ala Asp Val
                85                  90                  95

Ala Tyr Asp Leu Phe Thr Ala Ala Asp Ile Asn His Val Thr Tyr Ser
            100                 105                 110

Gly Asp Tyr Glu Leu Met Ile Trp Leu Ala Arg Tyr Gly Gly Val Gln
        115                 120                 125

Pro Ile Gly Ser Arg Ile Gly Thr Ala Asn Ile Ala Gly His Thr Trp
    130                 135                 140

Glu Leu Trp Tyr Gly Gly Ser Thr Gln Lys Thr Tyr Ser Phe Val Ser
145                 150                 155                 160

Ala Thr Pro Ile Thr Ser Phe Ser Gly Asp Val Met Asp Phe Trp Arg
                165                 170                 175

Tyr Leu Thr Asn Asn His Gly Tyr Pro Ala Ser Ser Gln Tyr Leu Ile
            180                 185                 190

Asn Met Gln Phe Gly Thr Glu Pro Phe Thr Gly Gly Arg Ala Thr Met
        195                 200                 205

Lys Val Ser Asn Phe Thr Ala Ser Val Asn
    210                 215
```

<210> SEQ ID NO 6
<211> LENGTH: 660
<212> TYPE: DNA
<213> ORGANISM: Artificial Sequence
<220> FEATURE:
<223> OTHER INFORMATION: Synthetic Endoglucanase (CL00088465 EG140 G1V2)

<400> SEQUENCE: 6

```
caaaccctct gtaaccagta tggcacctac agcaacggcc ggtatacagt caacaacaac    60
ctctggggtc aggattccgg ctccggctcc caatgcacct acgttgatag catctccaac   120
tccggcgtgg cgtggcacac gacctggacg tggtctggcg gcgataacca ggtcaagagc   180
tacgccaact cgcaggtcgc ccttaccaag aagcatgtca gccagatcgg cagtatccca   240
accaccgtgc agtggagcta cgataacacc aacattcgtg cggacgtagc gtacgatctg   300
ttcacagctg cggatatcaa ccatgtaacc tacagcgggg attatgaact gatgatttgg   360
ctcgcccgct acggtggcgt ccagcccatc ggctcgcgga ttggcactgc caatattgcc   420
ggccatacgt gggagctgtg gtacggcggc agtacccaga gacgtacag ctttgtctct   480
gccaccccga tcacctcatt cagtggagat gtcatggact tttggcgcta tctgaccaac   540
aaccatggct accctgcttc gagccagtac ctgatcaata tgcaattcgg gactgagccg   600
ttcactggcg gtcgtgccac catgaaagtg tcgaacttca ctgccagtgt aaactaatag   660
```

<210> SEQ ID NO 7
<211> LENGTH: 218
<212> TYPE: PRT
<213> ORGANISM: Artificial Sequence
<220> FEATURE:
<223> OTHER INFORMATION: Synthetic Endoglucanase (CL00088553 EG140 G1V3)

<400> SEQUENCE: 7

```
Gln Thr Leu Cys Asn Gln Tyr Gly Thr Tyr Ser Ser Gly Arg Tyr Thr
 1               5                  10                  15

Val Asn Asn Leu Trp Gly Gln Asp Ser Gly Ser Gly Ser Gln Cys
             20                  25                  30

Thr Tyr Val Asp Ser Ile Ser Asn Ser Gly Val Ala Trp His Thr Thr
         35                  40                  45

Trp Thr Trp Ser Gly Gly Asp Asn Gln Val Lys Ser Tyr Ala Asn Ser
 50                  55                  60

Gln Val Ala Leu Thr Lys Lys His Val Ser Gln Ile Gly Ser Ile Pro
 65                  70                  75                  80

Thr Thr Val Gln Trp Ser Tyr Asp Asn Thr Asn Ile Arg Ala Asp Val
                 85                  90                  95

Ala Tyr Asp Leu Phe Thr Ala Ala Asp Ile Asn His Val Thr Tyr Ser
            100                 105                 110

Gly Asp Tyr Glu Leu Met Ile Trp Leu Ala Arg Tyr Gly Gly Val Gln
        115                 120                 125

Pro Ile Gly Ser Arg Ile Gly Thr Ala Asn Ile Ala Gly His Thr Trp
    130                 135                 140

Glu Leu Trp Tyr Gly Gly Ser Thr Gln Lys Thr Tyr Ser Phe Val Ser
145                 150                 155                 160

Ala Thr Pro Ile Thr Ser Phe Ser Gly Asp Val Met Asp Phe Trp Arg
                165                 170                 175

Tyr Leu Thr Asn Asn Gln Gly Tyr Pro Ala Ser Ser Gln Tyr Leu Ile
            180                 185                 190

Asn Met Gln Phe Gly Thr Glu Pro Phe Thr Gly Gly Arg Ala Thr Met
        195                 200                 205
```

Lys Val Ser Asn Phe Thr Ala Ser Val Asn
    210                 215

<210> SEQ ID NO 8
<211> LENGTH: 660
<212> TYPE: DNA
<213> ORGANISM: Artificial Sequence
<220> FEATURE:
<223> OTHER INFORMATION: Synthetic Endoglucanase (CL00088553 EG140 G1V3)

<400> SEQUENCE: 8

```
caaaccctct gtaaccagta tggcacctac agctccggcc ggtatacagt caacaacaac    60
ctctggggtc aggattccgg ctccggctcc caatgcacct acgttgatag catctccaac   120
tccggcgtgg cgtggcacac gacctggacg tggtctggcg gcgataacca ggtcaagagc   180
tacgccaact cgcaggtcgc ccttaccaag aagcatgtca gccagatcgg cagtatccca   240
accaccgtgc agtggagcta cgataacacc aacattcgtg cggacgtagc gtacgatctg   300
ttcacagctg cggatatcaa ccatgtaacc tacagcgggg attatgaact gatgatttgg   360
ctcgcccgct acggtggcgt ccagcccatc ggctcgcgga ttggcactgc aatattgcc    420 ggccatacgt gggagctgtg gtacggcggc agtacccaga gacgtacag ctttgtctct     480 gccaccccga tcacctcatt cagtggagat gtcatggact tttggcgcta tctgaccaac    540
aaccagggct accctgcttc gagccagtac ctgatcaata tgcaattcgg gactgagccg    600
ttcactggcg gtcgtgccac catgaaagtg tcgaacttca ctgccagtgt aaactaatag    660
```

<210> SEQ ID NO 9
<211> LENGTH: 218
<212> TYPE: PRT
<213> ORGANISM: Artificial Sequence
<220> FEATURE:
<223> OTHER INFORMATION: Synthetic Endoglucanase (Wild type, CL00066590
      EG185 G1P)

<400> SEQUENCE: 9

Gln Thr Leu Cys Asp Gln Tyr Ala Thr Tyr Ser Asn Gly Arg Tyr Thr
1               5                   10                  15

Val Asn Asn Asn Leu Trp Gly Lys Ser Gly Ser Gly Ser Gln Cys
            20                  25                  30

Thr Tyr Val Asp Ser Ile Ser Asn Ser Gly Val Gly Trp His Thr Thr
        35                  40                  45

Trp Thr Trp Ser Gly Gly Asp Asn Gln Val Lys Ser Tyr Ala Asn Ser
    50                  55                  60

Gln Val Ser Leu Thr Lys Lys Leu Val Ser Gln Ile Gly Ser Ile Pro
65                  70                  75                  80

Thr Thr Val Gln Trp Ser Tyr Asp Asn Thr Asn Thr Arg Ala Asp Val
                85                  90                  95

Ala Tyr Asp Leu Phe Thr Ala Asp Ile Asn His Val Thr Tyr Ser
            100                 105                 110

Gly Asp Tyr Glu Leu Met Ile Trp Leu Ala Arg Tyr Gly Ser Val Gln
        115                 120                 125

Pro Ile Gly Ser Gln Ile Asp Thr Ala Ser Ile Gly Gly His Thr Trp
    130                 135                 140

Gln Leu Trp Tyr Gly Gly Ser Thr Gln Lys Thr Tyr Ser Phe Val Ser
145                 150                 155                 160

Ala Thr Pro Ile Thr Ser Phe Ser Gly Asp Val Met Asp Phe Trp Asp
                165                 170                 175

Tyr Leu Thr Ser Arg His Gly Tyr Pro Ala Ser Ser Gln Tyr Leu Ile
            180                 185                 190

Asn Met Gln Phe Gly Thr Glu Pro Phe Thr Gly Pro Ala Thr Leu
        195                 200                 205

Arg Val Ser Gln Trp Thr Ala Ser Val Asn
    210                 215

<210> SEQ ID NO 10
<211> LENGTH: 660
<212> TYPE: DNA
<213> ORGANISM: Artificial Sequence
<220> FEATURE:
<223> OTHER INFORMATION: Synthetic Endoglucanase (Wild type, CL00066590
      EG185 G1P)

<400> SEQUENCE: 10
caaaccctct gcgaccagta tgccacctac agcaacggcc ggtataccgt caacaataac        60
ctctggggca agagctccgg ctccggctcc caatgcacat acgtcgacag catctccaac       120
tccggcgtag gctggcatac gacctggacg tggtccggcg gcgacaacca ggtcaaaagc       180
tacgccaact ctcaggtctc cctgaccaag aagcttgtta gccaaatcgg cagtatccca       240
accaccgtgc agtggagcta cgataatacc aacacccgcg cagacgtagc ctacgatctg       300
ttcacagctg ctgatatcaa ccatgtcacc tacagcgggg actatgaact gatgatctgg       360
ctcgctcgtt atggtagcgt ccaacccatc ggctcgcaga tagacaccgc tagcattggc       420
ggccatacct ggcagctgtg gtacggcggc agtacccaga gacgtacag ctttgtctct       480 gccaccccga tcacctcctt cagtggcgat gtcatggact ttgggacta tctgaccagc       540 aggcatggtt accctgcttc gagccagtac ctgatcaata tgcaatttgg gactgaaccg       600

ttcacgggcg gtcctgccac cttgagggtg tcgcagtgga ccgccagtgt gaactaatga       660

<210> SEQ ID NO 11
<211> LENGTH: 218
<212> TYPE: PRT
<213> ORGANISM: Artificial Sequence
<220> FEATURE:
<223> OTHER INFORMATION: Synthetic Endoglucanase (CL00085735 EG185 G1V1)

<400> SEQUENCE: 11

Gln Thr Leu Cys Asp Gln Tyr Ala Thr Tyr Ser Ser Gly Arg Tyr Thr
1               5                   10                  15

Val Asn Asn Asn Leu Trp Gly Lys Asp Ser Gly Ser Gly Ser Gln Cys
            20                  25                  30

Thr Tyr Val Asp Ser Ile Ser Asn Ser Gly Val Gly Trp His Thr Thr
        35                  40                  45

Trp Thr Trp Ser Gly Gly Asp Asn Gln Val Lys Ser Tyr Ala Asn Ser
    50                  55                  60

Gln Val Ser Leu Thr Lys Lys Leu Val Ser Gln Ile Gly Ser Ile Pro
65                  70                  75                  80

Thr Thr Val Gln Trp Ser Tyr Asp Asn Thr Asn Ile Arg Ala Asp Val
            85                  90                  95

Ala Tyr Asp Leu Phe Thr Ala Ala Asp Ile Asn His Val Thr Tyr Ser
            100                 105                 110

Gly Asp Tyr Glu Leu Met Ile Trp Leu Ala Arg Tyr Gly Ser Val Gln
        115                 120                 125

Pro Ile Gly Ser Gln Ile Asp Thr Ala Ser Ile Gly Gly His Thr Trp
    130                 135                 140

Gln Leu Trp Tyr Gly Gly Ser Thr Gln Lys Thr Tyr Ser Phe Val Ser
145                 150                 155                 160

Ala Thr Pro Ile Thr Ser Phe Ser Gly Asp Val Lys Asp Phe Trp Asp
                165                 170                 175

Tyr Leu Thr Ser Arg His Gly Phe Pro Ala Ser Ser Gln Tyr Leu Ile
            180                 185                 190

Asn Leu Gln Phe Gly Thr Glu Pro Phe Thr Gly Gly Pro Ala Thr Leu
        195                 200                 205

Arg Val Ser Gln Trp Thr Ala Ser Val Asn
    210                 215

<210> SEQ ID NO 12
<211> LENGTH: 660
<212> TYPE: DNA
<213> ORGANISM: Artificial Sequence
<220> FEATURE:
<223> OTHER INFORMATION: Synthetic Endoglucanase (CL00085735 EG185 G1V1)

<400> SEQUENCE: 12
caaaccctct gcgaccagta tgccacctac agctccggcc ggtataccgt caacaataac      60
ctctggggca aggattccgg ctccggctcc aatgcacat acgtcgacag catctccaac      120
tccggcgtag ctggcatac gacctggacg tggtccggcg gcgacaacca ggtcaaaagc      180
tacgccaact ctcaggtctc cctgaccaag aagcttgtta gccaaatcgg cagtatccca      240
accaccgtgc agtggagcta cgataatacc aacatccgcg cagacgtagc ctacgatctg      300
ttcacagctg ctgatatcaa ccatgtcacc tacagcgggg actatgaact gatgatctgg      360
ctcgctcgtt atggtagcgt ccaacccatc ggctcgcaga tagacaccgc tagcattggc      420
ggccatacct ggcagctgtg gtacggcggc agtacccaga gacgtacag ctttgtctct      480 gccaccccga tcacctcctt cagtggcgat gtcaaggact tttgggacta tctgaccagc      540
aggcatggtt tccctgcttc gagccagtac ctgatcaatc tgcaatttgg gactgaaccg      600
ttcacgggcg gtcctgccac cttgagggtg tcgcagtgga ccgccagtgt gaactaatga      660

<210> SEQ ID NO 13
<211> LENGTH: 218
<212> TYPE: PRT
<213> ORGANISM: Artificial Sequence
<220> FEATURE:
<223> OTHER INFORMATION: Synthetic Endoglucanase (CL00085835 EG185 G1V2)

<400> SEQUENCE: 13

Gln Thr Leu Cys Asp Gln Tyr Ala Thr Tyr Ser Asn Gly Arg Tyr Thr
1               5                   10                  15

Val Asn Asn Asn Leu Trp Gly Lys Asp Ser Gly Ser Gly Ser Gln Cys
            20                  25                  30

Thr Tyr Val Asp Ser Ile Ser Asn Ser Gly Val Gly Trp His Thr Thr
        35                  40                  45

Trp Thr Trp Ser Gly Gly Asp Asn Gln Val Lys Ser Tyr Ala Asn Ser
    50                  55                  60

Gly Val Ser Leu Thr Lys Lys Leu Val Ser Gln Ile Gly Ser Ile Pro
65                  70                  75                  80

Thr Thr Val Gln Trp Ser Tyr Asp Asn Thr Asn Ile Arg Ala Asp Val
                85                  90                  95

Ala Tyr Asp Leu Phe Thr Ala Ala Asp Ile Asn His Val Thr Tyr Ser
            100                 105                 110

Gly Asp Tyr Glu Leu Met Ile Trp Leu Ala Arg Tyr Gly Ser Val Gln
            115                 120                 125

Pro Ile Gly Ser Gln Ile Asp Thr Ala Ser Ile Gly Gly His Thr Trp
        130                 135                 140

Gln Leu Trp Tyr Gly Gly Ser Thr Gln Lys Thr Tyr Ser Phe Val Ser
145                 150                 155                 160

Ala Thr Pro Ile Thr Ser Phe Ser Gly Asp Val Met Asp Phe Trp Asp
                165                 170                 175

Tyr Leu Thr Ser Arg Gln Gly Phe Pro Ala Ser Ser Gln Tyr Leu Ile
            180                 185                 190

Asn Leu Gln Phe Gly Thr Glu Pro Phe Thr Gly Gly Pro Ala Thr Leu
        195                 200                 205

Arg Val Ser Asn Trp Thr Ala Ser Val Asn
    210                 215

<210> SEQ ID NO 14
<211> LENGTH: 660
<212> TYPE: DNA
<213> ORGANISM: Artificial Sequence
<220> FEATURE:
<223> OTHER INFORMATION: Synthetic Endoglucanase (CL00085835 EG185 G1V2)

<400> SEQUENCE: 14
caaaccctct gcgaccagta tgccacctac agcaacggcc ggtataccgt caacaataac    60
ctctggggca aggattccgg ctccggctcc aatgcacat acgtcgacag catctccaac   120
tccggcgtag gctggcatac gacctggacg tggtccggcg gcgacaacca ggtcaaaagc   180
tacgccaact ctggcgtctc cctgaccaag aagcttgtta gccaaatcgg cagtatccca   240
accaccgtgc agtggagcta cgataatacc aacatccgcg cagacgtagc ctacgatctg   300
ttcacagctg ctgatatcaa ccatgtcacc tacagcgggg actatgaact gatgatctgg   360
ctcgctcgtt atggtagcgt ccaacccatc ggctcgcaga tagacaccgc tagcattggc   420 ggccataccct ggcagctgtg gtacggcggc agtacccaga gacgtacag ctttgtctct   480 gccaccccga tcacctcctt cagtggcgat gtcatggact tttgggacta tctgaccagc   540
aggcagggtt ccctgcttc gagccagtac ctgatcaatc tgcaatttgg gactgaaccg   600
ttcacgggcg gtcctgccac cttgagggtg tcgaactgga ccgccagtgt gaactaatga   660

<210> SEQ ID NO 15
<211> LENGTH: 218
<212> TYPE: PRT
<213> ORGANISM: Artificial Sequence
<220> FEATURE:
<223> OTHER INFORMATION: Synthetic Endoglucanase (CL00085993 EG185 G1V3)

<400> SEQUENCE: 15

Gln Thr Leu Cys Asp Gln Tyr Ala Thr Tyr Ser Asn Gly Pro Tyr Thr
1               5                   10                  15

Val Asn Asn Asn Leu Trp Gly Lys Asp Ser Gly Ser Gly Ser Gln Cys
            20                  25                  30

Thr Tyr Val Asp Ser Ile Ser Ser Gly Val Ser Trp His Thr Thr
        35                  40                  45

Trp Thr Trp Ser Gly Gly Asp Asn Gln Val Lys Ser Tyr Ala Asn Ser
    50                  55                  60

Gln Val Ser Leu Thr Lys Lys Leu Val Ser Gln Ile Gly Ser Ile Pro
65                  70                  75                  80

Thr Thr Val Gln Trp Ser Tyr Asp Asn Thr Asn Thr Arg Ala Asp Val

```
                85                  90                  95
Ala Tyr Asp Leu Phe Thr Ala Ala Asp Ile Asn His Val Thr Tyr Ser
            100                 105                 110

Gly Asp Tyr Glu Leu Met Ile Trp Leu Ala Arg Tyr Gly Ser Val Gln
            115                 120                 125

Pro Ile Gly Ser Gln Ile Asp Thr Ala Ser Ile Gly Gly His Thr Trp
        130                 135                 140

Gln Leu Trp Tyr Gly Gly Ser Thr Gln Lys Thr Tyr Ser Phe Val Ala
145                 150                 155                 160

Gly Thr Pro Ile Thr Ser Phe Ser Gly Asp Val Lys Asp Phe Trp Asp
                165                 170                 175

Tyr Leu Thr Ser Arg His Gly Tyr Pro Ala Ser Ser Gln Tyr Leu Ile
            180                 185                 190

Asn Met Gln Phe Gly Thr Glu Pro Phe Thr Gly Gly Pro Ala Thr Leu
        195                 200                 205

Arg Val Ser Gln Trp Thr Ala Ser Val Asn
    210                 215
```

<210> SEQ ID NO 16
<211> LENGTH: 660
<212> TYPE: DNA
<213> ORGANISM: Artificial Sequence
<220> FEATURE:
<223> OTHER INFORMATION: Synthetic Endoglucanase (CL00085993 EG185 G1V3)

<400> SEQUENCE: 16

```
caaaccctct gcgaccagta tgccacctac agcaacggcc cctataccgt caacaataac      60
ctctggggca aggattccgg ctccggctcc caatgcacat acgtcgacag catctcctcc     120
tccggcgtat cctggcatac gacctggacg tggtccggcg cgacaaccca ggtcaaaagc     180
tacgccaact tcaggtctc cctgaccaag aagcttgtta gccaaatcgg cagtatccca     240
accaccgtgc agtggagcta cgataatacc aacacccgcg cagacgtagc ctacgatctg     300
ttcacagctg ctgatatcaa ccatgtcacc tacagcgggg actatgaact gatgatctgg     360
ctcgctcgtt atggtagcgt ccaacccatc ggctcgcaga tagacaccgc tagcattggc     420
ggccataacct ggcagctgtg gtacggcggc agtacccaga gacgtacag ctttgtcgcc     480
ggcacccccga tcacctcctt cagtggcgat gtcaaggact tttggggacta tctgaccagc     540
aggcatggtt accctgcttc gagccagtac ctgatcaata tgcaatttgg gactgaaccg     600
ttcacgggcg gtcctgccac cttgagggtg tcgcagtgga ccgccagtgt gaactaatga     660
```

<210> SEQ ID NO 17
<211> LENGTH: 16
<212> TYPE: PRT
<213> ORGANISM: Artificial Sequence
<220> FEATURE:
<223> OTHER INFORMATION: Synthetic Endoglucanase (EG140 signal peptide)

<400> SEQUENCE: 17

```
Met Lys Thr Phe Ala Ile Phe Gly Ala Leu Phe Ser Ser Ala Leu Ala
1               5                   10                  15
```

<210> SEQ ID NO 18
<211> LENGTH: 16
<212> TYPE: PRT
<213> ORGANISM: Artificial Sequence
<220> FEATURE:
<223> OTHER INFORMATION: Synthetic Endoglucanase (EG185 signal peptide)

<400> SEQUENCE: 18

Met Lys Thr Phe Ala Ile Leu Gly Ala Leu Phe Ser Cys Ala Leu Ala
1               5                   10                  15

<210> SEQ ID NO 19
<211> LENGTH: 218
<212> TYPE: PRT
<213> ORGANISM: Artificial Sequence
<220> FEATURE:
<223> OTHER INFORMATION: Synthetic Endoglucanase (CL00098799 EG140 G1V4
      G2P)

<400> SEQUENCE: 19

Gln Thr Leu Cys Asn Gln Tyr Gly Thr Tyr Ser Asn Gly Arg Tyr Thr
1               5                   10                  15

Val Asn Asn Leu Trp Gly Gln Asp Ser Gly Ser Gly Ser Gln Cys
            20                  25                  30

Thr Tyr Val Asp Ser Ile Ser Asn Ser Gly Val Ala Trp His Thr Thr
        35                  40                  45

Trp Thr Trp Ser Gly Gly Pro Asn Gln Val Lys Ser Tyr Ala Asn Ser
    50                  55                  60

Gln Val Ala Leu Thr Lys Lys His Val Ser Gln Ile Gly Ser Ile Pro
65                  70                  75                  80

Thr Thr Val Gln Trp Ser Tyr Asp Asn Thr Asn Ile Arg Ala Asp Val
                85                  90                  95

Ala Tyr Asp Leu Phe Thr Ala Ala Asp Ile Asn His Val Thr Tyr Ser
            100                 105                 110

Gly Asp Tyr Glu Leu Met Ile Trp Leu Ala Arg Tyr Gly Gly Val Gln
        115                 120                 125

Pro Ile Gly Ser Arg Ile Gly Thr Ala Asn Ile Ala Gly His Thr Trp
    130                 135                 140

Glu Leu Trp Tyr Gly Gly Ser Thr Gln Lys Thr Tyr Ser Phe Val Ser
145                 150                 155                 160

Ala Thr Pro Ile Thr Ser Phe Ser Gly Asp Val Met Asp Phe Trp Arg
                165                 170                 175

Tyr Leu Thr Asn Asn His Gly Tyr Pro Ala Ser Ser Gln Tyr Leu Ile
            180                 185                 190

Asn Met Gln Phe Gly Thr Glu Pro Phe Thr Gly Gly Pro Ala Thr Met
        195                 200                 205

Lys Val Ser Lys Phe Thr Ala Ser Val Asn
    210                 215

<210> SEQ ID NO 20
<211> LENGTH: 660
<212> TYPE: DNA
<213> ORGANISM: Artificial Sequence
<220> FEATURE:
<223> OTHER INFORMATION: Synthetic Endoglucanase (CL00098799 EG140 G1V4
      G2P)

<400> SEQUENCE: 20
caaaccctct gtaaccagta tggcacctac agcaacggcc ggtatacagt caacaacaac      60
ctctggggtc aggactccgg ctccggctcc aatgcacct acgttgatag catctccaac     120
tccggcgtgg cgtggcacac gacctggacg tggtctggcg ccctaaccag gtcaagagc      180 tacgccaact cgcaggtcgc ccttaccaag aagcatgtca gccagatcgg cagtatccca     240
accaccgtgc agtggagcta cgataacacc aacattcgtg cggacgtagc gtacgatctg     300

```
ttcacagctg cggatatcaa ccatgtaacc tacagcgggg attatgaact gatgatttgg    360
ctcgcccgct acgtggcgt ccagcccatc ggctcgcgga ttggcactgc caatattgcc    420
ggccatacgt gggagctgtg gtacggcggc agtacccaga agacgtacag ctttgtctct    480
gccaccccga tcacctcatt cagtggagat gtcatggact tttggcgcta tctgaccaac    540
aaccatggct accctgcttc gagccagtac ctgatcaata tgcaattcgg gactgagccg    600
ttcactggcg gtcctgccac catgaaagtg tcgaagttca ctgccagtgt aaactaatag    660
```

<210> SEQ ID NO 21
<211> LENGTH: 218
<212> TYPE: PRT
<213> ORGANISM: Artificial Sequence
<220> FEATURE:
<223> OTHER INFORMATION: Synthetic Endoglucanase (CL00111817 EG140 G2V1 G3P)

<400> SEQUENCE: 21

```
Gln Thr Leu Cys Asn Gln Tyr Gly Thr Tyr Ser Glu Gly Arg Tyr Thr
 1               5                  10                  15

Val Asn Asn Asn Leu Trp Gly Gln Ser Ser Gly Ser Gly Ser Gln Cys
                20                  25                  30

Thr Tyr Val Asp Ser Ile Ser Asn Ser Gly Val Ala Trp His Thr Thr
            35                  40                  45

Trp Thr Trp Ser Gly Gly Pro Asn Gln Val Lys Ser Tyr Ala Asn Ser
        50                  55                  60

Gln Val Ala Leu Thr Lys Lys His Val Ser Gln Ile Gly Ser Ile Pro
 65                 70                  75                  80

Thr Thr Val Gln Trp Ser Tyr Asp Asn Thr Asn Ile Arg Ala Asp Val
                 85                  90                  95

Ala Tyr Asp Leu Phe Thr Ala Ala Asp Ile Asn His Val Thr Tyr Ser
            100                 105                 110

Gly Asp Tyr Glu Leu Met Ile Trp Leu Ala Arg Tyr Gly Thr Val Gln
        115                 120                 125

Pro Ile Gly Ser Arg Ile Gly Tyr Ala Asn Ile Ala Gly His Thr Trp
    130                 135                 140

Glu Leu Trp Tyr Gly Gly Ser Thr Gln Lys Thr Tyr Ser Phe Val Ser
145                 150                 155                 160

Ala Thr Pro Ile Thr Ser Phe Ser Gly Asp Val Met Asp Phe Trp Arg
                165                 170                 175

Tyr Leu Thr Asn Asn His Gly Tyr Pro Ala Ser Ser Gln Tyr Leu Ile
            180                 185                 190

Asn Met Gln Phe Gly Thr Glu Pro Phe Thr Gly Gly Pro Ala Glu Met
        195                 200                 205

Lys Val Ser Lys Phe Thr Ala Ser Val Asn
    210                 215
```

<210> SEQ ID NO 22
<211> LENGTH: 660
<212> TYPE: DNA
<213> ORGANISM: Artificial Sequence
<220> FEATURE:
<223> OTHER INFORMATION: Synthetic Endoglucanase (CL00111817 EG140 G2V1 G3P)

<400> SEQUENCE: 22

```
caaaccctct gtaaccagta tggcacctac agcgaaggcc ggtatacagt caacaacaac     60
ctctggggtc agtcctccgg ctccggctcc caatgcacct acgttgatag catctccaac    120
```

```
tccggcgtgg cgtggcacac gacctggacg tggtctggcg ccctaaccca ggtcaagagc    180
tacgccaact cgcaggtcgc ccttaccaag aagcatgtca gccagatcgg cagtatccca    240
accaccgtgc agtggagcta cgataacacc aacattcgtg cggacgtagc gtacgatctg    300
ttcacagctg cggatatcaa ccatgtaacc tacagcgggg attatgaact gatgatttgg    360
ctcgcccgct acggtaccgt ccagcccatc ggctcgcgga ttggctatgc caatattgcc    420
ggccatacgt gggagctgtg gtacggcggc agtacccaga gacgtacag ctttgtctct     480 gccaccccga tcacctcatt cagtggagat gtcatggact tttggcgcta tctgaccaac    540
aaccatggct accctgcttc gagccagtac ctgatcaata tgcaattcgg gactgagccg    600
ttcactggcg gtcctgccga aatgaaagtg tcgaagttca ctgccagtgt aaactaatag    660
```

<210> SEQ ID NO 23
<211> LENGTH: 218
<212> TYPE: PRT
<213> ORGANISM: Artificial Sequence
<220> FEATURE:
<223> OTHER INFORMATION: Synthetic Endoglucanase (CL00118596 EG140 G3V1 G4P)

<400> SEQUENCE: 23

```
Gln Thr Leu Cys Asn Gln Tyr Gly Thr Tyr Ser Glu Gly Arg Tyr Thr
1               5                   10                  15

Val Asn Asn Asn Leu Trp Gly Gln Ser Ser Gly Ser Gly Ser Gln Cys
            20                  25                  30

Thr Tyr Val Asp Ser Ile Ser Asn Ser Gly Val Ala Trp His Thr Thr
        35                  40                  45

Trp Thr Trp Ser Gly Gly Pro Asn Gln Val Lys Ser Tyr Ala Asn Ser
    50                  55                  60

Gln Val Ala Leu Thr Lys Lys His Val Ser Gln Ile Gly Ser Ile Pro
65                  70                  75                  80

Thr Thr Val Gln Trp Ser Tyr Asp Asn Thr Asn Ile Arg Ala Asp Val
                85                  90                  95

Ala Tyr Asp Leu Phe Thr Ala Ala Asp Ile Asn His Val Thr Tyr Ser
            100                 105                 110

Gly Asp Tyr Glu Leu Met Ile Trp Leu Ala Arg Tyr Gly Thr Val Gln
        115                 120                 125

Pro Ile Gly Ser Arg Ile Gly Tyr Ala Asn Ile Ala Gly His Thr Trp
    130                 135                 140

Glu Leu Trp Tyr Gly Gly Ser Thr Gln Lys Thr Tyr Ser Phe Val Ser
145                 150                 155                 160

Ala Thr Pro Ile Thr Ser Phe Ser Gly Asp Val Met Asp Phe Trp Arg
                165                 170                 175

Tyr Leu Thr Asn Asn His Gly Tyr Pro Ala Ser Ser Gln Tyr Leu Ile
            180                 185                 190

Asn Met Gln Phe Gly Thr Glu Pro Phe Thr Gly Gly Pro Ala Glu Met
        195                 200                 205

Lys Val Ser Asn Phe Thr Ala Ser Val Asn
    210                 215
```

<210> SEQ ID NO 24
<211> LENGTH: 660
<212> TYPE: DNA
<213> ORGANISM: Artificial Sequence
<220> FEATURE:
<223> OTHER INFORMATION: Synthetic Endoglucanase (CL00118596 EG140 G3V1

G4P)

<400> SEQUENCE: 24

```
caaaccctct gtaaccagta tggcacctac agcgaaggcc ggtatacagt caacaacaac      60
ctctggggtc agtcctccgg ctccggctcc caatgcacct acgttgatag catctccaac     120
tccggcgtgg cgtggcacac gacctggacg tggtctggcg gccctaacca ggtcaagagc     180
tacgccaact cgcaggtcgc ccttaccaag aagcatgtca gccagatcgg cagtatccca     240
accaccgtgc agtggagcta cgataacacc aacattcgtg cggacgtagc gtacgatctg     300
ttcacagctg cggatatcaa ccatgtaacc tacagcgggg attatgaact gatgatttgg     360
ctcgcccgct acggtaccgt ccagcccatc ggctcgcgga ttggctatgc caatattgcc     420
ggccatacgt gggagctgtg gtacggcggc agtacccaga agacgtacag ctttgtctct     480
gccaccccga tcacctcatt cagtggagat gtcatggact tttggcgcta tctgaccaac     540
aaccatggct accctgcttc gagccagtac ctgatcaata tgcaattcgg gactgagccg     600
ttcactggcg gtcctgccga aatgaaagtg tcgaacttca ctgccagtgt aaactaatag     660
```

US 10,927,358 B2

ENDOGLUCANASE COMPOSITIONS AND METHODS

CROSS REFERENCE TO RELATED APPLICATIONS

This application claims priority to U.S. Provisional Patent Application No. 62/793,065, filed on Jan. 16, 2019, which is expressly incorporated by reference in its entirety.

SEQUENCE LISTING

The instant application contains a Sequence Listing which has been submitted electronically in ASCII format and is hereby incorporated by reference in its entirety. Said ASCII copy, created on Jan. 13, 2020, is named 114095-5009_ST25.txt and is 34 kilobytes in size.

FIELD OF THE INVENTION

This invention relates to the (variant) endoglucanase enzymes, polynucleotides encoding the (variant) endoglucanase enzymes, methods of producing the (variant) endoglucanase enzymes, and methods of using the (variant) endoglucanase enzymes. Also described are the use of endoglucanases of the invention in the textile, detergent and pulp and paper industries. The invention also relates to compositions comprising one or more (variant) endoglucanases of the invention.

BACKGROUND OF THE INVENTION

Cellulose is the major structural component of higher plants and occurs naturally in almost pure form in cotton fiber. It provides plant cells with high tensile strength helping them to resist mechanical stress and osmotic pressure. Cellulose is a linear polysaccharide of glucose residues connected by β-1,4 linkages.

Cellulolytic enzymes hydrolyze cellulose and are produced by a wide variety of bacteria and fungi. Cellulases are industrially important enzymes. In the textile industry, cellulases are used in denim finishing to create a fashionable stone washed appearance in denim cloths in a biostoning process, and they are also used, for instance, to clean fuzz and prevent formation of pills on the surface of cotton garments. In detergent industry, cellulases are used to brighten colors and to prevent graying and pilling of garments. Cellulases are further used in food industry and animal feed manufacturing, and they have a great potential in the pulp and paper industry, for instance, in deinking to release ink from fiber surfaces and in improving pulp drainage.

Endoglucanases of the present invention mean enzymes classified as E.C. 3.2.1.4 and are one type of cellulases generally needed for the biological conversion of cellulose to glucose. Endoglucanases cut internal beta-1,4-glucosidic bonds, whereas cellobiohydrolases cut the disaccharide cellobiose from the end of the cellulose polymer chain, and beta-1,4-glucosidases hydrolyze the cellobiose and other short cello-oligosaccharides to glucose. Some naturally occurring endoglucanases have a cellulose-binding domain, while others do not. Endoglucanases are also widely used in textile, detergent, and pulp and paper industry. For instance, the endoglucanases as described in U.S. Pat. Nos. 7,256,032, 6,001,639, WO 2004/053039, U.S. Pat. Nos. 5,958,082, 5,948, 672, which are all hereby incorporated by reference in their entireties.

However, there remains a need in the art for variant endoglucanases with increased total activity, specific activity, temperature activity, pH activity, total stability, temperature stability, and pH tolerance. The present invention meets this need and provides variant endoglucanases with improved properties compared to a parent endoglucanase.

It is an object of the present invention to provide (variant) endoglucanase enzymes having endoglucanase activity and polynucleotides encoding the (variant) endoglucanase enzymes and methods of using the (variant) endoglucanase enzymes in various processes.

BRIEF SUMMARY OF THE INVENTION

Accordingly, the present invention provides (variant) endoglucanases and methods of producing and using them. The amino acid sequence numbers and nucleic acid sequence numbers of the present invention are listed in Table 1.

TABLE 1

Amino acid sequence numbers and nucleic acid sequence numbers.

| | |
|---|---|
| EG140 G1P protein | SEQ ID NO: 1 |
| EG140 G1V1 variant protein | SEQ ID NO: 3 |
| EG140 G1V2 variant protein | SEQ ID NO: 5 |
| EG140 G1V3 variant protein | SEQ ID NO: 7 |
| EG185 G1P protein | SEQ ID NO: 9 |
| EG185 G1V1 variant protein | SEQ ID NO: 11 |
| EG185 G1V2 variant protein | SEQ ID NO: 13 |
| EG185 G1V3 variant protein | SEQ ID NO: 15 |
| N.A. encoding EG140 G1P protein | SEQ ID NO: 2 |
| N.A. encoding EG140 G1V1 variant protein | SEQ ID NO: 4 |
| N.A. encoding EG140 G1V2 variant protein | SEQ ID NO: 6 |
| N.A. encoding EG140 G1V3 variant protein | SEQ ID NO: 8 |
| N.A. encoding EG185 G1P protein | SEQ ID NO: 10 |
| N.A. encoding EG185 G1V1 variant protein | SEQ ID NO: 12 |
| N.A. encoding EG185 G1V2 variant protein | SEQ ID NO: 14 |
| N.A. encoding EG185 G1V3 variant protein | SEQ ID NO: 16 |
| EG140 signal peptide | SEQ ID NO: 17 |
| EG185 signal peptide | SEQ ID NO: 18 |
| EG140 G2P variant protein | SEQ ID NO: 19 |
| EG140 G3P variant protein | SEQ ID NO: 21 |
| EG140 G4P variant protein | SEQ ID NO: 23 |
| N.A. encoding EG140 G2P variant protein | SEQ ID NO: 20 |
| N.A. encoding EG140 G3P variant protein | SEQ ID NO: 22 |
| N.A. encoding EG140 G4P variant protein | SEQ ID NO: 24 |

In one aspect, the invention provides a composition comprising a variant endoglucanase enzyme comprising at least one amino acid substitution as compared to SEQ ID NO:1, wherein said amino acid substitution is at a position number selected from the group consisting of 12, 25, 40, 44, 65, 138, 139, 160, 161, 171, 172, 175, 182, 184, 194, 212, 214, 55, 80, 86, 104, 126, 128, 136, 145, 152, 164, 165, 169, 173, 176, 179, 181, 187, 205, 207 and 218, and wherein said variant enzyme is at least 90% identical to SEQ ID NO:1.

In a further aspect, the invention provides a composition comprising a variant endoglucanase enzyme comprising at least one amino acid substitution as compared to SEQ ID NO:1, wherein said amino acid substitution is at a position number selected from the group consisting of 12, 25, 40, 44, 65, 138, 139, 160, 161, 171, 172, 175, 182, 184, 194, 212, 214, 55, 80, 86, 104, 126, 128, 136, 145, 152, 164, 165, 169, 173, 176, 179, 181, 187, 205, 207 and 218, wherein said variant endoglucanase enzyme has at least 1.1 fold better total activity as compared to SEQ ID NO:1 under a condition selected from the group consisting of total activity at about 30° C., total activity at about 40° C., total activity at about 50° C., total activity at about 60° C., and total activity at about 70° C.; and wherein said variant endoglucanase enzyme is at least 90% identical to SEQ ID NO:1.

In an additional aspect, the invention provides a composition comprising a variant endoglucanase enzyme comprising at least one amino acid substitution as compared to SEQ ID NO:1, wherein said amino acid substitution is at a position number selected from the group consisting of 12, 25, 40, 44, 65, 138, 139, 160, 161, 171, 172, 175, 182, 184, 194, 212, 214, 55, 80, 86, 104, 126, 128, 136, 145, 152, 164, 165, 169, 173, 176, 179, 181, 187, 205, 207 and 218, wherein said variant endoglucanase enzyme has at least 1.1 fold better pH tolerance as compared to SEQ ID NO:1 under a condition selected from the group consisting of tolerance against pH 3.0, tolerance against pH 3.5, tolerance against pH 4.0, tolerance against pH 4.5, tolerance against pH 5.0, tolerance against pH 5.5, tolerance against pH 6.0, tolerance against pH 6.5, tolerance against pH 7.0, tolerance against pH 7.5 and tolerance against pH 8.0; and wherein said variant endoglucanase enzyme is at least 90% identical to SEQ ID NO:1.

In a further aspect, the invention provides a composition comprising a variant endoglucanase enzyme comprising at least one amino acid substitution as compared to SEQ ID NO:1 as described herein, wherein said variant endoglucanase enzyme exhibits at least 95%, 96%, 97%, 98%, or 99% identity to SEQ ID NO:1.

In an additional aspect, the invention provides a composition comprising a variant endoglucanase enzyme comprising at least one amino acid substitution as compared to SEQ ID NO:1 as described herein, wherein said amino acid substitution(s) occur at one of said positions, two of said positions, three of said positions, four of said positions, five of said positions, six of said positions, seven of said positions, eight of said positions, nine of said positions, ten of said positions, eleven of said positions or twelve of said positions.

In a further aspect, the invention provides a composition comprising a variant endoglucanase enzyme comprising at least one amino acid substitution as compared to SEQ ID NO:1 as described herein, wherein said amino acid substitution(s) is selected from the group consisting of N12S, G25D, N40S, A44S, Q65G, N138T, I139V, S160A, A161G, V171I, M172K, W175F, H182Q, Y184F, M194L, K212N, T214S, N12D, N12E, N12G, N12T, G25S, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, K212E and N218S.

In an additional aspect, the invention provides a composition comprising a variant endoglucanase enzyme comprising at least one amino acid substitution as compared to SEQ ID NO:1 as described herein, wherein said amino acid substitution(s) is selected from the group consisting of G25D/A161G/M172K/H182Q/M194L/K212N, N12S/G25D/Q65G/S160A/A161G/V171I/Y184F/M194L/K212N, G25D/N138T/V171I/W175F/H182Q/Y184F, G25D/N138T/I139V/M194L, H182Q/K212N, G25D/A161G/T214S, N12S/G25D/A161G/H182Q/Y184F/M194L/K212N/T214S, G25D/N138T/H182Q/K212N, N12S/G25D/A44S/I139V, G25D/N138T/K212N, G25D/V171I/W175F/M194L/K212N, G25D/A161G/K212N, V171I/Y184F, G25D/A44S/A161G, G25D/M172K/H182Q, G25D/A44S/V171I/M172K/H182Q/K212N, G25D/V171I/ M172K/H182Q/M194L, H182Q/M194L, G25D/K212N, N12S/G25D/N138T/A161G/K212N, G25D/H182Q/ Y184F/M194L/K212N, N12S/G25D/N40S/I139V/V171I/ M172K/H182Q/Y184F/M194L/K212N/T214S, N12S/ G25D/H182Q/K212N, G25D/N40S/A44S/N138T/A161G/ V171I/W175F/Y184F/M194L/K212N, N12S/N40S/ Y184F/T214S, N12S/G25D/A44S/Q65G, G25D/A161G/ M194L/T214S, A44S/N138T/I139V/V171I/H182Q/Y184F/ M194L/K212N, G25D/Y184F/M194L/K212N, N12S/ G13P/D55P/M172K/R205P/K212N, N12S/G25D/D55P/ V171I/M172K/S187P, G25D/S187P, G13P/G25D/D55P/ A161P/S187P/R205P/K212N, G25D/D55P, N12S/R133P/ A161P/V171I/S187P/K212N, N12S/G25D, G13P/G25D/ D55P/V171I/S187P/R205P, G13P/G25D/V171I/M172K/ S187P/R205P/K212N, G25D/D55P/R205P, G25D/V171I/ M172K, G25D/R133P, N12S/G25D/V171I/M172K, N12S/ G25D/H182Q/R205P, N12S/G25D/A161P/S187P/K212N, G25D/D55P/V171I/M172K/R205P, D55P/R205P, N12S/ R205P, N12S/G25D/T69P/R133P/V171I/M172K/R205P/ K212N, T179Y/R205Y, N12E/G25D/D55I/G126V/T136M/ T165D/R205P, N12E/G25D/D55I/G126S/T136Y/R205P/ T207E/N218S, N12E/G25S/D55P/N181S/R205P, N12E/ G25D/D55I/P80G/G126I/T136M/R205P, N12E/G25D/ D55P/G126K/E145A/T165D/R205P, N12E/G25D/D55I/ G126T/T136M/T165Y/T179L/R205P, N12E/G25D/D55P/ P80G/G126T/T136Y/T165Y/R205P/T207E, N12E/G25S/ D55P/G126T/R205P/T207E, N12E/G25D/D55P/G126N/ T136Y/T165Y/T179Y/N181S/R205P/T207E, N12E/G25S/ D55P/P80G/G126R/T136Y/R205P, G25D/D55P/G126T/ T165Y/R205P, N12E/G25S/D55I/G126K/T165D/R205P, N12E/G25S/D55P/G126I/T136Y/R205P, G25D/D55P/ G126K/T136Y/T179Y/N181S/R205P, N12E/G25D/D55I/ G126R/R205P, N12E/G25S/D55P/G126N/R205P/T207E, N12E/G25D/D55P/P80G/E145A/R205P/T207E, G25D/ D55P/T136Y/T165Y/R205P/T207E, N12E/G25S/D55P/ G126R/T136Y/T165Y/R205P, N12E/G25D/D55P/P80G/ R205P, G25D/D55I/G126K/R205Y, N12E/G25S/D55P/ G126R/R205P/T207E, G25D/D55P/G126T/T136Y/T165Y/ R205P/N218S, N12E/G25D/D55P/G126N/R205P, N12E/ G25D/D55P/G126K/R205P, N12E/G25D/D55P/T165D/ R205Y, N12E/G25D/D55I/P80G/G126R/R205P/T207E, N12E/G25S/D55P/G126K/T165D/R205P, G25D/D55P/ G126V/T136Y/R205P/T207E, G25D/D55P/T179L/N181S/ R205P/T207E, N12E/G25S/D55P/T165Y/R205P/N218S, N12E/G25D/D55I/G126V/T136M/R205P/N218S, G25S/ D55P/G126R/T136M/E145A/R205P, N12E/G25D/D55I/ G126T/T136M/R205Y, N12E/G25S/D55P/G126V/E145A/ T179Y/R205P, N12E/G25S/D55P/G126T/T165Y/R205P, G25S/D55P/G126R/R205P/N218S, N12E/G25S/D55P/ G126T/T136Y/R205P/T207E, N12E/G25S/D55I/G126R/ T136M/T165Y/R205P/T207E/N218S, N12E/G25S/D55P/ G126S/T136M/T165Y/R205Y, N12D/G25D/D55P/S86A/ E145M/I164T/D173P/R205P/T207E, N12E/G25D/A44D/ D55P/S86H/Q128F/R205P, G25S/D55P/G126I/D173N/ R205P/T207E, N12D/G25S/A44D/D55P/S86Q/T152Q/ R176H/S187N/R205P/K212E, N12D/G25D/A44D/D55P/ Q128R/E145A/D173E/R205P, N12D/G25D/A44D/D55P/ S86A/E145A/R205P/T207E, N12D/G25S/D55P/T136Y/ G169T/R176H/R205P/K212E, N12E/G25D/D55P/S86Q/ A104D/G126T/E145A/D173E/R205P/K212E, G25D/ A44D/D55P/I164T/R205P, N12T/G25D/D55P/S86A/ A104D/Q128R/T165Y/R176H/R205P/K212E/N218S, N12D/G25D/D55P/P80G/S86A/Q128R/I164T/D173E/ R205P/K212E, N12D/G25S/D55P/Q128R/T165Y/R176H/ R205P/K212E, N12G/G25D/A44D/D55P/Q128R/I164T/ D173E/R205P, N12T/G25D/D55P/G126K/E145A/T165D/ D173E/R205P, G25D/A44D/D55P/Q128R/R205P/T207E, G25S/D55P/G126S/T165D/G169S/T179Y/R205P/K212E, G25S/A44D/D55P/P80G/S86A/G126K/Q128R/R205P/

K212E, G25S/D55P/P80G/G126T/R205P, N12T/G25D/ D55I/P80G/G126S/T152Q/S187N/R205P, G25S/D55P/ G126K/T136R/T152Q/R176H/T179Y/R205P/K212E, G25D/D55P/G126T/T165Y/R176H/R205P, N12D/G25D/ D55P/S86Q/A104D/E145A/R205P/T207E/N218S, G25D/ A44D/D55P/A104D/Q128R/E145A/T165D/R176H/ R205P/K212E, G25D/D55P/R205P/K212N, N12E/G25S/ D55R/G126T/T136Y/R205P/T207E, N12E/V17I/G25S/ D55P/G126T/T136Y/R205P/T207E, N12E/G25S/V35I/ D55P/G126T/T136Y/R205P/T207E, N12E/G25S/D55P/ G126T/V127I/T136Y/R205P/T207E, N12E/G25S/G42S/ D55P/G126T/T136Y/R205P/T207E, N12E/G25S/D55P/ Y124F/G126T/T136Y/R205P/T207E, N12E/G25S/D55P/ S78T/G126T/T136Y/R205P/T207E, N12D/G25D/A44D/ D55P/S86Q/G126T/T136Y/R176H/S187N/R205P/T207E, N12T/G25D/D55P/G126T/T136Y/S187N/R205P/T207E/ K212E, N12D/G25D/D55P/G126T/T136Y/R205P/T207E, N12D/G25D/D55P/S86Q/G126T/T136Y/R205P/T207E, N12D/G25S/D55P/S86Q/G126T/T136Y/T165Y/S187N/ R205P/T207E/K212E, N12E/G25S/S28N/D55P/G126T/ T136Y/R205P/T207E, N12E/G25S/S39Y/D55P/G126T/ T136Y/R205P/T207E, N12E/G25S/D55P/G126T/T136Y/ R205P/T207E/K212N, N12T/G25S/A44D/D55P/S86Q/ G126N/T136M/R176H/S187N/R205P/T207E/K212E, N12E/G25D/D55P/G126T/T136Y/S187N/R205P/T207E/ K212E, N12D/G25D/D55P/G126T/T136M/S187N/R205P/ T207E, N12D/G25D/D55P/A104D/G126T/T136Y/S187N/ R205P/T207E/K212E, N12T/G25D/D55P/S86Q/G126T/ T136M/R176H/S187N/R205P/T207E/K212E, N12D/ G25S/A44D/D55P/S86Q/A104D/G126T/T136Y/R205P/ T207E, N12E/G25D/D55P/S86Q/G126T/T136M/D173L/ R176H/R205P/T207E, N12D/G25D/D55P/G126T/T136Y/ R205P/T207E/K212E, N12D/G25D/A44D/D55P/G126T/ T136Y/S187N/R205P/T207E/K212E, N12E/G25D/A44D/ D55P/G126S/T136Y/S187N/R205P/T207E, N12D/G25D/ A44D/D55P/G126T/T136Y/S187N/R205P/T207E, and N12D/G25D/A44D/D55P/S86Q/G126K/T136Y/D173E/ R176H/S187N/R205P/T207E.

In a further aspect, the invention provides a composition comprising a (variant) endoglucanase enzyme as described herein, wherein said endoglucanase enzyme has at least 95% sequence identity to SEQ ID NO:3, SEQ ID NO:5, SEQ ID NO:7, SEQ ID NO:19, SEQ ID NO:21, and SEQ ID NO:23.

In a further aspect, the invention provides a composition comprising a variant endoglucanase enzyme comprising at least one amino acid substitution as compared to SEQ ID NO:1 as described herein, wherein said amino acid substitutions are G25D/A44S/V171I/M172K/H182Q/K212N.

In an additional aspect, the invention provides a composition comprising a variant endoglucanase enzyme comprising at least one amino acid substitution as compared to SEQ ID NO:1 as described herein, wherein said amino acid substitutions are G25D/K212N.

In a further aspect, the invention provides a composition comprising a variant endoglucanase enzyme comprising at least one amino acid substitution as compared to SEQ ID NO:1 as described herein, wherein said amino acid substitutions are N12S/G25D/H182Q/K212N.

In a further aspect, the invention provides a composition comprising a variant endoglucanase enzyme comprising at least one amino acid substitution as compared to SEQ ID NO:1 as described herein, wherein said amino acid substitutions are G25D/D55P/R205P.

In a further aspect, the invention provides a composition comprising a variant endoglucanase enzyme comprising at least one amino acid substitution as compared to SEQ ID NO:1 as described herein, wherein said amino acid substitutions are N12E/G25S/D55P/G126T/T136Y/R205P/T207E.

In a further aspect, the invention provides a composition comprising a variant endoglucanase enzyme comprising at least one amino acid substitution as compared to SEQ ID NO:1 as described herein, wherein said amino acid substitutions are N12E/G25S/D55P/G126T/T136Y/R205P/T207E/K212N.

In a further aspect, the invention provides a composition comprising a variant glucoamylase enzyme as described herein, wherein said composition comprises an amino acid substitution G25D/A44S/V171I/M172K/H182Q/K212N, and further comprises at least one amino acid substitution selected from the group consisting of N12S, N40S, Q65G, N138T, I139V, S160A, A161G, W175F, Y184F, M194L, T214S, N12D, N12E, N12G, N12T, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

In an additional aspect, the invention provides a composition comprising a variant glucoamylase enzyme as described herein, wherein said composition comprises amino acid substitutions G25D/K212N, and further comprises at least one amino acid substitution selected from the group consisting of N12S, N40S, A44S, Q65G, N138T, I139V, S160A, A161G, V171I, M172K, W175F, H182Q, Y184F, M194L, T214S, N12D, N12E, N12G, N12T, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

In an additional aspect, the invention provides a composition comprising a variant glucoamylase enzyme as described herein, wherein said composition comprises amino acid substitutions N12S/G25D/H182Q/K212N, and further comprises at least one amino acid substitution selected from the group consisting of N40S, A44S, Q65G, N138T, I139V, S160A, A161G, V171I, M172K, W175F, Y184F, M194L, T214S, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

In an additional aspect, the invention provides a composition comprising a variant glucoamylase enzyme as described herein, wherein said composition comprises amino acid substitutions G25D/D55P/R205P, and further comprises at least one amino acid substitution selected from the group consisting of N12S, N40S, A44S, Q65G, N138T, I139V, S160A, A161G, V171I, M172K, W175F, H182Q, Y184F, M194L, K212N, T214S, N12D, N12E, N12G, N12T, A44D, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, T207E, K212E, and N218S.

In an additional aspect, the invention provides a composition comprising a variant glucoamylase enzyme as described herein, wherein said composition comprises amino acid substitutions N12E/G25S/D55P/G126T/T136Y/R205P/T207E, and further comprises at least one amino acid substitution selected from the group consisting of N40S, A44S, Q65G, N138T, I139V, S160A, A161G, V171I, M172K, W175F, H182Q, Y184F, M194L, K212N, T214S, A44D, P80G, S86A, S86H, S86Q, A104D, Q128F, Q128R, E145A, E145M, T152Q, I164T, T165D, T165Y, G169S, G169T, D173E, D173N, D173P, R176H, T179L, T179Y, N181S, S187N, K212E, and N218S.

In an additional aspect, the invention provides a composition comprising a variant glucoamylase enzyme as described herein, wherein said composition comprises amino acid substitutions N12E/G25S/D55P/G126T/T136Y/R205P/T207E/K212N, and further comprises at least one amino acid substitution selected from the group consisting of N40S, A44S, Q65G, N138T, I139V, S160A, A161G, V171I, M172K, W175F, H182Q, Y184F, M194L, T214S, A44D, P80G, S86A, S86H, S86Q, A104D, Q128F, Q128R, E145A, E145M, T152Q, I164T, T165D, T165Y, G169S, G169T, D173E, D173N, D173P, R176H, T179L, T179Y, N181S, S187N, and N218S.

In an additional aspect, the invention provides a composition comprising a variant endoglucanase enzyme comprising at least one amino acid substitution as compared to SEQ ID NO:9, wherein said amino acid substitution is at a position number selected from the group consisting of 12, 14, 25, 40, 44, 65, 92, 138, 139, 160, 161, 171, 172, 175, 182, 184, 194, and 212, and wherein said variant enzyme is at least 90% identical to SEQ ID NO:9.

In a further aspect, the invention provides a composition comprising a variant endoglucanase enzyme comprising at least one amino acid substitution as compared to SEQ ID NO:9, wherein said amino acid substitution is at a position number selected from the group consisting of 12, 14, 25, 40, 44, 65, 92, 138, 139, 160, 161, 171, 172, 175, 182, 184, 194, and 212, wherein said variant endoglucanase enzyme has at least 1.1 fold better total activity as compared to SEQ ID NO:9 under a condition selected from the group consisting of total activity at about 30° C., total activity at about 40° C., total activity at about 50° C., total activity at about 60° C., and total activity at about 70° C.; and wherein said variant endoglucanase enzyme is at least 90% identical to SEQ ID NO:9.

In an additional aspect, the invention provides a composition comprising a variant endoglucanase enzyme comprising at least one amino acid substitution as compared to SEQ ID NO:9, wherein said amino acid substitution is at a position number selected from the group consisting of 12, 14, 25, 40, 44, 65, 92, 138, 139, 160, 161, 171, 172, 175, 182, 184, 194, and 212, wherein said variant endoglucanase enzyme has at least 1.1 fold better pH tolerance as compared to SEQ ID NO:9 under a condition selected from the group consisting of tolerance against pH 3.0, tolerance against pH 3.5, tolerance against pH 4.0, tolerance against pH 4.5, tolerance against pH 5.0, tolerance against pH 5.5, tolerance against pH 6.0, tolerance against pH 6.5, tolerance against pH 7.0, tolerance against pH 7.5 and tolerance against pH 8.0; and wherein said variant endoglucanase enzyme is at least 90% identical to SEQ ID NO:9.

In a further aspect, the invention provides the composition comprising a variant endoglucanase enzyme comprising at least one amino acid substitution as compared to SEQ ID NO:9 as described herein, wherein said variant endoglucanase enzyme exhibits at least 95%, 96%, 97%, 98%, or 99% identity to SEQ ID NO:9.

In an additional aspect, the invention provides the composition comprising a variant endoglucanase enzyme comprising at least one amino acid substitution as compared to SEQ ID NO:9 as described herein, wherein said amino acid substitution(s) occur at one of said positions, two of said positions, three of said positions, four of said positions, five of said positions, six of said positions, seven of said positions, eight of said positions, nine of said positions, ten of said positions or eleven of said positions.

In a further aspect, the invention provides the composition comprising a variant endoglucanase enzyme comprising at least one amino acid substitution as compared to SEQ ID NO:9 as described herein, wherein said amino acid substitution(s) is selected from the group consisting of N12S, R14P, S25D, N40S, G44S, Q65G, T92I, S138T, I139V, S160A, A161G, V171I, M172K, W175F, H182Q, Y184F, M194L, and Q212N.

In an additional aspect, the invention provides the composition comprising a variant endoglucanase enzyme comprising at least one amino acid substitution as compared to SEQ ID NO:9 as described herein, wherein said amino acid substitution(s) is selected from the group consisting of N12S/R14P/S25D/T92I, T92I/Y184F, R14P/S25D/T92I/S138T/A161G/M172K/W175F/H182Q/Y184F/Q212N, N12S/I139V, T92I/I139V/H182Q/Y184F, N12S/S25D/T92I/M172K/Y184F/M194L, R14P/S25D/N40S/G44S/S160A/A161G/V171I/Y184F, N12S/S138T/I139V/A161G/M172K/W175F/H182Q/Y184F, S25D/Q65G/T92I/H182Q/Y184F/M194L/Q212N, N12S/R14P/S25D/S138T/S160A/Y184F, N12S/S25D/N40S/G44S/S138T/I139V/H182Q, N12S/R14P/S25D/Q65G/V171I/M172K/W175F/H182Q/Y184F, N12S/R14P/S25D/G44S/T92I/S138T/I139V/S160A/A161G/W175F, S160A/Q212N, N12S/R14P/S25D/S138T/A161G/Y184F, R14P/T92I/A161G/V171I/W175F/Y184F, T92I/A161G/H182Q/Y184F, R14P/A161G/H182Q/Y184F, R14P/S25D/N40S/G44S/S160A/A161G/M172K, N12S/A161G/H182Q/Y184F, N12S/R14P/T92I/A161G/V171I/Y184F, S25D/N40S/T92I/S138T/S160A/A161G/V171I/H182Q/Y184F, R14P/S25D/N40S/G44S, Y184F, N12S/R14P/S25D/T92I/S138T/A161G, N12S/R14P/G44S/T92I/M194L, R14P/S25D/N40S/S138T/Q212N, N12S/S25D/N40S/G44S/Q65G, S25D/G44S/S138T/I139V, S25D/H182Q, R14P/S25D/G44S, N12S/S25D/N40S/G44S/T92I/M172K/H182Q/Q212N, R14P/S25D/N40S/G44S/A161G/V171I/Y184F, N12S/R14P/S25D/A161G/M172K/W175F/Y184F, and N12S/R14P/S25D/N40S/G44S/T92I/I139V.

In a further aspect, the invention provides a composition comprising a (variant) endoglucanase enzyme as described herein, wherein said endoglucanase enzyme has at least 95% sequence identity to SEQ ID NO:11, SEQ ID NO:13, or SEQ ID NO:15.

In a further aspect, the invention provides the composition comprising a variant endoglucanase enzyme comprising at least one amino acid substitution as compared to SEQ ID NO:9 as described herein, wherein said amino acid substitutions are N12S/S25D/T92I/M172K/Y184F/M194L.

In an additional aspect, the invention provides the composition comprising a variant endoglucanase enzyme comprising at least one amino acid substitution as compared to SEQ ID NO:9 as described herein, wherein said amino acid substitutions are S25D/Q65G/T92I/H182Q/Y184F/M194L/Q212N.

In a further aspect, the invention provides the composition comprising a variant endoglucanase enzyme comprising at least one amino acid substitution as compared to SEQ ID NO:9 as described herein, wherein said amino acid substitutions are R14P/S25D/N40S/G44S/S160A/A161G/M172K.

In an additional aspect, the invention provides a nucleic acid encoding said variant endoglucanase enzyme comprising at least one amino acid substitution as compared to SEQ ID NO:1 and SEQ ID NO:9 as described herein.

In a further aspect, the invention provides the nucleic acid encoding said variant endoglucanase enzyme comprising at least one amino acid substitution as compared to SEQ ID NO:1 and SEQ ID NO:9 as described herein, wherein said nucleic acid can be codon optimized for a host organism for expression of the variant endoglucanase enzyme in said organism.

In a further aspect, the invention provides the nucleic acid as described herein, wherein the nucleic acid comprises a sequence that has at least 70% sequence identity to a sequence selected from the group consisting of SEQ ID NO:4, SEQ ID NO:6, SEQ ID NO:8, SEQ ID NO:20, SEQ ID NO:22, and SEQ ID NO:24, SEQ ID NO:12, SEQ ID NO:14 and SEQ ID NO:16.

In an additional aspect, the invention provides the nucleic acid as described herein comprising a sequence selected from the group consisting of SEQ ID NO:4, SEQ ID NO:6, SEQ ID NO:8, SEQ ID NO:20, SEQ ID NO:22, and SEQ ID NO:24, SEQ ID NO:12, SEQ ID NO:14 and SEQ ID NO:16.

In a further aspect, the invention provides an expression vector comprising the nucleic acid as described herein.

In an additional aspect, the invention provides a host cell comprising the nucleic acid as described herein.

In a further aspect, the invention provides a host cell comprising the expression vector as described herein.

In an additional aspect, the invention provides the host cell as described herein, wherein said host cell is selected from the group consisting of a bacterial cell, a fungal cell, and a yeast cell.

In a further aspect, the invention provides a method of making a variant endoglucanase enzyme comprising: a) culturing the host cell as described herein under conditions wherein said variant endoglucanase enzyme is expressed; and b) recovering said variant endoglucanase enzyme.

In an additional aspect, the invention provides a nucleic acid encoding a preprotein comprising a signal peptide and a mature protein, wherein the mature protein is the variant endoglucanase enzyme as described herein.

In a further aspect, the invention provides the nucleic acid as described herein, wherein the signal peptide has SEQ ID NO:17 or SEQ ID NO:18.

In a further aspect, the invention provides the nucleic acid as described herein, wherein the signal peptide is exogenous.

In an additional aspect, the invention provides an expression vector comprising the nucleic acid as described herein.

In a further aspect, the invention provides a host cell comprising the nucleic acid as described herein.

In an additional aspect, the invention provides a host cell comprising the expression vector as described herein.

In a further aspect, the invention provides the host cell as described herein, wherein said host cell is selected from the group consisting of a bacterial cell, a fungal cell, and a yeast cell.

In an additional aspect, the invention provides a method of making a variant endoglucanase enzyme comprising: a) culturing the host cell as described herein under conditions wherein said variant endoglucanase enzyme is expressed; and b) recovering said variant endoglucanase enzyme.

In a further aspect, the invention provides a nucleic acid construct comprising a nucleic acid encoding SEQ ID NO:1 or SEQ ID NO:9 operably linked to an exogenous construct sequence.

In an additional aspect, the invention provides the nucleic acid construct as described herein, wherein the exogenous construct sequence is an exogenous promoter.

In a further aspect, the invention provides the nucleic acid construct as described herein comprising a sequence of SEQ ID NO:2 or SEQ ID NO:10.

In an additional aspect, the invention provides an expression vector comprising the nucleic acid construct as described herein.

In a further aspect, the invention provides a host cell comprising the nucleic acid construct as described herein.

In an additional aspect, the invention provides a host cell comprising the expression vector as described herein.

In a further aspect, the invention provides the host cell as described herein, wherein said host cell is selected from the group consisting of a bacterial cell, a fungal cell, and a yeast cell.

In an additional aspect, the invention provides a method of making an endoglucanase enzyme comprising: a) culturing the host cell as described herein under conditions wherein said endoglucanase enzyme is expressed; and b) recovering said endoglucanase enzyme.

In a further aspect, the invention provides a nucleic acid encoding a preprotein comprising a signal peptide and a mature protein, wherein the preprotein is operably linked to an exogenous promoter, and wherein the mature protein has SEQ ID NO:1 or SEQ ID NO:9.

In an additional aspect, the invention provides the nucleic acid as described herein, wherein the signal peptide has SEQ ID NO:17 or SEQ ID NO:18.

In a further aspect, the invention provides the nucleic acid as described herein, wherein the mature protein has SEQ ID NO:1 and the signal peptide has SEQ ID NO:17.

In an additional aspect, the invention provides the nucleic acid as described herein, wherein the mature protein has SEQ ID NO:9 and the signal peptide has SEQ ID NO:18.

In a further aspect, the invention provides the nucleic acid as described herein, wherein the signal peptide is exogenous.

In an additional aspect, the invention provides an expression vector comprising the nucleic acid as described herein.

In a further aspect, the invention provides a host cell comprising the nucleic acid as described herein.

In an additional aspect, the invention provides a host cell comprising the expression vector as described herein.

In a further aspect, the invention provides the host cell as described herein, wherein said host cell is selected from the group consisting of a bacterial cell, a fungal cell, and a yeast cell.

In an additional aspect, the invention provides a method of making an endoglucanase enzyme comprising: a) culturing the host cell as described herein under conditions wherein said endoglucanase enzyme is expressed; and b) recovering said endoglucanase enzyme.

In a further aspect, the invention provides a method of biostoning comprising the step of contacting the endoglucanase enzyme or the variant endoglucanase enzyme as described herein with cotton-containing fabrics or garments.

In an additional aspect, the invention provides the method of biostoning as described herein, wherein the cotton-containing fabrics or garments are denim.

In a further aspect, the invention provides the method of biofinishing comprising the step of contacting the endoglucanase enzyme or the variant endoglucanase enzyme with a textile material.

In an additional aspect, the invention provides the method of biofinishing as described herein, wherein the textile material is selected from the group consisting of fabrics, garments, and yarn.

In a further aspect, the invention provides a detergent composition comprising the endoglucanase enzyme or the variant endoglucanase enzyme as described herein.

In an additional aspect, the invention provides the detergent composition as described herein further comprising at least one surface active agent and optionally at least one auxiliary ingredient.

In a further aspect, the invention provides a method of treating cellulosic fiber containing textile material(s) comprising contacting said textile material(s) with the detergent composition as described herein.

In an additional aspect, the invention provides a method for treating wood-derived pulp or fiber, comprising the step of contacting the endoglucanase enzyme or the variant endoglucanase enzyme as described herein with wood-derived mechanical or chemical pulp or secondary fiber.

BRIEF DESCRIPTION OF THE DRAWINGS

FIG. 2 shows an amino acid sequence alignment of EG140 and EG185. The Signal Peptide region of EG140 as set forth in SEQ ID NO:17 corresponding to amino acids 1-16 is bold and italicized. Peptide region of EG185 as set forth in SEQ ID NO:18 corresponding to amino acids 1-16 is bold and italicized. Catalytic domain (CD) of EG140 as set forth in SEQ ID NO:1 corresponds to animo acid 30-234. Catalytic domain (CD) of EG185 as set forth in SEQ ID NO:9 corresponds to animo acid 30-234. (Note: numbering starts from the signal peptide region).

FIGS. 3A-3F provide improvement data at pH4.5 and pH 6.5 for EG140 G1 variants. Note: PF is the Performance Factor of G1 variants with respect to (w.r.t.) EG140 G1P (Colony Tracking Number: CL00078795, wild type); AA mutation is the mutations in G1 variants with respect to (w.r.t.) EG140 G1P (Colony Tracking Number: CL00078795, wild type), wherein the numbering starts from the mature region.

FIGS. 4A-4D provide improvement data at pH4.5 and pH 6.5 for EG140 G2 variants. Note: PF is the Performance Factor of G2 variants with respect to (w.r.t.) EG140 G2P (Colony Tracking Number: CL00098799); AA mutation is the mutations in G2 variants with respect to (w.r.t.) EG140 G1P (Colony Tracking Number: CL00078795, wild type), wherein the numbering starts from the mature region.

FIGS. 5A and 5B provide improvement data at pH4.5 and pH 6.5 for EG140 G3 variants. Note: PF is the Performance Factor of G3 variants with respect to (w.r.t.) EG140 G3P (Colony Tracking Number: CL00111817); AA mutation is the mutations in G3 variants with respect to (w.r.t.) EG140 G1P (Colony Tracking Number: CL00078795, wild type), wherein the numbering starts from the mature region.

FIGS. 6A and 6B provide improvement data at pH4.5 and pH 6.5 for EG185 G1 variants. Note: PF is the Performance Factor of G1 variants with respect to (w.r.t.) EG185 G1P (Colony Tracking Number: CL00066590, wild type); AA mutation is the mutations in G1 variants with respect to (w.r.t.) EG185 G1P (Colony Tracking Number: CL00066590, wild type), wherein the numbering starts from the mature region.

FIGS. 7A and 7B provides a summary of EG140 and EG185 G1 variants. As described herein, these may be combined in any combination, and with variants as outlined herein.

FIG. 8A provides the amino acid sequence (SEQ ID NO:1) of EG140 G1P protein, the nucleic acid sequence (SEQ ID NO:2) encoding the EG140 G1P protein, the amino acid sequence (SEQ ID NO:3) of EG140 G1V1 variant protein, the nucleic acid sequence (SEQ ID NO:4) encoding the EG140 G1V1 variant protein, and the amino acid sequence (SEQ ID NO:5) of EG140 G1V2 variant protein. FIG. 8B provides the nucleic acid sequence (SEQ ID NO:6) encoding the EG140 G1V2 variant protein, the amino acid sequence (SEQ ID NO:7) of EG140 G1V3 variant protein, the nucleic acid sequence (SEQ ID NO:8) encoding the EG140 G1V3 variant protein, and the amino acid sequence (SEQ ID NO:9) of EG185 G1P protein. FIG. 8C provides the nucleic acid sequence (SEQ ID NO:10) encoding the EG185 G1P protein, the amino acid sequence (SEQ ID NO:11) of EG185 G1V1 variant protein, the nucleic acid sequence (SEQ ID NO:12) encoding the EG185 G1V1 variant protein, and the amino acid sequence (SEQ ID NO:13) of EG185 G1V2 variant protein. FIG. 8D provides the nucleic acid sequence (SEQ ID NO:14) encoding the EG185 G1V2 variant protein, the amino acid sequence (SEQ ID NO:15) of EG185 G1V3 variant protein, the nucleic acid sequence (SEQ ID NO:16) encoding the EG185 G1V3 variant protein, the amino acid sequence (SEQ ID NO:17) of EG140 signal peptide, and the amino acid sequence (SEQ ID NO:18) of EG185 signal peptide, and the amino acid sequence (SEQ ID NO:19) of EG140 G2P variant protein. FIG. 8E provides the nucleic acid sequence (SEQ ID NO:20) encoding the EG140 G2P variant protein, the amino acid sequence (SEQ ID NO:21) of EG140 G3P variant protein, the nucleic acid sequence (SEQ ID NO:22) encoding the EG140 G3P variant protein, and the amino acid sequence (SEQ ID NO:23) of EG140 G4P variant protein; and FIG. 8F provides the nucleic acid sequence (SEQ ID NO:24) encoding the EG140 G4P variant protein. ** represents double STOP codon TAATAG.

DETAILED DESCRIPTION OF THE INVENTION

I. Introduction

Figure 1:
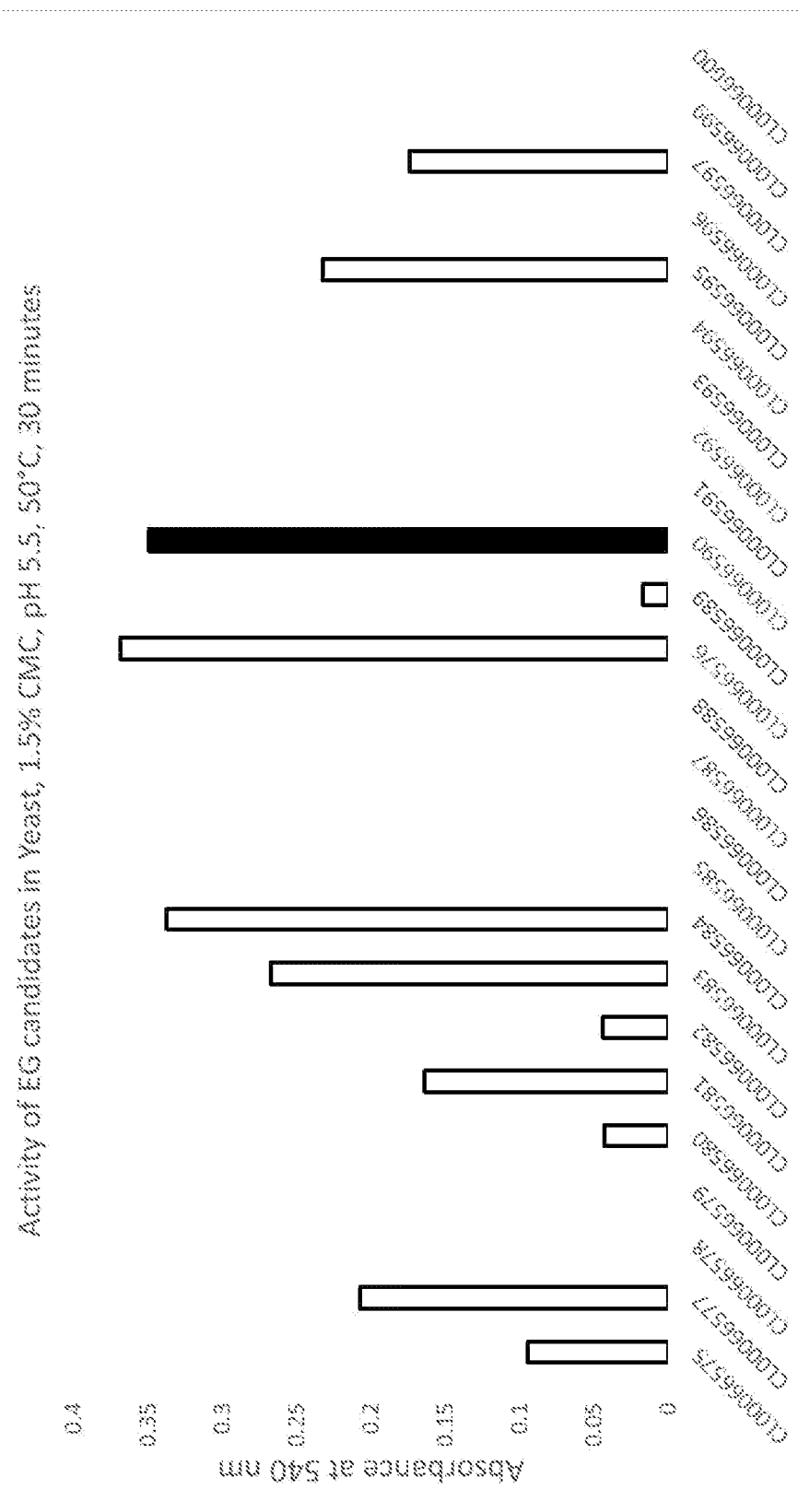
FIG. 1 provides results of evaluation of 25 endoglucanases produced by Saccharomyces cerevisiae in microtiter plate.

In textile industry, "stonewash look" or an abraded look has been an interest of denim producers in recent years. Stone washing has been traditionally achieved by locally removing the indigo dye using a process in which pumice stones are added to the washing drum to abrade the garment. This traditional 'stone-washed' finish on denim fabric reduces the strength of fabric, burdens the laundering machinery and causes pollution in waste water. The trend has been towards an environmental-friendly process, termed as biostoning, which uses enzymes, such as cellulases, to wash/bio-stone denim, producing its desired abraded look without harming the machinery or the environment. Controlled enzyme treatments result in cost saving and improved quality without the need for disposal of stones.

Additionally, textile industry uses cellulases in biofinishing, i.e. to create permanent improvement of depilling and improved pilling resistance, cleared surface structure by reduced fuzz, improved textile handle, such as softness, smoothness and a silkier feel, improved drapability and brighter colors of the textile and improved moisture absorbability.

Endoglucanases, as one type of cellulases are generally needed for the biological conversion of cellulose to glucose, and have a wide range of applications in textile, detergent, and pulp and paper industries.

However, many of the industrial processes that utilize endoglucanases are run under a wide temperature range, e.g. 20-60° C. and a wide pH range, e.g. pH 4-6.5; accordingly, active, temperature and pH stable endoglucanases are desired and provided herein.

II. Definitions

By "exogeneous" in the context of nucleic acid sequences herein is meant that the exogeneous element is not normally associated with the second element in nature and is thus an artificial or synthetic construct. By "exogeneous construct sequence" herein is meant a construct sequence (whether amino acid or nucleic acid sequences, although as will be appreciated by the context in which the term is used, usually refers to the nucleic acid sequence) that is not normally associated with the nucleic acid encoding the endoglucanase. In many embodiments, the invention provides nucleic acid constructs that comprise the coding sequence of an endoglucanase linked to exogeneous construct sequences such as an exogeneous promoter. For clarity, in general the reference to "exogeneous" is in reference to the endoglucanase and not the host cell. For example, if the host cell is an *A. niger* cell, the promoter that is operably linked to the endoglucanase gene may be endogeneous to *A. niger* but exogeneous to the endoglucanase (for example, the promoter from *A. niger* α-amylase can be linked to the endoglucanase of the invention). Accordingly, in some embodiments, the invention provides nucleic acid constructs that encode both an endoglucanase enzyme (whether wild type or variant) operably linked to exogeneous construct nucleic acid sequences. By "exogeneous construct sequence" herein is meant a construct sequence (whether amino acid or nucleic acid sequences, although as will be appreciated by the context in which the term is used, usually refers to the nucleic acid sequence) that is not normally associated with the nucleic acid encoding the endoglucanase.

Suitable construct sequences that can be included in extrachromosomal or integrating expression vectors include, but are not limited to, selectable markers, purification tags, origin(s) of replication and regulatory sequences including but not limited to promoters (inducible and constituative), enhancers, ribosomal binding sites, start codons, termination codons, Shine-Dalgarno sequences, etc.

By "selection marker" or "selectable marker" or "selection protein" herein is meant a protein that is introduced into a host cell that confers a trait suitable for artificial selection during the growth of the host cells, such that only those cells that contain the selectable marker grow. Thus, a selectable marker is a gene the product of which provides for biocide or viral resistance, resistance to heavy metals, prototrophy to auxotrophs, and the like. Examples of selection markers are outlined below. Accordingly, a "selection gene" is a nucleic acid that encodes a selection protein.

By "extrachromosomal expression vector" (also generally referred to as a "plasmid") herein is meant a self-replicating expression vector (generally a plasmid) that carries genes of interest, which remains within the cell and does not integrate into the genome of the host cell.

By "integrating expression vector" herein is meant a vector that is designed to be inserted into the genome of the host cell, sometimes referred to as "episomes".

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution G25D refers to a variant polypeptide, in this case an endoglucanase, in which the glycine at position 25 is replaced with aspartic acid. Multiple mutations are separated by forward slash marks ("/"), e.g., "G25D/N138T/K212N" representing substitutions at positions 25, 138 and 212, respectively (in some cases a "+" can be used). For clarity, a protein which has been engineered to change the nucleic acid coding sequence but not change the starting amino acid (for example, exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233– or E233#, E233( ) or E233del designates a deletion of glutamic acid at position 233. Additionally, EDA233– or EDA233# designates a deletion of the sequence GluAspAla that begins at position 233.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. In the present case, some embodiments utilize EG140 (Colony Tracking Number: CL00078795) or EG185 (Colony Tracking Number: CL00066590) as the parent polypeptide.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about seventy amino acid modifications, and preferably from about one to about eleven amino acid modifications compared to the parent. As described below, in some embodiments the parent polypeptide is a wild type sequence. As further discussed below, the protein variant sequence herein will preferably possess at least about 80% identity with a parent protein sequence, and most preferably at least about 90% identity, more preferably at least about 95-96-97-98-99% identity. Variant protein can refer to the variant protein itself, compositions comprising the protein variant, or the DNA sequence that encodes it. Thus, by "variant endoglucanase" herein is meant a novel endoglucanase that has at least one amino acid modification in the amino acid sequence as compared to a parent endoglucanase enzyme. As discussed herein, in some cases the parent endoglucanase is a second or higher generation of a variant endoglucanase. Unless otherwise noted or as will be obvious from the context, the variant endoglucanases of the invention generally are compared to the G1P sequence (EG140 or EG185). Additionally, unless otherwise noted, the variant endoglucanases of the invention are enzymatically active, that is, there is detectable endoglucanase activity using the endoglucanase assay described in Examples below.

As used herein, "protein" herein is meant at least two covalently attached amino acids, which includes proteins, polypeptides, oligopeptides and peptides. The peptidyl group generally comprise naturally occurring amino acids and peptide bonds. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Glycine 25 (also referred to as Gly25 or G25) is a residue at position 25 in the EG140 G1P parental enzyme.

By "non-naturally occurring modification" as used herein is meant an amino acid modification that is not found in the wild type enzyme.

By "amino acid" and "amino acid identity" as used herein is meant one of the 20 naturally occurring amino acids that are coded for by DNA and RNA.

By "position" as used herein is meant a location in the sequence of a protein. In most cases unless stated otherwise, the position number (which is more fully discussed below) is relative to the first amino acid of the mature endoglucanase sequence, e.g. excluding the signal peptide.

The term "endoglucanases" or called "1,4-β-D-glucan glucanohydrolase" are enzymes classified as E.C. 3.2.1.4 and are one type of cellulases generally needed for the biological conversion of cellulose to glucose. Endoglucanases cut internal beta-1,4-glucosidic bonds, whereas cellobiohydrolases cut the disaccharide cellobiose from the end of the cellulose polymer chain, and beta-1,4-glucosidases hydrolyze the cellobiose and other short cello-oligosaccharides to glucose. Some naturally occurring endoglucanases have a cellulose-binding domain, while others do not. For purposes of the present invention, endoglucanase activity is determined according to the procedures described in the Examples herein, for example, the CMC (carboxymethyl cellulose) Assay to determine endoglucanase activity in Example 3.

The term "biostoning" of fabric or garment means the use of enzymes in place of or in addition to, pumice stones for the treatment of fabric or garment, especially denim, to provide a "stonewash look" or an abraded look. By "stonewash look" or called an "abraded look" or "worn look" is meant, the appearance of fabric or garment, especially denim after it has been treated by cellulase enzymes or stones, or both, which results in contrasts between dyed areas and areas from which dye has been removed due to the treatment for un-even dye removal. In enzymatic stone washing, or biostoning, abrasion with pumice stones is completely or partially eliminated and enzyme is added to facilitate the abrasion of Indigo dye from the fiber surface. The endoglucanases of this invention are especially useful to provide an abraded look and to minimize backstaining in biostoning. The term "backstaining" refers to the tendency of released dye to redeposit on the surface of the fabric fibers. Treatment with endoglucanases of the present invention can completely replace the traditional treatment with pumice stones. However, endoglucanase treatment can be combined with pumice stone treatment when it is desired to produce a heavily abraded finish. By "denim" is meant, in connection of this invention, denim fabric, usually denim garments, particularly jeans. Advantageously, the denim is Indigo dyed denim. Denim can also be treated with Indigo, with derivatives of Indigo or denim dyed with Indigo together with some other dye(s), for example, Indigo-dyed denim with Sulphur bottom.

Biostoning is typically performed at about pH 3.0-8.0, and preferably at pH 4.0-6.5. The temperature of the reaction can range from about 20° C. to 70° C. and is preferably between 45-55° C. or 20-30° C. The liquor ratio (the ratio of the volume of liquid per weight of fabric) may range from about 3:1 to 20:1, preferably 5:1 to 10:1. The treatment time can range between 15 min-90 min and preferably 30 min-60 min. It should be emphasized that the enzyme dosage depends greatly on the type of the fabrics, machinery, process conditions (pH, temperature, liquor ratio, treatment time, denim load, process scale) and type of enzyme preparation and like.

The term "biofinishing" (also called depilling, defuzzing or biopolishing) refers to the use of enzymes in a controlled hydrolysis of cellulosic fibers in order to modify the fabric or yarn surface in a manner that prevents permanently pilling, improves fabric handle like softness and smoothness, clears the surface structure by reducing fuzzing, which results in clarification of colors, improves the drapability of the fabric, improves moisture absorbability, which may improve the dyeability too.

Biofinishing is typically performed at about pH 4.0-6.5. The temperature of the reaction can range from about 20° C. to 70° C., and is preferably 45-60° C. or 20-30° C. The liquor ratio (the ratio of the Volume of liquid per weight of fabric) may range from about 3:1 to 20:1, preferably 5:1 to 10:1. The incubation time is generally 15 to 90 minutes, preferably 30 to 60 min. The enzyme dosage depends greatly on the type of the fabrics, machinery, process conditions (pH, temperature, liquor ratio, treatment time, denim load, process scale) and type of enzyme preparation and like.

The term "coding sequence" refers to a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

The term "detergent" refers to a cleansing agent that can contain surface active agent(s) (anionic, non-ionic, cationic and ampholytic surfactants), and optionally other auxillary ingredient(s) such as anti-redeposition and soil suspension agents, optical brighteners, bleaching agents, dyes and pigments and hydrolases. A suitable listing of the contents of detergents is given in U.S. Pat. No. 5,433,750, hereby incorporated by reference in its entirety. A suitable list of surfactants is given in U.S. Pat. No. 3,664,961, hereby incorporated by reference in its entirety.

The term "control sequences" means nucleic acid sequences necessary for expression of a polynucleotide encoding an endoglucanase of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The term "expression" includes any step involved in the production of a polypeptide, protein or preprotein described herein, including, but not limited to, transcription, post-transcriptional modification, translation, post-translational modification, and secretion.

The term "preprotein" refers to a protein precursor that is an inactive protein or peptide and contains a signal peptide sequence. The preprotein can be turned into a protein in an active form by post-translational modification, such as cleaving off the signal peptide.

The term "expression vector" refers to a linear or circular DNA molecule that comprises a polynucleotide encoding a polypeptide, protein or preprotein as described herein, and is operably linked to control sequences that provide for its expression.

The term "fragment" means a polypeptide having one or more (e.g., several) amino acids absent from the amino and/or carboxyl terminus of a mature polypeptide. A "endoglucanase fragment" herein means a portion of an amino acid sequence depicted herein that maintains endoglucanase activity. In one aspect, an endoglucanase fragment contains at least 50, at least 100, at least 150, at least 200, or at least 210 amino acid residues of a mature endoglucanase polypeptide having zero, one or more of the substitutions according to the invention. In some aspects, a fragment contains the whole or part of the catalytic domain as seen in FIG. 2 having zero, one or more of the substitutions according to the invention.

The term "host cell" refers to any cell type that is susceptible to transformation, transfection, transduction, or the like with a nucleic acid construct or expression vector comprising a polynucleotide of the present invention, and that allows for expression of the enzyme. The term "host cell" encompasses any progeny of a parent cell that is not identical to the parent cell due to mutations that occur during replication. In many embodiments, the endoglucanases of the invention (including both the endoglucanase and variant enzymes described herein) are not produced in the endogeneous host.

The term "improved property" refers to a characteristic associated with a variant endoglucanase enzyme described herein that is improved compared to the parent endoglucanase enzyme. Such improved properties of endoglucanases include, but are not limited to, increased total activity, increased specific activity (e.g. the catalytic activity, its ability to bind to cellulosic materials, and/or its cellulolytic/hydrolytic activity), increased temperature activity (e.g., increased activity at a broad range of temperature), increased pH activity (e.g., increased activity at a broad range of pH), increased total stability, increased temperature stability (e.g., increased stability against a broad range of temperature), and increased pH tolerance (e.g., increased stability against a broad range of pH). Further improved property includes but not limited to improvements in efficiency or effects in fabric treatment and in other fields, where cellulases traditionally are used, for example, increased efficiency or improved effects in biostoning and/or biofinishing process.

The term "isolated" refers to a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance, etc.). With specific reference to isolated endoglucanases of the present invention, the isolated endoglucanase is generally either: a) purified away from other proteins with which it is normally associated; b) when the enzyme is in a concentration not found in nature, or c) when the enzyme is produced in a host cell that is not endogenous.

The term "mature polypeptide" means a polypeptide in its final form following translation and any post-translational modifications, such as N-terminal processing, C-terminal truncation, glycosylation, phosphorylation, etc.

The phrase "mature polypeptide coding sequence" refers to a polynucleotide that encodes a mature polypeptide having endoglucanase activity.

The term "nucleic acid construct" refers to a nucleic acid molecule, either single-stranded or double-stranded, which is isolated from a naturally occurring gene or is modified to contain segments of nucleic acids in a manner that would not otherwise exist in nature or which is synthetic, and which comprises one or more control sequences.

The term "operably linked" refers to a configuration in which a construct sequence is placed at an appropriate position relative to the coding sequence of a polynucleotide such that the control sequence directs, allows or facilitates expression of the coding sequence.

The terms "parent" or "parent endoglucanase" refer to an endoglucanase to which an alteration is made to produce the variant endoglucanases of the present invention. The parent may be a naturally occurring (wild-type) polypeptide or a variant or fragment thereof. An exemplary parent polypeptide of the present invention is SEQ ID NO:1 or SEQ ID NO:9.

The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

The term "subsequence" refers to a polynucleotide having one or more (e.g., several) nucleotides absent from the 5'- and/or 3'-end of a mature polypeptide coding sequence; wherein the subsequence encodes a fragment having endoglucanase activity. In one aspect, a subsequence encodes at least the catalytic domain of the endoglucanase enzyme as seen in FIG. 2 having zero, one or more of the substitutions according to the invention.

The term "variant" refers to a polypeptide having endoglucanase activity and which comprises an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

The term "wild-type" endoglucanase refers to the sequence of the typical form of an endoglucanase as it occurs in a naturally occurring microorganism, such as a bacterium, yeast, or filamentous fungus found in nature.

III. Endoglucanases of the Invention

The invention provides thermoactive, thermostable and/or pH stable and active endoglucanases for use in a variety of applications, including in the textile, detergent and pulp and paper industries. The invention provides compositions and methods using an endoglucanase having SEQ ID NO:1 or SEQ ID NO:9, as well as variants thereof, as more fully described below.

IV. Variant Endoglucanases of the Invention

Accordingly, the present invention provides variant endoglucanases with improved properties that can be used in a variety of applications, including in the textile, detergent and pulp and paper industries.

In general, the variant endoglucanases of the invention have modified, improved biochemical properties as compared to the parental endoglucanases, or "G1P" (e.g. EG140 G1P as set forth in SEQ ID NO:1 or EG185 G1P as set forth in SEQ ID NO:9 herein, as shown in FIG. 8). The biochemical properties of the variant endoglucanases that can be improved herein include, but are not limited to, total activity, specific activity, temperature activity, pH activity, total stability, temperature stability, pH tolerance, formulation stability (including liquid, solid and pellets), protease stability, performance in the processes of biostoning, biofinishing, etc.

The variant endoglucanases of the invention have one or more improved properties as compared to G1P. By "improved" herein is meant a desirable change of at least one biochemical property. "Improved function" can be measured as a percentage increase or decrease of a particular activity, or as a "fold" change, with increases of desirable properties (e.g. total activity and pH tolerance) or decreases of undesirable properties (e.g. protease sensitivity). That is, a variant endoglucanase may have a 10% increase in total activity or a 10% decrease in protease sensitivity, as compared to G1P. Alternatively, a variant endoglucanase may have a 2-fold increase in pH tolerance or a 3-fold decrease in protease sensitivity. In general, percentage changes are used to describe changes in biochemical activity of less than 100%, and fold-changes are used to describe changes in biochemical activity of greater than 100% (as compared to the parental enzyme, in many cases G1P). In the present invention, percentage changes (usually increases) of biochemical activity of at least about 10%, 20%, 30%, 40%, 50%, 60%, 70%, 80%, 90%, 95%, 98% and 99% can be accomplished. In the present invention, a "fold increase" (or decrease) is measured as compared to the starting or parent enzyme. For example, as shown in the FIG. 3A, EG140 G1V1 has a 1.36 fold increase in total activity and pH tolerance improvements as compared to EG140 G1P: this is calculated by [(activity of variant)/(activity of parent)]. In many embodiments, the improvement is at least one and a tenth fold (1.1), one and a half fold (1.5 fold), 2 fold, 3 fold, 4 fold, 5 fold, 6 fold, 7 fold, 8 fold, 9 fold, or 10 fold or higher.

The variant endoglucanases of the invention can have an improvement in one or more of a number of biochemical properties, including, but not limited to, total activity, specific activity, temperature activity, pH activity, total stability, temperature stability, pH tolerance, formulation stability (including liquid, solid and pellets), protease stability, performance in the processes of biostoning, biofinishing, etc. In general, improvements are measured as compared to the G1P enzyme using an endoglucanase activity assay, as outlined below.

A. CMC Assay to Determine Total Activity

In some embodiments, a CMC assay is employed to determine endoglucanase total activity, such as the one described in the Examples section. Specifically, Into PCR plate, 50 μL of 1.8% low viscosity carboxymethyl cellulose (CMC) dissolved in 100 mM sodium acetate, pH5.5 buffer (Catalog #C5678) is added into a plate. Then 10 μL of supernatant enzyme is added into the same plate and shaked on bench top shaker for ~1 minute. The plate is then incubated at 50° C. for 30 minutes and centrifuged at 4,000 rpm for 2 minutes. 90 μL of DNS solution is added into the plate and the plates is sealed. Place the plate into Thermocycler and select "95DNS" program with NO heated lid option and with the "95DNS" program settings: at 95° C. for 5 minutes and cool to 4° C. for 2 minutes. After incubation, overturn plates a few times and centrifuge plates for 3 minutes at 4,000 rpm. Into clear bottom plates, add 100 μL of water and transfer 100 μL of DNS reaction. The plate is shaked and read at 540 nm for endoglucanase activity. Activity of an endoglucanase variant is compared to the parent endoglucanase enzyme under the same conditions to determine total activity improvement at 50° C. (generally using the endoglucanase assay as shown in Examples 6 and 7). In some embodiments, the parent endoglucanase enzyme is a polypeptide of SEQ ID NO:1 or SEQ ID NO:9.

Accordingly, as shown in the FIGS. 3, 4, 5 and 6, a number of variant endoglucanases of the invention exhibit increased total activity at pH4.5, 50° C. and/or pH6.5, 50° C.

B. pH Tolerance

In many embodiments, the variant endoglucanases of the invention have altered pH tolerance as compared to the parent endoglucanase. "Increased pH tolerance" in this context means that the variant enzymes are more stable than the parent endoglucanases (e.g. G1P) under the same pH challenge conditions, that is, the activity of the variant is higher than that of the G1P under identical conditions (generally using the endoglucanase assay as shown in Examples 6 and 7). For example, biostoning or biofinishing processing can be done at a variety of pHs, depending on the raw substrates and reaction conditions.

Taken together, the variant endoglucanases of the invention can exhibit increased tolerance to pH 6.5 as compared to SEQ ID NO:1 or SEQ ID NO:9 at 50° C. for a period, generally ranging from about 10 minutes to 3 hours.

Accordingly, as shown in the FIGS. 3, 4, 5 and 6, a number of variant endoglucanases of the invention exhibited increased tolerance against pH 6.5 at 50° C.

C. Thermostability

In many embodiments, the variant endoglucanases of the invention have increased thermostability, particularly under the high temperature conditions used in the biostoning or biofinishing process. "Thermostability" in this context means that the variant enzymes are more stable than the parent endoglucanase (e.g. G1P) under the same thermal challenge conditions, that is, the activity of the variant is higher than that of the G1P under identical conditions (generally using the endoglucanase assay as outlined herein).

A suitable thermostability assay is as follows. 50 µl of the enzymes from the lysate plates are added to 96 well Biorad PCR plates and are challenged from 30-70° C. for 10 minutes. The control reaction was placed at room temperature for the same amount of time. Following the thermal challenge, the residual activity was determined using the control reaction. Activity of endoglucanase variant is compared to the parent under the same conditions to determine thermostability improvement.

Taken together, the variant endoglucanases of the invention can exhibit increased thermostability as compared to SEQ ID NO:1 or SEQ ID NO:9 at 30° C., 40° C., 45° C., 50° C., 55° C., 58° C., 60° C., 65° C., 66° C., 70° C., 75° C., 80° C. and/or 85° C. for a period of time, generally ranging from about 10 minutes to 3 hours.

D. Specific Activity Assays

In some embodiments, the variant endoglucanases of the invention have increased specific activity as compared to a parent endoglucanase, particularly G1P. By "specific activity" herein is meant the activity per amount of enzyme, generally determined by dividing the enzymatic activity of a sample (sometimes measured in "endoglucanase units") by the amount of endoglucanase enzyme, generally determined as is known in the art.

E. Protease Susceptibility

In some embodiments, the variant endoglucanases of the invention are less susceptible to protease degradation than the parent enzyme under identical conditions. In some cases, protease degradation during the production of variant endoglucanases in a production host organism by protease enzymes produced by the host organism can be a problem, thus resulting in lower yield of active enzyme. Similarly, depending on the use of the variant enzymes, there may be other proteases present in the raw substrates or other enzymes for use in combination that can degrade the endoglucanases.

This is generally determined as is known in the art, for example by allowing proteolytic degradation and then doing N-terminal sequencing on the resulting fragments to determine the cleavage site(s). In some cases, depending on the variant and the host production organism, there may not be significant proteolytic degradation.

As needed, as will be appreciated by those in the art, the specific mutations that can be made will depend on the endogenous proteases that the host organism produces, and also generally occurs in surface exposed loop structures or turns that are therefore accessible to proteases.

V. Specific Variant Endoglucanases

The present invention provides variant endoglucanase enzymes comprising one or more amino acid substitutions at one or more (e.g., several) positions corresponding to positions 12, 14, 25, 40, 44, 65, 92, 138, 139, 160, 161, 171, 172, 175, 182, 184, 194, 212, 214, 55, 80, 86, 104, 126, 128, 136, 145, 152, 164, 165, 169, 173, 176, 179, 181, 187, 205, 207 and/or 218 as compared to a parent endoglucanase enzyme. In some cases, the variant enzyme can comprise 1, 2, 3, 4, 5, 6, 7, 8, 9, 10, 11, 12, 13, 14, 15, 16, 17, 18, or 19 amino acid substitutions at these positions. In some embodiments, the variant exhibits at least 85%, at least 90%, at least 95%, at least 96%, at least 97%, at least 98%, or at least 99%, but less than 100% sequence identity to the parent endoglucanase enzyme. In some embodiments, the variant endoglucanase exhibits at least 95%, 96%, 97%, 98% or 99% but less than 100% sequence identity to the parent endoglucanase enzyme. In one embodiment, the parent endoglucanase enzyme is SEQ ID NO:1. In another embodiment, the parent endoglucanase enzyme is SEQ ID NO:9.

In some embodiments, the variant endoglucanase enzyme comprises at least one amino acid substitution as compared to SEQ ID NO:1, wherein said amino acid substitution is at a position number selected from the group consisting of 12, 25, 40, 44, 65, 138, 139, 160, 161, 171, 172, 175, 182, 184, 194, 212, 214, 55, 80, 86, 104, 126, 128, 136, 145, 152, 164, 165, 169, 173, 176, 179, 181, 187, 205, 207 and 218, and wherein said variant enzyme is at least 90% identical to SEQ ID NO:1.

In some embodiments, the variant endoglucanase enzyme comprises at least one amino acid substitution as compared to SEQ ID NO:9, wherein said amino acid substitution is at a position number selected from the group consisting of 12, 14, 25, 40, 44, 65, 92, 138, 139, 160, 161, 171, 172, 175, 182, 184, 194, and 212, and wherein said variant enzyme is at least 90% identical to SEQ ID NO:9.

In some embodiments, the variant endoglucanase enzyme comprises at least one amino acid substitution as compared to SEQ ID NO:1, wherein said amino acid substitution is at a position number selected from the group consisting of 12, 25, 40, 44, 65, 138, 139, 160, 161, 171, 172, 175, 182, 184, 194, 212, 214, 55, 80, 86, 104, 126, 128, 136, 145, 152, 164, 165, 169, 173, 176, 179, 181, 187, 205, 207 and 218, wherein said variant endoglucanase enzyme has at least 1.1 fold better activity as compared to SEQ ID NO:1 under a condition selected from the group consisting of total activity at about 30° C., total activity at about 40° C., total activity at about 50° C., total activity at about 60° C., total activity at about 70° C.; and wherein said variant endoglucanase enzyme is at least 90% identical to SEQ ID NO:1.

In some embodiments, the variant endoglucanase enzyme comprises at least one amino acid substitution as compared to SEQ ID NO:1, wherein said amino acid substitution is at a position number selected from the group consisting of 12, 25, 40, 44, 65, 138, 139, 160, 161, 171, 172, 175, 182, 184, 194, 212, 214, 55, 80, 86, 104, 126, 128, 136, 145, 152, 164, 165, 169, 173, 176, 179, 181, 187, 205, 207 and 218, wherein said variant endoglucanase enzyme has at least 1.1 fold better activity as compared to SEQ ID NO:1 under a condition selected from the group consisting of tolerance against pH 3.0, tolerance against pH 3.5, tolerance against pH 4.0, tolerance against pH 4.5, tolerance against pH 5.0, tolerance against pH 5.5, tolerance against pH 6.0, tolerance against pH 6.5, tolerance against pH 7.0, tolerance against pH 7.5 and tolerance against pH 8.0; and wherein said variant endoglucanase enzyme is at least 90% identical to SEQ ID NO:1.

In some embodiments, the variant endoglucanase enzyme comprises at least one amino acid substitution as compared to SEQ ID NO:9, wherein said amino acid substitution is at a position number selected from the group consisting of 12, 14, 25, 40, 44, 65, 92, 138, 139, 160, 161, 171, 172, 175, 182, 184, 194, and 212, wherein said variant endoglucanase enzyme has at least 1.1 fold better activity as compared to SEQ ID NO:9 under a condition selected from the group consisting of total activity at about 30° C., total activity at about 40° C., total activity at about 50° C., total activity at about 60° C., and total activity thermostability at about 70° C.; and wherein said variant endoglucanase enzyme is at least 90% identical to SEQ ID NO:9.

In some embodiments, the variant endoglucanase enzyme comprises at least one amino acid substitution as compared to SEQ ID NO:9, wherein said amino acid substitution is at a position number selected from the group consisting of 12, 14, 25, 40, 44, 65, 92, 138, 139, 160, 161, 171, 172, 175, 182, 184, 194, and 212, wherein said variant endoglucanase enzyme has at least 1.1 fold better activity as compared to SEQ ID NO:9 under a condition selected from the group consisting of tolerance against pH 3.0, tolerance against pH 3.5, tolerance against pH 4.0, tolerance against pH 4.5, tolerance against pH 5.0, tolerance against pH 5.5, tolerance against pH 6.0, tolerance against pH 6.5, tolerance against pH 7.0, tolerance against pH 7.5 and tolerance against pH 8.0; and wherein said variant endoglucanase enzyme is at least 90% identical to SEQ ID NO:9.

In some embodiments, the variant endoglucanase enzyme comprises at least one amino acid substitution as compared to a parent endoglucanase enzyme, wherein said amino acid substitution(s) occur at one of said positions, two of said positions, three of said positions, four of said positions, five of said positions, six of said positions, seven of said positions, eight of said positions, nine of said positions, ten of said positions, eleven of said positions or twelve of said positions. In one embodiment, the parent endoglucanase enzyme is SEQ ID NO:1. In another embodiment, the parent endoglucanase enzyme is SEQ ID NO:9.

In some embodiments, the variant endoglucanase enzyme comprises at least one amino acid substitution as compared to SEQ ID NO:1, wherein said amino acid substitution is selected from the group consisting of N12S, G25D, N40S, A44S, Q65G, N138T, I139V, S160A, A161G, V171I, M172K, W175F, H182Q, Y184F, M194L, K212N, T214S, N12D, N12E, N12G, N12T, G25S, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, K212E and N218S.

In some embodiments, the variant endoglucanase enzyme comprises at least one amino acid substitution as compared to SEQ ID NO:1, wherein said amino acid substitution(s) is selected from the group consisting of G25D/A161G/M172K/H182Q/M194L/K212N, N12S/G25D/Q65G/S160A/A161G/V171I/Y184F/M194L/K212N, G25D/N138T/V171I/W175F/H182Q/Y184F, G25D/N138T/I139V/M194L, H182Q/K212N, G25D/A161G/T214S, N12S/G25D/A161G/H182Q/Y184F/M194L/K212N/T214S, G25D/N138T/H182Q/K212N, N12S/G25D/A44S/I139V, G25D/N138T/K212N, G25D/V171I/W175F/M194L/K212N, G25D/A161G/K212N, V171I/Y184F, G25D/A44S/A161G, G25D/M172K/H182Q, G25D/A44S/V171I/M172K/H182Q/K212N, G25D/V171I/M172K/H182Q/M194L, H182Q/M194L, G25D/K212N, N12S/G25D/N138T/A161G/K212N, G25D/H182Q/Y184F/M194L/K212N, N12S/G25D/N40S/I139V/V171I/M172K/H182Q/Y184F/M194L/K212N/T214S, N12S/G25D/H182Q/K212N, G25D/N40S/A44S/N138T/A161G/V171I/W175F/Y184F/M194L/K212N, N12S/N40S/Y184F/T214S, N12S/G25D/A44S/Q65G, G25D/A161G/M194L/T214S, A44S/N138T/I139V/V171I/H182Q/Y184F/M194L/K212N, G25D/Y184F/M194L/K212N, N12S/G13P/D55P/M172K/R205P/K212N, N12S/G25D/D55P/V171I/M172K/S187P, G25D/S187P, G13P/G25D/D55P/A161P/S187P/R205P/K212N, G25D/D55P, N12S/R133P/A161P/V171I/S187P/K212N, N12S/G25D, G13P/G25D/D55P/V171I/S187P/R205P, G13P/G25D/V171I/M172K/S187P/R205P/K212N, G25D/D55P/R205P, G25D/V171I/M172K, G25D/R133P, N12S/G25D/V171I/M172K, N12S/G25D/H182Q/R205P, N12S/G25D/A161P/S187P/K212N, G25D/D55P/V171I/M172K/R205P, D55P/R205P, N12S/R205P, N12S/G25D/T69P/R133P/V171I/M172K/R205P/K212N, T179Y/R205Y, N12E/G25D/D55I/G126V/T136M/T165D/R205P, N12E/G25D/D55I/G126S/T136Y/R205P/T207E/N218S, N12E/G25S/D55P/N181S/R205P, N12E/G25D/D55I/P80G/G126I/T136M/R205P, N12E/G25D/D55P/G126K/E145A/T165D/R205P, N12E/G25D/D55I/G126T/T136M/T165Y/T179L/R205P, N12E/G25S/D55P/P80G/G126T/T136Y/T165Y/R205P/T207E, N12E/G25S/D55P/G126T/R205P/T207E, N12E/G25D/D55P/G126N/T136Y/T165Y/T179Y/N181S/R205P/T207E, N12E/G25S/D55P/P80G/G126R/T136Y/R205P, G25D/D55P/G126T/T165Y/R205P, N12E/G25S/D55I/G126K/T165D/R205P, N12E/G25S/D55P/G126I/T136Y/R205P, G25D/D55P/G126K/T136Y/T179Y/N181S/R205P, N12E/G25D/D55I/G126R/R205P, N12E/G25S/D55P/G126N/R205P/T207E, N12E/G25D/D55P/P80G/E145A/R205P/T207E, G25D/D55P/T136Y/T165Y/R205P/T207E, N12E/G25S/D55P/G126R/T136Y/T165Y/R205P, N12E/G25D/D55P/P80G/R205P, G25D/D55I/G126K/R205Y, N12E/G25S/D55P/G126R/R205P/T207E, G25D/D55P/G126T/T136Y/T165Y/R205P/N218S, N12E/G25D/D55P/G126N/R205P, N12E/G25D/D55P/G126K/R205P, N12E/G25D/D55P/T165D/R205Y, N12E/G25D/D55I/P80G/G126R/R205P/T207E, N12E/G25S/D55P/G126K/T165D/R205P, G25D/D55P/G126V/T136Y/R205P/T207E, G25D/D55P/T179L/N181S/R205P/T207E, N12E/G25S/D55P/T165Y/R205P/N218S, N12E/G25D/D55I/G126V/T136M/R205P/N218S, G25D/D55P/G126R/T136M/E145A/R205P, N12E/G25D/D55I/G126T/T136M/R205Y, N12E/G25S/D55P/G126V/E145A/T179Y/R205P, N12E/G25S/D55P/G126T/T165Y/R205P, G25S/D55P/G126R/R205P/N218S, N12E/G25S/D55P/G126T/T136Y/R205P/T207E, N12E/G25S/D55I/G126R/T136M/T165Y/R205P/T207E/N218S, N12E/G25S/D55P/G126S/T136M/T165Y/R205Y, N12D/G25D/D55P/S86A/E145M/I164T/D173P/R205P/T207E, N12E/G25D/A44D/D55P/S86H/Q128F/R205P, G25S/D55P/G126I/D173N/R205P/T207E, N12D/G25S/A44D/D55P/S86Q/T152Q/R176H/S187N/R205P/K212E, N12D/G25D/A44D/D55P/Q128R/E145A/D173E/R205P, N12D/G25D/A44D/D55P/S86A/E145A/R205P/T207E, N12D/G25S/D55P/T136Y/G169T/R176H/R205P/K212E, N12E/G25D/D55P/S86Q/A104D/G126T/E145A/D173E/R205P/K212E, G25D/A44D/D55P/I164T/R205P, N12T/G25D/D55P/S86A/A104D/Q128R/T165Y/R176H/R205P/K212E/N218S, N12D/G25D/D55P/P80G/S86A/Q128R/I164T/D173E/R205P/K212E, N12D/G25S/D55P/Q128R/T165Y/R176H/R205P/K212E, N12G/G25D/A44D/D55P/Q128R/I164T/D173E/R205P, N12T/G25D/

D55P/G126K/E145A/T165D/D173E/R205P, G25D/A44D/ D55P/Q128R/R205P/T207E, G25S/D55P/G126S/T165D/ G169S/T179Y/R205P/K212E, G25S/A44D/D55P/P80G/ S86A/G126K/Q128R/R205P/K212E, G25S/D55P/P80G/ G126T/R205P, N12T/G25D/D55I/P80G/G126S/T152Q/ S187N/R205P, G25S/D55P/G126K/T136R/T152Q/R176H/ T179Y/R205P/K212E, G25D/D55P/G126T/T165Y/ R176H/R205P, N12D/G25D/D55P/S86Q/A104D/E145A/ R205P/T207E/N218S, G25D/A44D/D55P/A104D/Q128R/ E145A/T165D/R176H/R205P/K212E, G25D/D55P/R205P/ K212N, N12E/G25S/D55R/G126T/T136Y/R205P/T207E, N12E/V17I/G25S/D55P/G126T/T136Y/R205P/T207E, N12E/G25S/V35I/D55P/G126T/T136Y/R205P/T207E, N12E/G25S/D55P/G126T/V127I/T136Y/R205P/T207E, N12E/G25S/G42S/D55P/G126T/T136Y/R205P/T207E, N12E/G25S/D55P/Y124F/G126T/T136Y/R205P/T207E, N12E/G25S/D55P/S78T/G126T/T136Y/R205P/T207E, N12D/G25D/A44D/D55P/S86Q/G126T/T136Y/R176H/ S187N/R205P/T207E, N12T/G25D/D55P/G126T/T136Y/ S187N/R205P/T207E/K212E, N12D/G25D/D55P/G126T/ T136Y/R205P/T207E, N12D/G25D/D55P/S86Q/G126T/ T136Y/R205P/T207E, N12D/G25S/D55P/S86Q/G126T/ T136Y/T165Y/S187N/R205P/T207E/K212E, N12E/G25S/ S28N/D55P/G126T/T136Y/R205P/T207E, N12E/G25S/ S39Y/D55P/G126T/T136Y/R205P/T207E, N12E/G25S/ D55P/G126T/T136Y/R205P/T207E/K212N, N12T/G25S/ A44D/D55P/S86Q/G126N/T136M/R176H/S187N/R205P/ T207E/K212E, N12E/G25D/D55P/G126T/T136Y/S187N/ R205P/T207E/K212E, N12D/G25D/D55P/G126T/T136M/ S187N/R205P/T207E, N12D/G25D/D55P/A104D/G126T/ T136Y/S187N/R205P/T207E/K212E, N12T/G25D/D55P/ S86Q/G126T/T136M/R176H/S187N/R205P/T207E/ K212E, N12D/G25S/A44D/D55P/S86Q/A104D/G126T/ T136Y/R205P/T207E, N12E/G25D/D55P/S86Q/G126T/ T136M/D173L/R176H/R205P/T207E, N12D/G25D/D55P/ G126T/T136Y/R205P/T207E/K212E, N12D/G25D/A44D/ D55P/G126T/T136Y/S187N/R205P/T207E/K212E, N12E/ G25D/A44D/D55P/G126S/T136Y/S187N/R205P/T207E, N12D/G25D/A44D/D55P/G126T/T136Y/S187N/R205P/ T207E, and N12D/G25D/A44D/D55P/S86Q/G126K/ T136Y/D173E/R176H/S187N/R205P/T207E.

In some embodiments, the variant endoglucanase enzyme comprises at least one amino acid substitution as compared to SEQ ID NO:1, wherein said amino acid substitutions are G25D/A44S/V171I/M172K/H182Q/K212N.

In some embodiments, the variant endoglucanase enzyme comprises at least one amino acid substitution as compared to SEQ ID NO:1, wherein said amino acid substitutions are G25D/K212N.

In some embodiments, the variant endoglucanase enzyme comprises at least one amino acid substitution as compared to SEQ ID NO:1, wherein said amino acid substitutions are N12S/G25D/H182Q/K212N.

In some embodiments, the variant endoglucanase enzyme comprises at least one amino acid substitution as compared to SEQ ID NO:1, wherein said amino acid substitutions are G25D/D55P/R205P.

In some embodiments, the variant endoglucanase enzyme comprises at least one amino acid substitution as compared to SEQ ID NO:1, wherein said amino acid substitutions are N12E/G25S/D55P/G126T/T136Y/R205P/T207E.

In some embodiments, the variant endoglucanase enzyme comprises at least one amino acid substitution as compared to SEQ ID NO:1, wherein said amino acid substitutions are N12E/G25S/D55P/G126T/T136Y/R205P/T207E/K212N.

In some embodiments, the invention provides a variant glucoamylase enzyme as described herein, wherein said amino acid substitutions comprise G25D/A44S/V171I/M172K/H182Q/K212N, and further comprise at least one amino acid selected from the group consisting of N12S, N40S, Q65G, N138T, I139V, S160A, A161G, W175F, Y184F, M194L, T214S, N12D, N12E, N12G, N12T, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

In some embodiments, the invention provides a variant glucoamylase enzyme as described herein, wherein said amino acid substitutions comprise G25D/K212N, and further comprise at least one amino acid selected from the group consisting of N12S, N40S, A44S, Q65G, N138T, I139V, S160A, A161G, V171I, M172K, W175F, H182Q, Y184F, M194L, T214S, N12D, N12E, N12G, N12T, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

In some embodiments, the invention provides a variant glucoamylase enzyme as described herein, wherein said amino acid substitutions comprise N12S/G25D/H182Q/K212N, and further comprise at least one amino acid selected from the group consisting of N40S, A44S, Q65G, N138T, I139V, S160A, A161G, V171I, M172K, W175F, Y184F, M194L, T214S, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

In some embodiments, the invention provides a variant glucoamylase enzyme as described herein, wherein said amino acid substitutions comprise G25D/D55P/R205P, and further comprise at least one amino acid selected from the group consisting of N12S, N40S, A44S, Q65G, N138T, I139V, S160A, A161G, V171I, M172K, W175F, H182Q, Y184F, M194L, K212N, T214S, N12D, N12E, N12G, N12T, A44D, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, T207E, K212E, and N218S.

In some embodiments, the invention provides a variant glucoamylase enzyme as described herein, wherein said amino acid substitutions comprise N12E/G25S/D55P/G126T/T136Y/R205P/T207E, and further comprise at least one amino acid selected from the group consisting of N40S, A44S, Q65G, N138T, I139V, S160A, A161G, V171I, M172K, W175F, H182Q, Y184F, M194L, K212N, T214S, A44D, P80G, S86A, S86H, S86Q, A104D, Q128F, Q128R, E145A, E145M, T152Q, I164T, T165D, T165Y, G169S, G169T, D173E, D173N, D173P, R176H, T179L, T179Y, N181S, S187N, K212E, and N218S.

In some embodiments, the invention provides a variant glucoamylase enzyme as described herein, wherein said amino acid substitutions comprise N12E/G25S/D55P/G126T/T136Y/R205P/T207E/K212N, and further comprise at least one amino acid selected from the group consisting of N40S, A44S, Q65G, N138T, I139V, S160A, A161G, V171I, M172K, W175F, H182Q, Y184F, M194L, T214S, A44D, P80G, S86A, S86H, S86Q, A104D, Q128F, Q128R, E145A, E145M, T152Q, I164T, T165D, T165Y, G169S, G169T, D173E, D173N, D173P, R176H, T179L, T179Y, N181S, S187N, and N218S.

In some embodiments, the variant endoglucanase enzyme comprises at least one amino acid substitution as compared to SEQ ID NO:9, wherein said amino acid substitution is selected from the group consisting of N12S, R14P, S25D, N40S, G44S, Q65G, T92I, S138T, I139V, S160A, A161G, V171I, M172K, W175F, H182Q, Y184F, M194L, and Q212N.

In some embodiments, the variant endoglucanase enzyme comprises at least one amino acid substitution as compared to SEQ ID NO:9, wherein said amino acid substitution(s) is selected from the group consisting of N12S/R14P/S25D/T92I, T92I/Y184F, R14P/S25D/T92I/S138T/A161G/M172K/W175F/H182Q/Y184F/Q212N, N12S/I139V, T92I/I139V/H182Q/Y184F, N12S/S25D/T92I/M172K/Y184F/M194L, R14P/S25D/N40S/G44S/S160A/A161G/V171I/Y184F, N12S/S138T/I139V/A161G/M172K/W175F/H182Q/Y184F, S25D/Q65G/T92I/H182Q/Y184F/M194L/Q212N, N12S/R14P/S25D/S138T/S160A/Y184F, N12S/S25D/N40S/G44S/S138T/I139V/H182Q, N12S/R14P/S25D/Q65G/V171I/M172K/W175F/H182Q/Y184F, N12S/R14P/S25D/G44S/T92I/S138T/I139V/S160A/A161G/W175F, S160A/Q212N, N12S/R14P/S25D/S138T/A161G/Y184F, R14P/T92I/A161G/V171I/W175F/Y184F, T92I/A161G/H182Q/Y184F, R14P/A161G/H182Q/Y184F, R14P/S25D/N40S/G44S/S160A/A161G/M172K, N12S/A161G/H182Q/Y184F, N12S/R14P/T92I/A161G/V171I/Y184F, S25D/N40S/T92I/S138T/S160A/A161G/V171I/H182Q/Y184F, R14P/S25D/N40S/G44S, Y184F, N12S/R14P/S25D/T92I/S138T/A161G, N12S/R14P/G44S/T92I/M194L, R14P/S25D/N40S/S138T/Q212N, N12S/S25D/N40S/G44S/Q65G, S25D/G44S/S138T/I139V, S25D/H182Q, R14P/S25D/G44S, N12S/S25D/N40S/G44S/T92I/M172K/H182Q/Q212N, R14P/S25D/N40S/G44S/A161G/V171I/Y184F, N12S/R14P/S25D/A161G/M172K/W175F/Y184F, and N12S/R14P/S25D/N40S/G44S/T92I/I139V.

In some embodiments, the variant endoglucanase enzyme comprises at least one amino acid substitution as compared to SEQ ID NO:9, wherein said amino acid substitution(s) are N12S/S25D/T92I/M172K/Y184F/M194L.

In some embodiments, the variant endoglucanase enzyme comprises at least one amino acid substitution as compared to SEQ ID NO:9, wherein said amino acid substitution(s) are S25D/Q65G/T92I/H182Q/Y184F/M194L/Q212N.

In some embodiments, the variant endoglucanase enzyme comprises at least one amino acid substitution as compared to SEQ ID NO:9, wherein said amino acid substitution(s) are R14P/S25D/N40S/G44S/S160A/A161G/M172K.

In some embodiments, the invention provides a variant glucoamylase enzyme as described herein, wherein said amino acid substitutions comprise N12S/S25D/T92I/M172K/Y184F/M194L, and further comprise at least one amino acid selected from the group consisting of R14P, N40S, G44S, Q65G, S138T, I139V, S160A, A161G, V171I, W175F, H182Q, and Q212N.

In some embodiments, the invention provides a variant glucoamylase enzyme as described herein, wherein said amino acid substitutions comprise S25D/Q65G/T92I/H182Q/Y184F/M194L/Q212N, and further comprise at least one amino acid selected from the group consisting of N12S, R14P, N40S, G44S, S138T, I139V, S160A, A161G, V171I, M172K, and W175F.

In some embodiments, the invention provides a variant glucoamylase enzyme as described herein, wherein said amino acid substitutions comprise R14P/S25D/N40S/G44S/S160A/A161G/M172K, and further comprise at least one amino acid selected from the group consisting of G44S, Q65G, T92I, S138T, I139V, V171I, W175F, H182Q, Y184F, M194L, and Q212N.

In some embodiments, the variant endoglucanase enzymes comprise one or more variants selected from FIG. 3, FIG. 4, FIG. 5 or FIG. 6.

In some embodiments, the variant endoglucanase enzyme is an isolated variant endoglucanase enzyme.

In some embodiments, the variant englucanase comprises an amino acid substitution of the Asparagine at position 12 as compared to EG140 G1P (SEQ ID NO:1) mature protein. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is N12S.

In some embodiments, the variant englucanase comprises an amino acid substitution of the Glycine at position 25 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G25D.

In some embodiments, the variant englucanase comprises an amino acid substitution of the Asparagine at position 40 as compared to EG140 G1P (SEQ ID NO:1) mature protein. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is N40S.

In some embodiments, the variant englucanase comprises an amino acid substitution of the Alanine at position 44 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is A44S.

In some embodiments, the variant englucanase comprises an amino acid substitution of the Glutamine at position 65 as compared to EG140 G1P (SEQ ID NO:1) mature protein. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is Q65G.

In some embodiments, the variant englucanase comprises an amino acid substitution of the Asparagine at position 138 as compared to EG140 G1P (SEQ ID NO:1) mature protein. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is N138T.

In some embodiments, the variant englucanase comprises an amino acid substitution of the Isoleucine at position 139 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, leucine, methionine, proline, phenylalanine, tryptophan, valine and tyrosine, with some embodiments not utilizing cysteine (due to possible disulfide formation) or proline (due to steric effects). In some embodiments, the amino acid substitution is I139V.

In some embodiments, the variant englucanase comprises an amino acid substitution of the Serine at position 160 as compared to EG140 G1P (SEQ ID NO:1) mature protein. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S160A.

In some embodiments, the variant englucanase comprises an amino acid substitution of the Alanine at position 161 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is A161G.

In some embodiments, the variant englucanase comprises an amino acid substitution of the Valine at position 171 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan and tyrosine, with some embodiments not utilizing cysteine (due to possible disulfide formation) or proline (due to steric effects). In some embodiments, the amino acid substitution is V171I.

In some embodiments, the variant englucanase comprises an amino acid substitution of the Methionine at position 172 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, proline, phenylalanine, tryptophan, valine and tyrosine, with some embodiments not utilizing cysteine (due to possible disulfide formation) or proline (due to steric effects). In some embodiments, the amino acid substitution is M172K.

In some embodiments, the variant englucanase comprises an amino acid substitution of the Tryptophan at position 175 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, valine and tyrosine, with some embodiments not utilizing cysteine (due to possible disulfide formation) or proline (due to steric effects). In some embodiments, the amino acid substitution is W175F.

In some embodiments, the variant englucanase comprises an amino acid substitution of the Histidine at position 182 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is H182Q.

In some embodiments, the variant englucanase comprises an amino acid substitution of the Tyrosine at position 184 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan and valine, with some embodiments not utilizing cysteine (due to possible disulfide formation) or proline (due to steric effects). In some embodiments, the amino acid substitution is Y184F.

In some embodiments, the variant englucanase comprises an amino acid substitution of the Methionine at position 194 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, proline, phenylalanine, tryptophan, valine and tyrosine, with some embodiments not utilizing cysteine (due to possible disulfide formation) or proline (due to steric effects). In some embodiments, the amino acid substitution is M194L.

In some embodiments, the variant englucanase comprises an amino acid substitution of the Lysine at position 212 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is K212N.

In some embodiments, the variant englucanase comprises an amino acid substitution of the Threonine at position 214 as compared to EG140 G1P (SEQ ID NO:1) mature protein. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is T214S.

In some embodiments, the variant englucanase comprises an amino acid substitution of the Asparagine at position 12 as compared to EG140 G1P (SEQ ID NO:1) mature protein. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is N12D, N12E, N12G, or N12T.

In some embodiments, the variant englucanase comprises an amino acid substitution of the Glycine at position 25 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G25S.

In some embodiments, the variant englucanase comprises an amino acid substitution of the Alanine at position 44 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is A44D.

In some embodiments, the variant englucanase comprises an amino acid substitution of the Aspartic acid at position 55 as compared to EG140 G1P (SEQ ID NO:1) mature protein. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation). In some embodiments, the amino acid substitution is D55I, or D55P.

In some embodiments, the variant englucanase comprises an amino acid substitution of the Proline at position 80 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine, with some embodiments not utilizing cysteine (due to possible disulfide formation). In some embodiments, the amino acid substitution is P80G.

In some embodiments, the variant englucanase comprises an amino acid substitution of the Serine at position 86 as compared to EG140 G1P (SEQ ID NO:1) mature protein. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S86A, S86H, or S86Q.

In some embodiments, the variant englucanase comprises an amino acid substitution of the Alanine at position 104 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is A104D.

In some embodiments, the variant englucanase comprises an amino acid substitution of the Glycine at position 126 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G126I, G126K, G126N, G126R, G126S, G126T, or G126V.

In some embodiments, the variant englucanase comprises an amino acid substitution of the Glutamine at position 128 as compared to EG140 G1P (SEQ ID NO:1) mature protein. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is Q128F, or Q128R.

In some embodiments, the variant englucanase comprises an amino acid substitution of the Threonine at position 136 as compared to EG140 G1P (SEQ ID NO:1) mature protein. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is T136M, T136R, or T136Y.

In some embodiments, the variant englucanase comprises an amino acid substitution of the Glutamic acid at position 145 as compared to EG140 G1P (SEQ ID NO:1) mature protein. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is E145A, or E145M.

In some embodiments, the variant englucanase comprises an amino acid substitution of the Threonine at position 152 as compared to EG140 G1P (SEQ ID NO:1) mature protein. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is T152Q.

In some embodiments, the variant englucanase comprises an amino acid substitution of the Isoleucine at position 164 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, leucine, methionine, proline, phenylalanine, tryptophan, valine and tyrosine, with some embodiments not utilizing cysteine (due to possible disulfide formation) or proline (due to steric effects). In some embodiments, the amino acid substitution is I164T.

In some embodiments, the variant englucanase comprises an amino acid substitution of the Threonine at position 165 as compared to EG140 G1P (SEQ ID NO:1) mature protein. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is T165D, or T165Y.

In some embodiments, the variant englucanase comprises an amino acid substitution of the Glycine at position 169 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G169S, or G169T.

In some embodiments, the variant englucanase comprises an amino acid substitution of the Aspartic acid at position 173 as compared to EG140 G1P (SEQ ID NO:1) mature protein. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation). In some embodiments, the amino acid substitution is D173E, D173N, or D173P.

In some embodiments, the variant englucanase comprises an amino acid substitution of the Arginine at position 176 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is R176H.

In some embodiments, the variant englucanase comprises an amino acid substitution of the Threonine at position 179 as compared to EG140 G1P (SEQ ID NO:1) mature protein. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is T179L, or T179Y.

In some embodiments, the variant englucanase comprises an amino acid substitution of the Asparagine at position 181 as compared to EG140 G1P (SEQ ID NO:1) mature protein. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is N181S.

In some embodiments, the variant englucanase comprises an amino acid substitution of the Serine at position 187 as compared to EG140 G1P (SEQ ID NO:1) mature protein. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S187N.

In some embodiments, the variant englucanase comprises an amino acid substitution of the Arginine at position 205 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine, with some embodiments not utilizing cysteine (due to possible disulfide formation). In some embodiments, the amino acid substitution is R205P, or R205Y.

In some embodiments, the variant englucanase comprises an amino acid substitution of the Threonine at position 207 as compared to EG140 G1P (SEQ ID NO:1) mature protein.

In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation). In some embodiments, the amino acid substitution is T207E.

In some embodiments, the variant englucanase comprises an amino acid substitution of the Lysine at position 212 as compared to EG140 G1P (SEQ ID NO:1) mature protein. In some embodiments, the substitution is with any other of the 19 naturally occurring amino acids, namely serine, threonine, asparagine, glutamic acid, glutamine, aspartic acid, arginine, histidine, cysteine, glycine, alanine, isoleucine, leucine, methionine, proline, phenylalanine, tryptophan, valine and tyrosine, with some embodiments not utilizing cysteine (due to possible disulfide formation). In some embodiments, the amino acid substitution is K212E.

In some embodiments, the variant englucanase comprises an amino acid substitution of the Asparagine at position 218 as compared to EG140 G1P (SEQ ID NO:1) mature protein. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation). In some embodiments, the amino acid substitution is N218S.

In some embodiments, the variant englucanase comprises an amino acid substitution of the Asparagine at position 12 as compared to EG185 G1P (SEQ ID NO:9) mature protein. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is N12S.

In some embodiments, the variant englucanase comprises an amino acid substitution of the Arginine at position 14 as compared to EG185 G1P (SEQ ID NO:9) mature protein. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine, with some embodiments not utilizing cysteine (due to possible disulfide formation). In some embodiments, the amino acid substitution is R14P.

In some embodiments, the variant englucanase comprises an amino acid substitution of the Serine at position 25 as compared to EG185 G1P (SEQ ID NO:9) mature protein. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S25D.

In some embodiments, the variant englucanase comprises an amino acid substitution of the Asparagine at position 40 as compared to EG185 G1P (SEQ ID NO:9) mature protein. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is N40S.

In some embodiments, the variant englucanase comprises an amino acid substitution of the Glycine at position 44 as compared to EG185 G1P (SEQ ID NO:9) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G44S.

In some embodiments, the variant englucanase comprises an amino acid substitution of the Glutamine at position 65 as compared to EG185 G1P (SEQ ID NO:9) mature protein. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is Q65G.

In some embodiments, the variant englucanase comprises an amino acid substitution of the Threonine at position 92 as compared to EG185 G1P (SEQ ID NO:9) mature protein. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is T92I.

In some embodiments, the variant englucanase comprises an amino acid substitution of the Serine at position 138 as compared to EG185 G1P (SEQ ID NO:9) mature protein. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S138T.

In some embodiments, the variant englucanase comprises an amino acid substitution of the Isoleucine at position 139 as compared to EG185 G1P (SEQ ID NO:9) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, leucine, methionine, proline, phenylalanine, tryptophan, valine and tyrosine, with some embodiments not utilizing cysteine (due to possible disulfide formation) or proline (due to steric effects). In some embodiments, the amino acid substitution is I139V.

In some embodiments, the variant englucanase comprises an amino acid substitution of the Serine at position 160 as compared to EG185 G1P (SEQ ID NO:9) mature protein. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S160A.

In some embodiments, the variant englucanase comprises an amino acid substitution of the Alanine at position 161 as compared to EG185 G1P (SEQ ID NO:9) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is A161G.

In some embodiments, the variant englucanase comprises an amino acid substitution of the Valine at position 171 as compared to EG185 G1P (SEQ ID NO:9) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan and tyrosine, with some embodiments not utilizing cysteine (due to possible disulfide formation) or proline (due to steric effects). In some embodiments, the amino acid substitution is V171I.

In some embodiments, the variant englucanase comprises an amino acid substitution of the Methionine at position 172 as compared to EG185 G1P (SEQ ID NO:9) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, proline, phenylalanine, tryptophan, valine and tyrosine, with some embodiments not utilizing cysteine (due to possible disulfide formation) or proline (due to steric effects). In some embodiments, the amino acid substitution is M172K.

In some embodiments, the variant englucanase comprises an amino acid substitution of the Tryptophan at position 175 as compared to EG185 G1P (SEQ ID NO:9) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, valine and tyrosine, with some embodiments not utilizing cysteine (due to possible disulfide formation) or proline (due to steric effects). In some embodiments, the amino acid substitution is W175F.

In some embodiments, the variant englucanase comprises an amino acid substitution of the Histidine at position 182 as compared to EG185 G1P (SEQ ID NO:9) mature protein. In some embodiments, the substitution is with any other of the 19 naturally occurring amino acids, namely serine, threonine, asparagine, glutamic acid, glutamine, aspartic acid, lysine, arginine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is H182Q.

In some embodiments, the variant englucanase comprises an amino acid substitution of the Tyrosine at position 184 as compared to EG185 G1P (SEQ ID NO:9) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan and valine, with some embodiments not utilizing cysteine (due to possible disulfide formation) or proline (due to steric effects). In some embodiments, the amino acid substitution is Y184F.

In some embodiments, the variant englucanase comprises an amino acid substitution of the Methionine at position 194 as compared to EG185 G1P (SEQ ID NO:9) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, proline, phenylalanine, tryptophan, valine and tyrosine, with some embodiments not utilizing cysteine (due to possible disulfide formation) or proline (due to steric effects). In some embodiments, the amino acid substitution is M194L.

In some embodiments, the variant englucanase comprises an amino acid substitution of the Glutamine at position 212 as compared to EG185 G1P (SEQ ID NO:9) mature protein. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is Q212N.

In some embodiments, the variant enzymes of the invention have at least 90%, 95%, 96%, 97%, 98% or 99% identical to SEQ ID NO:3, SEQ ID NO:5, SEQ ID NO:7, SEQ ID NO:19, SEQ ID NO:21, or SEQ ID NO:23. In some embodiments, the variant enzyme is SEQ ID NO:3. In some embodiments, the variant enzyme is SEQ ID NO:5. In some embodiments, the variant enzyme is SEQ ID NO:7. In some embodiments, the variant enzyme is SEQ ID NO:19. In some embodiments, the variant enzyme is SEQ ID NO:21. In some embodiments, the variant enzyme is SEQ ID NO:23.

In some embodiments, the variant enzymes of the invention have at least 90%, 95%, 96%, 97%, 98% or 99% identical to SEQ ID NO:11, SEQ ID NO:13, or SEQ ID NO:15. In some embodiments, the variant enzyme is SEQ ID NO:11. In some embodiments, the variant enzyme is SEQ ID NO:13. In some embodiments, the variant enzyme is SEQ ID NO:15.

The amino acid changes that may be present in addition to the specific substitutions described herein may be of a minor nature, that is conservative amino acid substitutions or insertions that do not significantly affect the folding and/or activity of the protein; small deletions, typically of 1 to about 30 amino acids; small amino- or carboxyl-terminal extensions, such as an amino-terminal methionine residue; a small linker peptide of up to about 20 to about 25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuA al, Ala/Glu, and Asp/Gly.

A. Parent Endoglucanase

The parent endoglucanase enzyme may be (a) a polypeptide having at least 85% sequence identity to the polypeptide of SEQ ID NO:1 or SEQ ID NO:9; (b) a polypeptide encoded by a polynucleotide that hybridizes under medium-high stringency conditions with (i) the mature polypeptide coding sequence of SEQ ID NO:1 or SEQ ID NO:9, or (ii) the full-length complement of (i); or (c) a polypeptide encoded by a polynucleotide having at least 70% sequence identity to the mature polypeptide coding sequence of SEQ ID NO:1 or SEQ ID NO:9. For hybridization methods and conditions, see for example, Sambrook et al., 1989, Molecular Cloning, A Laboratory Manual, 2d edition, Cold Spring Harbor, N.Y.

In some embodiments, the parent endoglucanase enzyme has a sequence identity to the polypeptide of SEQ ID NO:1 of at least 85%, at least 90%, at least 91%, at least 92%, at least 93%, at least 94%, at least 95%, at least 96%, at least 97%, at least 98%, at least 99%, or 100%, and have endoglucanase activity. In one aspect, the amino acid sequence of the parent differs by up to 19 amino acids, e.g., 1, 2, 3, 4, 5, 6, 7, 8, 9, 10, 11, 12, 13, 14, 15, 16, 17, 18 or 19, from the mature polypeptide of SEQ ID NO: 1.

In some embodiments, the parent endoglucanase enzyme has a sequence identity to the polypeptide of SEQ ID NO:9 of at least 85%, at least 90%, at least 91%, at least 92%, at least 93%, at least 94%, at least 95%, at least 96%, at least 97%, at least 98%, at least 99%, or 100%, and have endoglucanase activity. In one aspect, the amino acid sequence of the parent differs by up to 19 amino acids, e.g., 1, 2, 3, 4, 5, 6, 7, 8, 9, 10, 11, 12, 13, 14, 15, 16, 17, 18 or 19, from the mature polypeptide of SEQ ID NO:9.

In some embodiments, the parent endoglucanase enzyme is a wild type endoglucanase. In some embodiments, the parent endoglucanase enzyme is SEQ ID NO:1. In some embodiments, the parent endoglucanase enzyme is SEQ ID NO:9.

In some embodiments, the parent endoglucanase enzymes have at least 90%, 95%, 96%, 97%, 98% or 99% identical to SEQ ID NO:3, SEQ ID NO:5, or SEQ ID NO:7, SEQ ID NO:19, SEQ ID NO:21, or SEQ ID NO:23. In some embodiments, the parent endoglucanase enzymes have at least 90%, 95%, 96%, 97%, 98% or 99% identical to SEQ ID NO:11, SEQ ID NO:13, or SEQ ID NO:15. In some aspects, the parent endoglucanase enzyme comprises an amino acid sequence of SEQ ID NO:3, SEQ ID NO:5, or SEQ ID NO:7, SEQ ID NO:19, SEQ ID NO:21, or SEQ ID NO:23. In other aspects, the parent endoglucanase enzyme comprises an amino acid sequence of SEQ ID NO:11, SEQ ID NO:13, or SEQ ID NO:15.

In some embodiments, the parent endoglucanase enzyme is encoded by a polynucleotide having a sequence identity to the mature polypeptide coding sequence of SEQ ID NO:2, SEQ ID NO:4, SEQ ID NO:6, SEQ ID NO:8, SEQ ID NO:20, SEQ ID NO:22 or SEQ ID NO:24 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In some embodiments, the parent endoglucanase enzyme is encoded by a polynucleotide comprising a nucleic acid sequence of SEQ ID NO:2, SEQ ID NO:4, SEQ ID NO:6 SEQ ID NO:8, SEQ ID NO:20, SEQ ID NO:22, and SEQ ID NO:24.

In some embodiments, the parent endoglucanase enzyme is encoded by a polynucleotide having a sequence identity to the mature polypeptide coding sequence of SEQ ID NO:10, SEQ ID NO:12, SEQ ID NO:14 or SEQ ID NO:16 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In some embodiments, the parent endoglucanase enzyme is encoded by a polynucleotide comprising a nucleic acid sequence of SEQ ID NO:10, SEQ ID NO:12, SEQ ID NO:14 or SEQ ID NO:16.

In some embodiments, the parent endoglucanase enzyme is an *Aspergillus udagawae* endoglucanase, e.g., the endoglucanase of SEQ ID NO:1.

In some embodiments, the parent endoglucanase enzyme is an *Aspergillus lentulus* endoglucanase, e.g., the endoglucanase of SEQ ID NO:9.

In one embodiment, the variant endoglucanase enzymes are more stable than the parent endoglucanase enzyme when exposed to temperatures of 20° C., 25° C., 30° C., 40° C., 45° C., 50° C., 52° C., 55° C., 56° C., 58° C., 60° C., 65° C., 66° C., 70° C., 75° C., 80° C. and/or 85° C. for a period of time, generally ranging from about 1, 2, 3, 4, 5, 6, 7, 8, 9 or 10 minutes or longer, depending on the ultimate conditions for the use of the variant endoglucanase enzyme, with some embodiments utilizing thermal challenge times of 5 minutes to 10 minutes, 5 minutes to 15 minutes, 5 minutes to 60 minutes, 10 minutes to 180 minutes all finding use in the present invention. In some embodiments, a challenge of 50° C. and 3 h is used.

Accordingly, in some embodiments the variant endoglucanase enzymes have increased total activity as compared to a parent endoglucanase enzyme, particularly G1P, for at least 180 minutes at 50° C.

In addition, tolerance to pH 6.5 can be a consideration for improvement as well. Accordingly, in some embodiments the variant endoglucanase enzymes have increased tolerance to pH 6.5 as compared to a parent endoglucanase enzyme. In some embodiments, the variant endoglucanase enzymes have increased tolerance to pH 6.5 as compared to a parent endoglucanase enzyme for at least 3 hours at 50° C.

Accordingly, as shown in FIGS. 3, 4, 5 and 6, a number of variant endoglucanase enzymes of the invention exhibit increased total activity and tolerance to pH 6.5 and pH 4.5.

B. Nucleic Acid Compositions

The present invention also provides compositions comprising a variant endoglucanase enzyme encoding nucleic acid of the present invention. Such variant endoglucanase polypeptide encoding nucleic acids can encode any of the variant endoglucanase enzymes recited in the present application, including under section "Variant Endoglucanases of the Invention" above. In some embodiments, the composition comprises a nucleic acid selected from the group consisting of the even numbered sequence of SEQ ID NOs: 2 to 16, 20 to 24.

In some embodiments, the composition comprises a nucleic acid of SEQ ID NO:2. In some embodiments, the composition comprises a nucleic acid of SEQ ID NO:4. In some embodiments, the composition comprises a nucleic acid of SEQ ID NO:6. In some embodiments, the composition comprises a nucleic acid of SEQ ID NO:8. In some embodiments, the composition comprises a nucleic acid of SEQ ID NO:10. In some embodiments, the composition comprises a nucleic acid of SEQ ID NO:12. In some embodiments, the composition comprises a nucleic acid of SEQ ID NO:14. In some embodiments, the composition comprises a nucleic acid of SEQ ID NO:16. In some embodiments, the composition comprises a nucleic acid of SEQ ID NO:20. In some embodiments, the composition comprises a nucleic acid of SEQ ID NO:22. In some embodiments, the composition comprises a nucleic acid of SEQ ID NO:24.

In some embodiments, the variant endoglucanase enzyme encoding nucleic acid comprises a codon optimized version or variant of any of the even numbered sequence of SEQ ID NOs: 2 to 16, 20 to 24.

In some embodiments, the present invention provides a nucleic acid encoding a variant endoglucanase enzyme comprising at least one amino acid substitution as compared to SEQ ID NO:1, wherein said amino acid substitution is at a position number selected from the group consisting of 12, 25, 40, 44, 65, 138, 139, 160, 161, 171, 172, 175, 182, 184, 194, 212, 214, 55, 80, 86, 104, 126, 128, 136, 145, 152, 164, 165, 169, 173, 176, 179, 181, 187, 205, 207 and 218, and wherein said variant enzyme is at least 90% identical to SEQ ID NO:1.

In some embodiments, the present invention provides a nucleic acid encoding a variant endoglucanase enzyme comprising at least one amino acid substitution as compared to SEQ ID NO:1, wherein said amino acid substitution is at a position number selected from the group consisting of 12, 25, 40, 44, 65, 138, 139, 160, 161, 171, 172, 175, 182, 184, 194, 212, 214, 55, 80, 86, 104, 126, 128, 136, 145, 152, 164, 165, 169, 173, 176, 179, 181, 187, 205, 207 and 218, wherein said variant endoglucanase enzyme has at least 1.1 fold better activity as compared to SEQ ID NO:1 under a condition selected from the group consisting of total activity at about 30° C., total activity at about 40° C., total activity at about 50° C., total activity at about 60° C., and total activity thermostability at about 70° C.; and wherein said variant enzyme is at least 90% identical to SEQ ID NO:1.

In some embodiments, the present invention provides a nucleic acid encoding a variant endoglucanase enzyme comprising at least one amino acid substitution as compared to SEQ ID NO:1, wherein said amino acid substitution is at a position number selected from the group consisting of 12, 25, 40, 44, 65, 138, 139, 160, 161, 171, 172, 175, 182, 184, 194, 212, 214, 55, 80, 86, 104, 126, 128, 136, 145, 152, 164, 165, 169, 173, 176, 179, 181, 187, 205, 207 and 218, wherein said variant endoglucanase enzyme has at least 1.1 fold better activity as compared to SEQ ID NO:1 under a condition selected from the group consisting of tolerance against pH 3.0, tolerance against pH 3.5, tolerance against pH 4.0, tolerance against pH 4.5, tolerance against pH 5.0, tolerance against pH 5.5, tolerance against pH 6.0, tolerance against pH 6.5, tolerance against pH 7.0, tolerance against pH 7.5 and tolerance against pH 8.0; and wherein said variant enzyme is at least 90% identical to SEQ ID NO:1.

In some embodiments, the present invention provides a nucleic acid encoding a variant endoglucanase enzyme as described herein, wherein said variant endoglucanase enzyme exhibits at least 95%, 96%, 97%, 98%, or 99% identity to SEQ ID NO:1.

In some embodiments, the present invention provides a nucleic acid encoding a variant endoglucanase enzyme as described herein, wherein said amino acid substitution(s) occur at one of said positions, two of said positions, three of said positions, four of said positions, five of said positions, six of said positions, seven of said positions, eight of said positions, nine of said positions, ten of said positions, eleven of said positions or twelve of said positions.

In some embodiments, the present invention provides a nucleic acid encoding a variant endoglucanase enzyme as described herein, wherein said amino acid substitution(s) is selected from the group consisting of N12S, G25D, N40S, A44S, Q65G, N138T, I139V, S160A, A161G, V171I, M172K, W175F, H182Q, Y184F, M194L, K212N, T214S, N12D, N12E, N12G, N12T, G25S, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, K212E and N218S.

In some embodiments, the present invention provides a nucleic acid encoding a variant endoglucanase enzyme as described herein, wherein said amino acid substitution(s) is selected from the group consisting of G25D/A161G/M172K/H182Q/M194L/K212N, N12S/G25D/Q65G/S160A/A161G/V171I/Y184F/M194L/K212N, G25D/N138T/V171I/W175F/H182Q/Y184F, G25D/N138T/I139V/M194L, H182Q/K212N, G25D/A161G/T214S, N12S/G25D/A161G/H182Q/Y184F/M194L/K212N/T214S, G25D/N138T/H182Q/K212N, N12S/G25D/A44S/I139V, G25D/N138T/K212N, G25D/V171I/W175F/M194L/K212N, G25D/A161G/K212N, V171I/Y184F, G25D/A44S/A161G, G25D/M172K/H182Q, G25D/A44S/V171I/M172K/H182Q/K212N, G25D/V171I/M172K/H182Q/M194L, H182Q/M194L, G25D/K212N, N12S/G25D/N138T/A161G/K212N, G25D/H182Q/Y184F/M194L/K212N, N12S/G25D/N40S/I139V/V171I/M172K/H182Q/Y184F/M194L/K212N/T214S, N12S/G25D/H182Q/K212N, G25D/N40S/A44S/N138T/A161G/V171I/W175F/Y184F/M194L/K212N, N12S/N40S/Y184F/T214S, N12S/G25D/A44S/Q65G, G25D/A161G/M194L/T214S, A44S/N138T/I139V/V171I/H182Q/Y184F/M194L/K212N, G25D/Y184F/M194L/K212N, N12S/G13P/D55P/M172K/R205P/K212N, N12S/G25D/D55P/V171I/M172K/S187P, G25D/S187P, G13P/G25D/D55P/A161P/S187P/R205P/K212N, G25D/D55P, N12S/R133P/A161P/V171I/S187P/K212N, N12S/G25D, G13P/G25D/D55P/V171I/S187P/R205P, G13P/G25D/V171I/M172K/S187P/R205P/K212N, G25D/D55P/R205P, G25D/V171I/M172K, G25D/R133P, N12S/G25D/V171I/M172K, N12S/G25D/H182Q/R205P, N12S/G25D/A161P/S187P/K212N, G25D/D55P/V171I/M172K/R205P, D55P/R205P, N12S/R205P, N12S/G25D/T69P/R133P/V171I/M172K/R205P/K212N, T179Y/R205Y, N12E/G25D/D55I/G126V/T136M/T165D/R205P, N12E/G25D/D55I/G126S/T136Y/R205P/T207E/N218S, N12E/G25S/D55P/N181S/R205P, N12E/G25D/D55I/P80G/G126I/T136M/R205P, N12E/G25D/D55P/G126K/E145A/T165D/R205P, N12E/G25D/D55I/G126T/T136M/T165Y/T179L/R205P, N12E/G25S/D55P/P80G/G126T/T136Y/T165Y/R205P/T207E, N12E/G25S/D55P/G126T/R205P/T207E, N12E/G25D/D55P/G126N/T136Y/T165Y/

T179Y/N181S/R205P/T207E, N12E/G25S/D55P/P80G/ G126R/T136Y/R205P, G25D/D55P/G126T/T165Y/R205P, N12E/G25S/D55I/G126K/T165D/R205P, N12E/G25S/ D55P/G126I/T136Y/R205P, G25D/D55P/G126K/T136Y/ T179Y/N181S/R205P, N12E/G25D/D55I/G126R/R205P, N12E/G25S/D55P/G126N/R205P/T207E, N12E/G25D/ D55P/P80G/E145A/R205P/T207E, G25D/D55P/T136Y/ T165Y/R205P/T207E, N12E/G25S/D55P/G126R/T136Y/ T165Y/R205P, N12E/G25D/D55P/P80G/R205P, G25D/ D55I/G126K/R205Y, N12E/G25S/D55P/G126R/R205P/ T207E, G25D/D55P/G126T/T136Y/T165Y/R205P/N218S, N12E/G25D/D55P/G126N/R205P, N12E/G25D/D55P/ G126K/R205P, N12E/G25D/D55P/T165D/R205Y, N12E/ G25D/D55I/P80G/G126R/R205P/T207E, N12E/G25S/ D55P/G126K/T165D/R205P, G25D/D55P/G126V/T136Y/ R205P/T207E, G25D/D55P/T179L/N181S/R205P/T207E, N12E/G25S/D55P/T165Y/R205P/N218S, N12E/G25D/ D55I/G126V/T136M/R205P/N218S, G25S/D55P/G126R/ T136M/E145A/R205P, N12E/G25D/D55I/G126T/T136M/ R205Y, N12E/G25S/D55P/G126V/E145A/T179Y/R205P, N12E/G25S/D55P/G126T/T165Y/R205P, G25S/D55P/ G126R/R205P/N218S, N12E/G25S/D55P/G126T/T136Y/ R205P/T207E, N12E/G25S/D55I/G126R/T136M/T165Y/ R205P/T207E/N218S, N12E/G25S/D55P/G126S/T136M/ T165Y/R205Y, N12D/G25D/D55P/S86A/E145M/I164T/ D173P/R205P/T207E, N12E/G25D/A44D/D55P/S86H/ Q128F/R205P, G25S/D55P/G126I/D173N/R205P/T207E, N12D/G25S/A44D/D55P/S86Q/T152Q/R176H/S187N/ R205P/K212E, N12D/G25D/A44D/D55P/Q128R/E145A/ D173E/R205P, N12D/G25D/A44D/D55P/S86A/E145A/ R205P/T207E, N12D/G25S/D55P/T136Y/G169T/R176H/ R205P/K212E, N12E/G25D/D55P/S86Q/A104D/G126T/ E145A/D173E/R205P/K212E, G25D/A44D/D55P/I164T/ R205P, N12T/G25D/D55P/S86A/A104D/Q128R/T165Y/ R176H/R205P/K212E/N218S, N12D/G25D/D55P/P80G/ S86A/Q128R/I164T/D173E/R205P/K212E, N12D/G25S/ D55P/Q128R/T165Y/R176H/R205P/K212E, N12G/G25D/ A44D/D55P/Q128R/I164T/D173E/R205P, N12T/G25D/ D55P/G126K/E145A/T165D/D173E/R205P, G25D/A44D/ D55P/Q128R/R205P/T207E, G25S/D55P/G126S/T165D/ G169S/T179Y/R205P/K212E, G25S/A44D/D55P/P80G/ S86A/G126K/Q128R/R205P/K212E, G25S/D55P/P80G/ G126T/R205P, N12T/G25D/D55P/P80G/G126S/T152Q/ S187N/R205P, G25S/D55P/G126K/T136R/T152Q/R176H/ T179Y/R205P/K212E, G25D/D55P/G126T/T165Y/ R176H/R205P, N12D/G25D/D55P/S86Q/A104D/E145A/ R205P/T207E/N218S, G25D/A44D/D55P/A104D/Q128R/ E145A/T165D/R176H/R205P/K212E, G25D/D55P/R205P/ K212N, N12E/G25S/D55R/G126T/T136Y/R205P/T207E, N12E/V17I/G25S/D55P/G126T/T136Y/R205P/T207E, N12E/G25S/V35I/D55P/G126T/T136Y/R205P/T207E, N12E/G25S/D55P/G126T/V127I/T136Y/R205P/T207E, N12E/G25S/G42S/D55P/G126T/T136Y/R205P/T207E, N12E/G25S/D55P/Y124F/G126T/T136Y/R205P/T207E, N12E/G25S/D55P/S78T/G126T/T136Y/R205P/T207E, N12D/G25D/A44D/D55P/S86Q/G126T/T136Y/R176H/ S187N/R205P/T207E, N12T/G25D/D55P/G126T/T136Y/ S187N/R205P/T207E/K212E, N12D/G25D/D55P/G126T/ T136Y/R205P/T207E, N12D/G25D/D55P/S86Q/G126T/ T136Y/R205P/T207E, N12D/G25S/D55P/S86Q/G126T/ T136Y/T165Y/S187N/R205P/T207E/K212E, N12E/G25S/ S28N/D55P/G126T/T136Y/R205P/T207E, N12E/G25S/ S39Y/D55P/G126T/T136Y/R205P/T207E, N12E/G25S/ D55P/G126T/T136Y/R205P/T207E/K212N, N12T/G25S/ A44D/D55P/S86Q/G126N/T136M/R176H/S187N/R205P/ T207E/K212E, N12E/G25D/D55P/G126T/T136Y/S187N/ R205P/T207E/K212E, N12D/G25D/D55P/G126T/T136M/ S187N/R205P/T207E, N12D/G25D/D55P/A104D/G126T/ T136Y/S187N/R205P/T207E/K212E, N12T/G25D/D55P/ S86Q/G126T/T136M/R176H/S187N/R205P/T207E/ K212E, N12D/G25S/A44D/D55P/S86Q/A104D/G126T/ T136Y/R205P/T207E, N12E/G25D/D55P/S86Q/G126T/ T136M/D173L/R176H/R205P/T207E, N12D/G25D/D55P/ G126T/T136Y/R205P/T207E/K212E, N12D/G25D/A44D/ D55P/G126T/T136Y/S187N/R205P/T207E/K212E, N12E/ G25D/A44D/D55P/G126S/T136Y/S187N/R205P/T207E, N12D/G25D/A44D/D55P/G126T/T136Y/S187N/R205P/ T207E, and N12D/G25D/A44D/D55P/S86Q/G126K/ T136Y/D173E/R176H/S187N/R205P/T207E.

In some embodiments, the present invention provides a nucleic acid encoding a variant endoglucanase enzyme as described herein, wherein said amino acid substitutions are G25D/A44S/V171I/M172K/H182Q/K212N.

In some embodiments, the present invention provides a nucleic acid encoding a variant endoglucanase enzyme as described herein, wherein said amino acid substitutions are G25D/K212N.

In some embodiments, the present invention provides a nucleic acid encoding a variant endoglucanase enzyme as described herein, wherein said amino acid substitutions are N12S/G25D/H182Q/K212N.

In some embodiments, the present invention provides a nucleic acid encoding a variant endoglucanase enzyme as described herein, wherein said amino acid substitutions are G25D/D55P/R205P.

In some embodiments, the present invention provides a nucleic acid encoding a variant endoglucanase enzyme as described herein, wherein said amino acid substitutions are N12E/G25S/D55P/G126T/T136Y/R205P/T207E.

In some embodiments, the present invention provides a nucleic acid encoding a variant endoglucanase enzyme as described herein, wherein said amino acid substitutions are N12E/G25S/D55P/G126T/T136Y/R205P/T207E/K212N.

In some embodiments, the present invention provides a nucleic acid encoding a variant endoglucanase enzyme as described herein, wherein said variant glucoamylase enzyme comprises an amino acid substitution G25D/A44S/V171I/ M172K/H182Q/K212N, and further comprises at least one amino acid selected from the group consisting of N12S, N40S, Q65G, N138T, I139V, S160A, A161G, W175F, Y184F, M194L, T214S, N12D, N12E, N12G, N12T, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

In some embodiments, the present invention provides a nucleic acid encoding a variant endoglucanase enzyme as described herein, wherein said variant glucoamylase enzyme comprises an amino acid substitution G25D/K212N, and further comprises at least one amino acid selected from the group consisting of N12S, N40S, A44S, Q65G, N138T, I139V, S160A, A161G, V171I, M172K, W175F, H182Q, Y184F, M194L, T214S, N12D, N12E, N12G, N12T, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

In some embodiments, the present invention provides a nucleic acid encoding a variant endoglucanase enzyme as described herein, wherein said variant glucoamylase enzyme comprises an amino acid substitution N12S/G25D/H182Q/ K212N, and further comprises at least one amino acid selected from the group consisting of N40S, A44S, Q65G, N138T, I139V, S160A, A161G, V171I, M172K, W175F, Y184F, M194L, T214S, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

In some embodiments, the present invention provides a nucleic acid encoding a variant endoglucanase enzyme as described herein, wherein said variant glucoamylase enzyme comprises an amino acid substitution G25D/D55P/R205P, and further comprises at least one amino acid selected from the group consisting of N12S, N40S, A44S, Q65G, N138T, I139V, S160A, A161G, V171I, M172K, W175F, H182Q, Y184F, M194L, K212N, T214S, N12D, N12E, N12G, N12T, A44D, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, T207E, K212E, and N218S.

In some embodiments, the present invention provides a nucleic acid encoding a variant endoglucanase enzyme as described herein, wherein said variant glucoamylase enzyme comprises an amino acid substitution N12E/G25S/D55P/ G126T/T136Y/R205P/T207E, and further comprises at least one amino acid selected from the group consisting of N40S, A44S, Q65G, N138T, I139V, S160A, A161G, V171I, M172K, W175F, H182Q, Y184F, M194L, K212N, T214S, A44D, P80G, S86A, S86H, S86Q, A104D, Q128F, Q128R, E145A, E145M, T152Q, I164T, T165D, T165Y, G169S, G169T, D173E, D173N, D173P, R176H, T179L, T179Y, N181S, S187N, K212E, and N218S.

In some embodiments, the present invention provides a nucleic acid encoding a variant endoglucanase enzyme as described herein, wherein said variant glucoamylase enzyme comprises an amino acid substitution N12E/G25S/D55P/ G126T/T136Y/R205P/T207E/K212N, and further comprises at least one amino acid selected from the group consisting of N40S, A44S, Q65G, N138T, I139V, S160A, A161G, V171I, M172K, W175F, H182Q, Y184F, M194L, T214S, A44D, P80G, S86A, S86H, S86Q, A104D, Q128F, Q128R, E145A, E145M, T152Q, I164T, T165D, T165Y, G169S, G169T, D173E, D173N, D173P, R176H, T179L, T179Y, N181S, S187N, and N218S.

In some embodiments, the present invention provides a nucleic acid encoding a variant endoglucanase enzyme comprising at least one amino acid substitution as compared to SEQ ID NO:9, wherein said amino acid substitution is at a position number selected from the group consisting of 12, 14, 25, 40, 44, 65, 92, 138, 139, 160, 161, 171, 172, 175, 182, 184, 194, and 212, and wherein said variant enzyme is at least 90% identical to SEQ ID NO:9.

In some embodiments, the present invention provides a nucleic acid encoding a variant endoglucanase enzyme comprising at least one amino acid substitution as compared to SEQ ID NO:9, wherein said amino acid substitution is at a position number selected from the group consisting of 12, 14, 25, 40, 44, 65, 92, 138, 139, 160, 161, 171, 172, 175, 182, 184, 194, and 212, wherein said variant endoglucanase enzyme has at least 1.1 fold better activity as compared to SEQ ID NO:9 under a condition selected from the group consisting of total activity at about 30° C., total activity at about 40° C., total activity at about 50° C., total activity at about 60° C., and total activity thermostability at about 70° C.; and wherein said variant endoglucanase enzyme is at least 90% identical to SEQ ID NO:9.

In some embodiments, the present invention provides a nucleic acid encoding a variant endoglucanase enzyme comprising at least one amino acid substitution as compared to SEQ ID NO:9, wherein said amino acid substitution is at a position number selected from the group consisting of 12, 14, 25, 40, 44, 65, 92, 138, 139, 160, 161, 171, 172, 175, 182, 184, 194, and 212, wherein said variant endoglucanase enzyme has at least 1.1 fold better activity as compared to SEQ ID NO:9 under a condition selected from the group consisting of tolerance against pH 3.0, tolerance against pH 3.5, tolerance against pH 4.0, tolerance against pH 4.5, tolerance against pH 5.0, tolerance against pH 5.5, tolerance against pH 6.0, tolerance against pH 6.5, tolerance against pH 7.0, tolerance against pH 7.5 and tolerance against pH 8.0; and wherein said variant endoglucanase enzyme is at least 90% identical to SEQ ID NO:9.

In some embodiments, the present invention provides a nucleic acid encoding a variant endoglucanase enzyme as described herein, wherein said variant endoglucanase enzyme exhibits at least 95%, 96%, 97%, 98%, or 99% identity to SEQ ID NO:9.

In some embodiments, the present invention provides a nucleic acid encoding a variant endoglucanase enzyme as described herein, wherein said amino acid substitution(s) occur at one of said positions, two of said positions, three of said positions, four of said positions, five of said positions, six of said positions, seven of said positions, eight of said positions, nine of said positions, ten of said positions or eleven of said positions.

In some embodiments, the present invention provides a nucleic acid encoding a variant endoglucanase enzyme as described herein, wherein said amino acid substitution(s) is selected from the group consisting of N12S, R14P, S25D, N40S, G44S, Q65G, T92I, S138T, I139V, S160A, A161G, V171I, M172K, W175F, H182Q, Y184F, M194L, and Q212N.

In some embodiments, the present invention provides a nucleic acid encoding a variant endoglucanase enzyme as described herein, wherein said amino acid substitution(s) is selected from the group consisting of N12S/R14P/S25D/ T92I, T92I/Y184F, R14P/S25D/T92I/S138T/A161G/ M172K/W175F/H182Q/Y184F/Q212N, N12S/I139V, T92I/ I139V/H182Q/Y184F, N12S/S25D/T92I/M172K/Y184F/ M194L, R14P/S25D/N40S/G44S/S160A/A161G/V171I/ Y184F, N12S/S138T/I139V/A161G/M172K/W175F/ H182Q/Y184F, S25D/Q65G/T92I/H182Q/Y184F/M194L/ Q212N, N12S/R14P/S25D/S138T/S160A/Y184F, N12S/ S25D/N40S/G44S/S138T/I139V/H182Q, N12S/R14P/ S25D/Q65G/V171I/M172K/W175F/H182Q/Y184F, N12S/ R14P/S25D/G44S/T92I/S138T/I139V/S160A/A161G/ W175F, S160A/Q212N, N12S/R14P/S25D/S138T/A161G/ Y184F, R14P/T92I/A161G/V171I/W175F/Y184F, T92I/ A161G/H182Q/Y184F, R14P/A161G/H182Q/Y184F, R14P/S25D/N40S/G44S/S160A/A161G/M172K, N12S/ A161G/H182Q/Y184F, N12S/R14P/T92I/A161G/V171I/ Y184F, S25D/N40S/T92I/S138T/S160A/A161G/V171I/ H182Q/Y184F, R14P/S25D/N40S/G44S, Y184F, N12S/ R14P/S25D/T92I/S138T/A161G, N12S/R14P/G44S/T92I/ M194L, R14P/S25D/N40S/S138T/Q212N, N12S/S25D/ N40S/G44S/Q65G, S25D/G44S/S138T/I139V, S25D/ H182Q, R14P/S25D/G44S, N12S/S25D/N40S/G44S/T92I/ M172K/H182Q/Q212N, R14P/S25D/N40S/G44S/A161G/ V171I/Y184F, N12S/R14P/S25D/A161G/M172K/W175F/ Y184F, and N12S/R14P/S25D/N40S/G44S/T92I/I139V.

In some embodiments, the present invention provides a nucleic acid encoding a variant endoglucanase enzyme as described herein, wherein said amino acid substitutions are N12S/S25D/T92I/M172K/Y184F/M194L.

In some embodiments, the present invention provides a nucleic acid encoding a variant endoglucanase enzyme as described herein, wherein said amino acid substitutions are S25D/Q65G/T92I/H182Q/Y184F/M194L/Q212N.

In some embodiments, the present invention provides a nucleic acid encoding a variant endoglucanase enzyme as described herein, wherein said amino acid substitutions are R14P/S25D/N40S/G44S/S160A/A161G/M172K.

In some embodiments, the invention provides a variant glucoamylase enzyme as described herein, wherein said amino acid substitutions comprise N12S/S25D/T92I/M172K/Y184F/M194L, and further comprise at least one amino acid selected from the group consisting of R14P, N40S, G44S, Q65G, S138T, I139V, S160A, A161G, V171I, W175F, H182Q, and Q212N.

In some embodiments, the invention provides a variant glucoamylase enzyme as described herein, wherein said amino acid substitutions comprise S25D/Q65G/T92I/H182Q/Y184F/M194L/Q212N, and further comprise at least one amino acid selected from the group consisting of N12S, R14P, N40S, G44S, S138T, I139V, S160A, A161G, V171I, M172K, and W175F.

In some embodiments, the invention provides a variant glucoamylase enzyme as described herein, wherein said amino acid substitutions comprise R14P/S25D/N40S/G44S/S160A/A161G/M172K, and further comprise at least one amino acid selected from the group consisting of G44S, Q65G, T92I, S138T, I139V, V171I, W175F, H182Q, Y184F, M194L, and Q212N.

"Codon optimized" in this context is done in relation to a particular host organism and its generally preferred amino acid codons; that is, the host production organism, e.g. an *Aspergillus* species, may yield higher translation and/or secretion using *Aspergillus* preferred codons as compared to a yeast production organism.

In some embodiments, the compositions are enriched in such a variant endoglucanase enzyme encoding nucleic acid of the present invention. The term "enriched" indicates that the endoglucanase activity capable of being obtained from the composition has been increased, e.g., with an enrichment factor of at least 1. In some embodiments, the compositions are formulated to provide desirable characteristics such as low color, low odor and acceptable storage stability.

1. Preparation of Variants

The variants can be prepared generally by construction genes encoding the protein sequence using well known techniques, including site-directed mutagenesis of a parental gene and synthetic gene construction.

i. Regulatory sequences

The present invention also relates to nucleic acid constructs comprising a polynucleotide encoding a variant of the present invention operably linked to one or more control sequences that direct the expression of the coding sequence in a suitable host cell under conditions compatible with the control sequences. The control sequence may include a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from *Aspergillus* species genes, as is known in the art, including *A. nidulans*, *A. niger* and *A. oryzae*, as well as *Rhizomucor* species genes such as *R. miehei*, *Trichoderma* species genes including *T. reesei*, *Fusarium* species genes including *F. venenatum*. Yeast control sequences including promoters are also well known from *Saccharomyces cerevisiae*.

Suitable promoter sequences (as well as other control sequences) from these species include the promoters from amylases (α-amylase in particular), glucoamylases, proteases, phosphatases, endoglucanases, cellulases, etc. as are known in the art. In addition, as for codon-optimization, it may be desirable to use promoters (and other control sequences) that are endogeneous to the host production strain, operably linked to the nucleic acids encoding the variant endoglucanases. In many embodiments, the promoter that is operably attached to the coding sequence is not the native promoter sequence.

The control sequence may also be a transcription terminator, which is recognized by a host cell to terminate transcription. The terminator sequence is operably linked to the 3'-terminus of the polynucleotide encoding the variant. Any terminator that is functional in the host cell can be used.

In some embodiments, terminators (and other control sequences such as promoters) for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

In some embodiments, terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase.

The control sequence can also be an mRNA stabilizer region downstream of a promoter and upstream of the coding sequence of a gene which increases expression of the gene.

Examples of suitable mRNA stabilizer regions are obtained from a *Bacillus thuringiensis* cry111A gene (WO 94/25612) and a *Bacillus subtilis* SP82 gene (Hue et al., 1995, *Journal of Bacteriology* 177: 3465-3471).

The control sequence can also be a leader, a nontranslated region of an mRNA that is important for translation by the host cell. The leader sequence is operably linked to the 5'-terminus of the polynucleotide encoding the variant. Any leader that is functional in the host cell may be used.

In some embodiments, leaders for filamentous fungal host cells are obtained from the genes for *Aspergillus oryzae* TAKA amylase and *Aspergillus nidulans* triose phosphate isomerase.

In some embodiments, suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP)

The control sequence can also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

In some embodiments, polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

The control sequence may also be a signal peptide coding region that encodes a signal peptide linked to the N-terminus of a variant and directs the variant endoglucanase being expressed into the cell's secretory pathway. In some instances, the signal sequence is that depicted in FIG. 2, the EG140 G1P or EG185 G1P signal peptide sequence.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the Gpd (Glyceraldehyde-3-phosphate dehydrogenase) from Ascomycota such as *Aspergillus*, *Aspergillus niger* glucoamylase promoter, *Aspergillus oryzae* TAKA alpha-amylase promoter, and *Aspergillus oryzae* glucoamylase promoter can be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

In some embodiments, the present invention provides a nucleic acid encoding a preprotein comprising a signal peptide and a mature protein, wherein the mature protein can be any of the variant endoglucanase enzymes as described herein, and wherein the signal peptide can be endogenous or exogenous. In some embodiments, the invention provides a nucleic acid encoding a preprotein comprising a signal peptide and a mature protein, wherein the mature protein is the variant endoglucanase enzyme as described herein and is operably linked to an endogenous or exogenous construct sequence.

In some embodiments, the present invention provides a nucleic acid encoding a preprotein comprising a signal peptide and a mature protein as described herein, wherein the signal peptide has a sequence identity of at least 93%, at least 94%, at least 95%, at least 96%, at least 97%, at least 98% or at least 99% to SEQ ID NO:17 or SEQ ID NO:18. In some embodiments, the signal peptide has SEQ ID NO:17 or SEQ ID NO:18.

In some embodiments, the present invention provides a nucleic acid encoding an endoglucanase enzyme having SEQ ID NO:1 or SEQ ID NO:9.

In some embodiments, the present invention provides a nucleic acid encoding a preprotein comprising a signal peptide and a mature protein, wherein the mature protein has SEQ ID NO:1 or SEQ ID NO:9 operably linked to an exogenous construct sequence.

In some embodiments, the present invention provides a nucleic acid encoding a preprotein comprising a signal peptide and a mature protein, wherein the signal peptide operably linked to an exogenous construct sequence, and wherein the mature protein has SEQ ID NO:1 or SEQ ID NO:9. In some embodiments, the signal peptide is endogenous. In some embodiments, the signal peptide is exogenous.

In some embodiments, the present invention provides a nucleic acid encoding a preprotein comprising a signal peptide and a mature protein, wherein the signal peptide operably linked to an exogenous construct sequence, and wherein the mature protein has SEQ ID NO:1 or SEQ ID NO:9 operably linked to an exogenous construct sequence.

In some embodiments, the present invention provides a nucleic acid encoding a preprotein comprising a signal peptide and a mature protein as described herein, wherein the mature protein has SEQ ID NO:1 or SEQ ID NO:9, and wherein the signal peptide has a sequence identity of at least 93%, at least 94%, at least 95%, at least 96%, at least 97%, at least 98% or at least 99% to SEQ ID NO:17 or SEQ ID NO:18. In some embodiments, the signal peptide has SEQ ID NO:17 or SEQ ID NO:18.

In some embodiments, the present invention provides a nucleic acid as described herein, wherein exogeneous construct sequence is an exogeneous promoter.

2. Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector can be a linear or closed circular plasmid The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used. Vectors contemplated for use with the methods of the invention include both integrating and non-integrating vectors.

In some embodiments, the vector contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

In some embodiments, the vector contains an element(s) that permits integration of the vector into the host cell's genome or autonomous replication of the vector in the cell independent of the genome.

For integration into the host cell genome, the vector can rely on the polynucleotide's sequence encoding the variant or any other element of the vector for integration into the genome by homologous or non-homologous recombination. Alternatively, the vector can contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector can further comprise an origin of replication enabling the vector to replicate autonomously in the host cell in question. The origin of replication can be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention can be inserted into a host cell to increase production of a variant, including the use of multiple genes encoding the variant endoglucanase in a vector, multiple vectors transformed into a cell, or multiple integrations of a vector into the genome. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

C. Particular Constructs

For expression in yeast, one embodiment utilizes *Saccharomyces cerevisiae* INSCV1 strain (ThermoFisher Scientific, USA: Catalogue #V8251-20) and pESC-URA vector (Agilent Technologies, Santa Clara, Calif., Catalogue #217454). Both are commercially available and are also discussed in Examples below.

1. Codon Optimization

Codon optimization can be employed with any of the variant endoglucanase enzymes of the present invention, in order to optimize expression in the host cell employed. Such methods are well known in the art and described in, for example, WO 2007/142954. In heterologous expression systems, optimization steps can improve the ability of the host to produce the desired variant endoglucanase enzymes. Protein expression is governed by a host of factors including those that affect transcription, mRNA processing, and stability and initiation of translation. The polynucleotide optimization steps can include steps to improve the ability of the host to produce the foreign protein as well as steps to assist the researcher in efficiently designing expression constructs. Optimization strategies can include, for example, the modification of translation initiation regions, alteration of mRNA structural elements, and the use of different codon biases.

In some embodiments, reduced heterologous protein expression occurs through interfering secondary structures. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

In some embodiments, restriction sites can effect heterologous protein expression. By modifying restriction sites that could interfere with subsequent sub-cloning of transcription units into host expression vectors a polynucleotide sequence can be optimized.

In some embodiments, the optimized nucleic acid sequence can express the variant endoglucanase enzyme of the invention, at a level which is at least 110%, 150%, 200%, 500%, 1,000%, 5,000% or even 10,000% of that expressed by nucleic acid sequence that has not been optimized.

D. Host Cells and Production Strains

As will be appreciated by those in the art, there are a wide variety of production host organisms for the recombinant production of the variant endoglucanase enzymes of the invention, including, but not limited to bacterial cells and fungal cells including yeast.

The present invention also relates to recombinant host cells, comprising a polynucleotide encoding a variant endoglucanase of the present invention operably linked to one or more control sequences that direct the production of a variant of the present invention. A construct or vector comprising a polynucleotide is introduced into a host cell so that the construct or vector is maintained as a chromosomal integrant or as a self-replicating extrachromosomal vector as described earlier. The choice of a host cell will to a large extent depend upon the gene encoding the variant and the ability of the host production organism to yield high protein titers of expressed and/or secreted proteins. In some embodiments, the host cell exhibits transitory expression of the variant endoglucanase. In some embodiments, the host cell is a stably transfected host or a host cell that stably (i.e., permanently) expresses the variant endoglucanase. In some embodiments, the host cell is a production host cell. The transformation and/or transfection of the host cells with the expression vectors comprising the coding region for the variant endoglucanases of the invention is done as is well known in the art (See Sambrook, id.).

The host cell can be any cell useful in the recombinant production of a variant, e.g., a prokaryote or a eukaryote. Such host cells include but are not limited to bacterial, fungal, and yeast cells. The host cell can also be a eukaryote, such as a mammalian, insect, plant, or fungal cell.

The host cell can be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK). In many cases, host cells include *Aspergillus* species including *A. nidulans*, *A. niger* and *A. oryzae*, as well as *Rhizomucor* species such as *R. miehei*, *Trichoderma* species including *T. reesei* and *Fusarium* species genes including *F. venenatum*. The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell. For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

In some embodiments, the fungal host cell can be a yeast cell. "Yeast" as used herein includes ascosporogenous yeast (*Endomycetales*), basidiosporogenous yeast, and yeast belonging to the *Fungi Imperfecti* (*Blastomycetes*). The yeast host cell may be a *Candida*, *Hansenula*, *Kluyveromyces*, *Pichia*, *Saccharomyces*, *Schizosaccharomyces*, or *Yarrowia* cell such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

E. Protein Compositions

The present invention also provides compositions comprising a variant endoglucanase enzyme of the present invention. In some embodiments, the composition comprises a carrier and/or an excipient. In some embodiments, the compositions are enriched in such a variant endoglucanase enzyme of the present invention. The term "enriched" indicates that the endoglucanase activity of the composition has been increased, e.g., with an enrichment factor of at least 1. In some embodiments, the compositions are formulated to provide desirable characteristics such as low color, low odor and acceptable storage stability.

In some embodiments, the composition comprises a variant endoglucanase enzyme of the present invention as the major enzymatic component, e.g., a mono-component composition.

In some embodiments, the composition may comprise one or more additional enzymes, depending on the end use, including, but not limited to, aminopeptidase, alpha-amylase, beta-amylase, isoamylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, polyphenoloxidase, pullulanase, proteolytic enzyme, ribonuclease, transglutaminase, and/or xylanase.

In some embodiments, the composition comprises the (variant) endoglucanase enzyme of the invention, and further comprises other cellulases such as acid and/or neutral cellulases. In some embodiments, the composition comprises the (variant) endoglucanase enzyme of the invention, and further comprises acid, neutral and/or alkaline proteases. In another embodiment, the composition comprises the variant endoglucanase according to the invention and a cocktail of enzymes including alpha-amylase, proteases, peptidase, lipase, cellulose, pancreatin, and others.

In some embodiments, the composition comprises the (variant) endoglucanase enzyme of the invention, and further comprises other macromolecules that are not necessarily all produced from the same host (for example, other enzymes such as endoglucanases, amylases, lipases, proteases, pectinases and/or oxidases, such as laccases and peroxidases) or chemicals that may enhance the performance, stability, or buffering of the desired enzyme composition.

In some embodiments, the composition comprising the (variant) endoglucanase enzyme of the invention further comprises a surfactant which can be anionic, non-ionic, cationic, amphoteric or a mixture of these types, especially when used as a detergent composition. Useful detergent compositions are described e.g. in WO94/07998, U.S. Pat. Nos. 5,443,750 and 3,664,961, which are all incorporated by reference in their entireties.

In some embodiments, a desired enzyme may be further purified in accordance with conventional conditions, such as extraction, precipitation, chromatography, affinity chromatography, electrophoresis, or the like.

F. Formulations of Variant Endoglucanases

In some embodiments, the compositions can be prepared in accordance with methods known in the art and can be in the form of a liquid or a dry composition. For instance, the composition may be in the form of granulate or microgranulate. In some embodiments, the non-dusting granules may be coated. The (variant) endoglucanases of the invention can be stabilized in accordance with methods known in the art, for example, liquid enzyme compositions can be stabilized by adding a polyol such as propylene glycol, a sugar or sugar alcohol, lactic acid or boric acid, or sodium chloride, according to established methods. (see U.S. Pat. No. 7,256,032 incorporated by reference in its entirety). Protected forms of the enzyme composition may be prepared as described in EP 238,216, incorporated by reference in its entirety.

In some embodiments, the enzyme composition (i.e., polypeptide compositions) of the present invention can be in any form suitable for use, such as, for example, a crude fermentation broth with or without cells removed, a cell lysate with or without cellular debris, a semi-purified or purified enzyme composition, or a host cell, as a source of the enzymes.

In some embodiments, the enzyme composition can be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In some embodiments, the dosage of the polypeptide composition of the invention and other conditions under which the composition is used may be determined on the basis of methods known in the art.

G. Methods of Production

The present invention also relates to methods of producing a variant endoglucanase enzyme, comprising: (a) cultivating a host cell of the present invention under conditions suitable for expression of the variant endoglucanase polypeptide; and (b) optionally recovering the variant endoglucanase polypeptide.

The host cells are cultivated in a nutrient medium suitable for production of the variant endoglucanase polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the variant endoglucanase polypeptide is secreted into the nutrient medium, the variant endoglucanase polypeptide can be recovered directly from the medium. If the variant is not secreted, it can be recovered from cell lysates.

The variant endoglucanase polypeptide can be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant endoglucanase polypeptide.

The variant endoglucanase polypeptide can be recovered using methods known in the art. For example, the variant endoglucanase polypeptide can be recovered from the nutrient medium by conventional procedures including, but not limited to, collection, centrifugation, filtration, extraction, spray-drying, evaporation, or precipitation.

The variant can be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

H. Methods of Using Variant Endoglucanases

The endoglucanases of the present invention possess valuable properties allowing for a variety of industrial applications, such as, in textile, detergent, and pulp and paper industries. The novel (variant) endoglucanase enzymes of the invention have the advantage of being active at acid and neutral pH values, they have highly improved performance in textile biostoning and biofinishing applications and in detergent and other applications.

With the improved efficiency of the endoglucanases of the invention, the use of the enzymes is significantly more economical. Additional advantages are achieved also in terms of logistics and the storage of the enzyme products, when smaller amounts of the enzyme product are needed. Furthermore, the novel endoglucanases of the present invention, act more rapidly, affording time- and cost-effective treatment procedures and savings in equipment as well as treatment facilities.

In some embodiments, the dosage of the polypeptide composition of the invention and other conditions under which the composition is used may be determined on the basis of methods known in the art.

1. In Textile Industry

The (variant) endoglucanases of the invention have a wide range of textile applications. For example, fabrics or garments manufactured from denim, such as jeans, are one of the world's most popular clothing items. The "stonewash look" has been traditionally achieved by locally removing the indigo dye using a process in which pumice stone is added to the washing drum to abrade the garment. This traditional 'stone-washed' finish on denim fabric virtually damaged the machinery and caused pollution in waste water. The new environmental-friendly process, termed as biostoning, uses enzymes to wash/bio-stone denim, producing distressed appearance, without harming the machinery or the environment. The bio-stoning of denims has resulted in cost saving and improved quality and is used by many denim manufacturers (see Agrawal et al., Current Trends in Biomedical Engineering & Biosciences. 2017. 3(3):1-3, hereby incorporated by reference in its entirety).

The (variant) endoglucanases of the invention exhibit high efficiency in producing a "stonewash look" or an "abraded look" and to minimize backstaining in biostoning treatment of cellulose-containing textile materials, especially denim. In some embodiments, the present invention provides a method of biostoning comprising the step of contacting the (variant) endoglucanase enzyme(s) as described herein with cotton-containing fabrics or garments, such as denim.

In cotton fabric, fuzz (microfibers) emerges from the surface, which may entangle during processing, thus forming pills. Enzymes weaken the microfibers raising up from the surface and shear forces of the treatment then remove them (U.S. Pat. No. 7,256,032, hereby incorporated by reference in its entirety). The (variant) endoglucanases of the invention are especially useful in the textile industry for biofinishing of fabrics or garments, e.g., depilling, defuzzing, color clarification, harshness reduction, creation of different finishes (for example, a peach skin, worn out, sand washed, or antique look effect) and for biofinishing of yarn, for example, reduction of hairiness and improvement of smoothness and/or softness.

In some embodiments, the (variant) endoglucanases of the invention exhibit high efficiency in a biofinishing process to depill, defuzz or reduce harshness in a textile material. In some embodiments, the present invention provides a method of biofinishing comprising the step of contacting the (variant) endoglucanase enzyme(s) as described herein with a textile material, such as fabrics, garments, yarn, etc.

2. In Detergent Industry

Additional uses of the (variant) endoglucanases of the invention include their use in detergent compositions to improve fabric care properties by antipilling, antigraying, color clarification and softening, and to improve textile-cleaning effect, for instance soil removal. In some embodiments, the (variant) endoglucanases of the invention can be used to brighten colors and to prevent graying and pilling in detergent industry.

In some embodiments, the present invention provides a detergent composition comprising the (variant) endoglucanase enzymes as described herein. In additional embodiments, the present invention provides a detergent composition comprising the (variant) endoglucanase enzymes as described herein, and further comprising at least one surface active agent and optionally at least one auxiliary ingredient. Surface active agents include but not limited to anionic, non-ionic, cationic and ampholytic surfactants. Other auxiliary ingredients include but not limited to builders, anti-redeposition and soil suspension agents, optical brighteners, bleaching agents, dyes and pigments and hydrolases. A suitable listing of the contents of detergents is given in U.S. Pat. No. 5,433,750, hereby incorporated by reference in its entirety. A suitable list of surfactants is given in U.S. Pat. No. 3,664,961, hereby incorporated by reference in its entirety. Useful detergent compositions are described e.g. in WO94/07998, U.S. Pat. Nos. 5,443,750 and 3,664,961, which are all incorporated by reference in their entireties.

In some embodiments, the present invention provides a method of treating cellulosic fiber containing textile material(s) comprising contacting said textile material(s) with the detergent composition comprising the (variant) endoglucanase enzymes as described herein.

3. In Pulp and Paper Industries

In the pulp and paper industry, the (variant) endoglucanases of the invention can be used, for example, in deinking or modifying fiber of different recycled papers and paperboards having neutral or alkaline pH, in improving the fiber quality, or increasing the drainage in paper manufacture. Other examples of uses of the (variant) endoglucanases as described herein include the removal of printing paste thickener and excess dye after textile printing, and as a treatment for animal feed. For example, if the intended application is improvement of the strength of the mechanical pulp, then the (variant) endoglucanase enzymes of the invention may provide one or more of these proteins so as to enhance or facilitate the ability of cellulose fibers to bind together. In a similar manner, in the application of pulp refining, the (variant) endoglucanases of the invention may provide one or more of these proteins at a level that enhance or facilitate such swelling.

In some embodiments, the (variant) endoglucanase enzymes of the invention are used in deinking to release ink from fiber surfaces and in improving pulp drainage in the pulp and paper industry.

In some embodiments, the present invention provides a method for treating wood-derived pulp or fiber, comprising the step of contacting the (variant) endoglucanase enzymes as described herein with wood-derived mechanical or chemical pulp or secondary fiber.

VI. EXAMPLES

Example 1

Endoglucanase Gene Synthesis and Cloning 26 novel endoglucanases were selected based on bioinformatics analysis and were synthesized by GeneWiz (https://www.genewiz.com/en/). The synthesized genes were cloned into the pESC-URA vector (Agilent Technologies, Santa Clara, Calif., Catalogue #217454).

Example 2

Preparation of Endoglucanases Produced by *Saccharomyces cerevisiae* in Microtiter Plates The *Saccharomyces cerevisiae* INSCV1 strain (ThermoFisher Scientific, USA: Catalogue #V8251-20) containing recombinant endogluconase-encoding genes from single colonies were inoculated into individual wells of 96 well plates containing 300 µl synthetic minimal defined medium (SC) with 2% glucose and no uracil supplementation. The cultures were grown overnight at 30° C., 200 rpm and 85% humidity. Appropriate volume of overnight culture from each well needed to obtain an OD600 of 0.4 was added to corresponding wells of the new 96 well plates containing 350 µl of induction medium (SC selective medium containing 2% galactose). The plates were then incubated for 48 hrs at 30° C., 250 rpm and 85% humidity. The cells were then pelleted using centrifugation at 4000 rpm for 10 min at 4° C. The supernatants were transferred to round bottom plates and stored at −20° C. prior to activity assay. A total of 26 endoglucanase candidates were grown based on the procedure herein.

Example 3

CMC Assay to Evaluate *Saccharomyces cerevisiae* Produced Endoglucanases Activity Into PCR plate, add 50 µL of 1.8% low viscosity CMC dissolved in 100 mM sodium acetate, pH5.5 buffer (Catalog

C5678). Into the same PCR plate, add 10 µL of supernatant enzyme and shake on bench top shaker for ~1 minute. Incubate plates at 50° C. for 30 minutes. After 30 minutes, centrifuge plate at 4,000 rpm for 2 minutes. Into the plate add 90 µL of DNS solution and seal the plates. Place the plate into Thermocycler and select "95DNS" program with NO heated lid option. "95DNS" program settings: at 95° C. for 5 minutes and cool to 4° C. for 2 minutes. After incubation, overturn plates a few times and centrifuge plates for 3 minutes at 4,000 rpm. Into clear bottom plates, add 100 µL of water and transfer 100 µL of DNS reaction. Shake the plates and read plates at 540 nm for activity. A total of 25 endoglucanase candidates were evaluated based on the procedure herein and the results are shown in FIG. 1.

One novel endoglucanase, CL00066590 from *Aspergillus lentulus* (Assession number A0A0S7DSS1, noted as EG185), was identified with high activity and was chosen for further improvement. An additional endoglucanase, CL00078795 from *Aspergillus udagawae* (Assession number A0A0K8LET0, noted as EG140), was also chosen for further improvement based on its close % sequence identity to CL00066590. Sequence alignment of the EG140 and EG185 is shown in FIG. 2. EG140 and EG185 are 90% identical to each other.

Example 4

EG140 and EG185 Variant Collection Design and Construction

The starting wildetype endoglucanases EG140 and EG185 were used as the parents (G1P) of Generation 1 improvement. The best EG140 G1 variant was used as the parent (G2P) of Generation 2 improvement. The best EG140 G2 variant was used as the parent (G3P) of Generation 3 improvement. To improve endoglucanases' activity and stability at biostoning relevant conditions such as 50° C., pH6.5, multiple variant collections were designed for EG140 Generations 1-3 improvement and EG185 Generation 1 improvement based on protein sequences, computational models and mutation profiles determined experimentally. The design includes one to multiple specific mutations per variant. The variant collections were constructed using standard site-directed mutagenesis methods and subsequently cloned into the pESC-URA vector (Agilent Technologies, Santa Clara, Calif., Catalogue #217454).

Example 5

Preparation of EG140 and EG185 Variants Produced by *Saccharomyces cerevisiaein* in Microtiter Plates The *Saccharomyces cerevisiae* INSCV1 strain (ThermoFisher Scientific, USA: Catalogue #V8251-20) containing recombinant endogluconase-encoding genes from single colonies were inoculated into individual wells of 96 well plates containing 300 µl synthetic minimal defined medium (SC) with 2% glucose and no uracil supplementation. The cultures were grown overnight at 30° C., 200 rpm and 85% humidity. Appropriate volume of overnight culture from each well needed to obtain an OD600 of 0.4 was added to corresponding wells of the new 96 well plates containing 350 µl of induction medium (SC selective medium containing 2% galactose). The plates were then incubated for 48 hrs at 30° C., 250 rpm and 85% humidity. The cells were then pelleted using centrifugation at 4000 rpm for 10 min at 4° C. The supernatants were transferred to round bottom plates and stored at −20° C. prior to HTP screening.

Example 6

HTP Screening of EG140 Variants at 50° C., pH4.5 and pH6.5

All EG140 variants were screened under the following conditions. Dilute supernatants to 3× using 100 mM sodium acetate, pH4.5 or 100 mM phosphate buffer, pH6.5. Into PCR plate, add 50 µL of 1.6% low viscosity CMC (Catalog #C5678). Into the same PCR plate, add 10 µL diluted supernatant enzyme and shake on bench top shaker for ~1 minute. Incubate plates at 50° C. for 3 hours. After 3-hours, centrifuge plate at 4,000 rpm for 2 minutes. Into the plate add 90 µL of DNS solution and seal the plates. Place the plate into Thermocycler and select "95DNS" program with NO heated lid option. "95DNS" program settings: at 95° C. for 5 minutes and cool to 4° C. for 2 minutes. After incubation, overturn plates a few times and centrifuge plates for 3 minutes at 4,000 rpm. Into clear bottom plates, add 100 µL of water and transfer 100 µL of DNS reaction. Shake the plates and read plates at 540 nm for activity.

G1, G2 and G3 variants identified with improved total activity and tolerance to pH 6.5 are shown in FIGS. 3, 4 and 5, respectively.

Example 7

HTP Screening of EG185 Variants at 50° C., pH4.5 and pH6.5

All EG185 variants were screened under the following conditions for tier 1 assay. Dilute supernatants to 3× using 100 mM sodium acetate, pH4.5 or 100 mM phosphate buffer, pH6.5. Into PCR plate, add 50 µL of 1.6% low viscosity CMC (Catalog #C5678). Into the same PCR plate, add 10 µL diluted supernatant enzyme and shake on bench top shaker for ~1 minute. Incubate plates at 50° C. for 3 hours. After 3-hours, centrifuge plate at 4,000 rpm for 2 minutes. Into the plate add 90 µL of DNS solution and seal the plates. Place the plate into Thermocycler and select "95DNS" program with NO heated lid option. "95DNS" program settings: at 95° C. for 5 minutes and cool to 4° C. for 2 minutes. After incubation, overturn plates a few times and centrifuge plates for 3 minutes at 4,000 rpm. Into clear bottom plates, add 100 µL of water and transfer 100 µL of DNS reaction. Shake the plates and read plates at 540 nm for activity.

G1 variants identified with improved total activity and tolerance to pH 6.5 are shown in FIG. 6.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only.

What is claimed:

1. A composition comprising a variant endoglucanase enzyme comprising an amino acid substitution at position number 25 as compared to SEQ ID NO:1 and at least one further amino acid substitution as compared to SEQ ID NO:1, wherein said further amino acid substitution is at a position number selected from the group consisting of 12, 40, 44, 65, 138, 139, 160, 161, 171, 172, 175, 182, 184, 194, 212, 214, 55, 80, 86, 104, 126, 128, 136, 145, 152, 164, 165, 169, 173, 176, 179, 181, 187, 205, 207 and 218, and wherein said variant enzyme has endoglucanase activity and is at least 95% identical to SEQ ID NO:1.

2. The composition according to claim 1, wherein said variant endoglucanase enzyme exhibits at least 96%, 97%, 98%, or 99% identity to SEQ ID NO:1.

3. The composition according to claim 1, wherein said amino acid substitution(s) occur at one of said positions, two of said positions, three of said positions, four of said positions, five of said positions, six of said positions, seven of said positions, eight of said positions, nine of said positions, or ten of said positions.

4. The composition according to claim 1, wherein said further amino acid substitution is selected from the group consisting of N12S, N40S, A44S, Q65G, N138T, I139V, S160A, A161G, V171I, M172K, W175F, H182Q, Y184F, M194L, K212N, T214S, N12D, N12E, N12G, N12T, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, K212E and N218S.

5. A composition comprising a variant endoglucanase enzyme comprising at least one amino acid substitution as compared to SEQ ID NO:1, wherein said variant enzyme has endoglucanase activity and is at least 90% identical to SEQ ID NO:1 and said amino acid substitutions are selected from the group consisting of G25D/A161G/M172K/H182Q/M194L/K212N, N12S/G25D/Q65G/S160A/A161G/V171I/Y184F/M194L/K212N, G25D/N138T/V171I/W175F/H182Q/Y184F, G25D/N138T/I139V/M194L, G25D/A161G/T214S, N12S/G25D/A161G/H182Q/Y184F/M194L/K212N/T214S, G25D/N138T/H182Q/K212N, N12S/G25D/A44S/I139V, G25D/N138T/K212N, G25D/V171I/W175F/M194L/K212N, G25D/A161G/K212N, G25D/A44S/A161G, G25D/M172K/H182Q, G25D/A44S/V171I/M172K/H182Q/K212N, G25D/V171I/M172K/H182Q/M194L, G25D/K212N, N12S/G25D/N138T/A161G/K212N, G25D/H182Q/Y184F/M194L/K212N, N12S/G25D/N40S/I139V/V171I/M172K/H182Q/Y184F/M194L/K212N/T214S, N12S/G25D/H182Q/K212N, G25D/N40S/A44S/N138T/A161G/V171I/W175F/Y184F/M194L/K212N, N12S/G25D/A44S/Q65G, G25D/A161G/M194L/T214S, G25D/Y184F/M194L/K212N, N12S/G25D/D55P/V171I/M172K/S187P, G25D/S187P, G13P/G25D/D55P/A161P/S187P/R205P/K212N, G25D/D55P, N12S/G25D, G13P/G25D/D55P/V171I/S187P/R205P, G13P/G25D/V171I/M172K/S187P/R205P/K212N, G25D/D55P/R205P, G25D/V171I/M172K, G25D/R133P, N12S/G25D/V171I/M172K, N12S/G25D/H182Q/R205P, N12S/G25D/A161P/S187P/K212N, G25D/D55P/V171I/M172K/R205P, N12S/G25D/T69P/R133P/V171I/M172K/R205P/K212N, T179Y/R205Y, N12E/G25D/D55I/G126V/T136M/T165D/R205P, N12E/G25D/D55I/G126S/T136Y/R205P/T207E/N218S, N12E/G25S/D55P/N181S/R205P, N12E/G25D/D55I/P80G/G126I/T136M/R205P, N12E/G25D/D55P/G126K/E145A/T165D/R205P, N12E/G25D/D55I/G126T/T136M/T165Y/T179L/R205P, N12E/G25S/D55P/P80G/G126T/T136Y/T165Y/R205P/T207E, N12E/G25S/D55P/G126T/R205P/T207E, N12E/G25D/D55P/G126N/T136Y/T165Y/T179Y/N181S/R205P/T207E, N12E/G25S/D55P/P80G/G126R/T136Y/R205P, G25D/D55P/G126T/T165Y/R205P, N12E/G25S/D55I/G126K/T165D/R205P, N12E/G25S/D55P/G126I/T136Y/R205P, G25D/D55P/G126K/T136Y/T179Y/N181S/R205P, N12E/G25D/D55I/G126R/R205P, N12E/G25S/D55P/G126N/R205P/T207E, N12E/G25D/D55P/P80G/E145A/R205P/T207E, G25D/D55P/T136Y/T165Y/R205P/T207E, N12E/G25S/D55P/G126R/T136Y/T165Y/R205P, N12E/G25D/D55P/P80G/R205P, G25D/D55I/G126K/R205Y, N12E/G25S/D55P/G126R/R205P/T207E, G25D/D55P/G126T/T136Y/T165Y/R205P/N218S, N12E/G25D/D55P/G126N/R205P, N12E/G25D/D55P/G126K/R205P, N12E/G25D/D55P/T165D/R205Y, N12E/G25D/D55I/P80G/G126R/R205P/T207E, N12E/G25S/D55P/G126K/T165D/R205P, G25D/D55P/
G126V/T136Y/R205P/T207E, G25D/D55P/T179L/N181S/
R205P/T207E, N12E/G25S/D55P/T165Y/R205P/N218S,
N12E/G25D/D55I/G126V/T136M/R205P/N218S, G25S/
D55P/G126R/T136M/E145A/R205P, N12E/G25D/D55I/
G126T/T136M/R205Y, N12E/G25S/D55P/G126V/E145A/
T179Y/R205P, N12E/G25S/D55P/G126T/T165Y/R205P,
G25S/D55P/G126R/R205P/N218S, N12E/G25S/D55P/
G126T/T136Y/R205P/T207E, N12E/G25S/D55I/G126R/
T136M/T165Y/R205P/T207E/N218S, N12E/G25S/D55P/
G126S/T136M/T165Y/R205Y, N12D/G25D/D55P/S86A/
E145M/I164T/D173P/R205P/T207E, N12E/G25D/A44D/
D55P/S86H/Q128F/R205P, G25S/D55P/G126I/D173N/
R205P/T207E, N12D/G25S/A44D/D55P/S86Q/T152Q/
R176H/S187N/R205P/K212E, N12D/G25D/A44D/D55P/
Q128R/E145A/D173E/R205P, N12D/G25D/A44D/D55P/
S86A/E145A/R205P/T207E, N12D/G25S/D55P/T136Y/
G169T/R176H/R205P/K212E, N12E/G25D/D55P/S86Q/
A104D/G126T/E145A/D173E/R205P/K212E, G25D/
A44D/D55P/I164T/R205P, N12T/G25D/D55P/S86A/
A104D/Q128R/T165Y/R176H/R205P/K212E/N218S,
N12D/G25D/D55P/P80G/S86A/Q128R/I164T/D173E/
R205P/K212E, N12D/G25S/D55P/Q128R/T165Y/R176H/
R205P/K212E, N12G/G25D/A44D/D55P/Q128R/I164T/
D173E/R205P, N12T/G25D/D55P/G126K/E145A/T165D/
D173E/R205P, G25D/A44D/D55P/Q128R/R205P/T207E,
G25S/D55P/G126S/T165D/G169S/T179Y/R205P/K212E,
G25S/A44D/D55P/P80G/S86A/G126K/Q128R/R205P/
K212E, G25S/D55P/P80G/G126T/R205P, N12T/G25D/
D55I/P80G/G126S/T152Q/S187N/R205P, G25S/D55P/
G126K/T136R/T152Q/R176H/T179Y/R205P/K212E,
G25D/D55P/G126T/T165Y/R176H/R205P, N12D/G25D/
D55P/S86Q/A104D/E145A/R205P/T207E/N218S, G25D/
A44D/D55P/A104D/Q128R/E145A/T165D/R176H/
R205P/K212E, G25D/D55P/R205P/K212N, N12E/G25S/
D55R/G126T/T136Y/R205P/T207E, N12E/V17I/G25S/
D55P/G126T/T136Y/R205P/T207E, N12E/G25S/V35I/
D55P/G126T/T136Y/R205P/T207E, N12E/G25S/D55P/
G126T/V127I/T136Y/R205P/T207E, N12E/G25S/G42S/
D55P/G126T/T136Y/R205P/T207E, N12E/G25S/D55P/
Y124F/G126T/T136Y/R205P/T207E, N12E/G25S/D55P/
S78T/G126T/T136Y/R205P/T207E, N12D/G25D/A44D/
D55P/S86Q/G126T/T136Y/R176H/S187N/R205P/T207E,
N12T/G25D/D55P/G126T/T136Y/S187N/R205P/T207E/
K212E, N12D/G25D/D55P/G126T/T136Y/R205P/T207E,
N12D/G25D/D55P/S86Q/G126T/T136Y/R205P/T207E,
N12D/G25S/D55P/S86Q/G126T/T136Y/T165Y/S187N/
R205P/T207E/K212E, N12E/G25S/S28N/D55P/G126T/
T136Y/R205P/T207E, N12E/G25S/S39Y/D55P/G126T/
T136Y/R205P/T207E, N12E/G25S/D55P/G126T/T136Y/
R205P/T207E/K212N, N12T/G25S/A44D/D55P/S86Q/
G126N/T136M/R176H/S187N/R205P/T207E/K212E,
N12E/G25D/D55P/G126T/T136Y/S187N/R205P/T207E/
K212E, N12D/G25D/D55P/G126T/T136M/S187N/R205P/
T207E, N12D/G25D/D55P/A104D/G126T/T136Y/S187N/
R205P/T207E/K212E, N12T/G25D/D55P/S86Q/G126T/
T136M/R176H/S187N/R205P/T207E/K212E, N12D/
G25S/A44D/D55P/S86Q/A104D/G126T/T136Y/R205P/
T207E, N12E/G25D/D55P/S86Q/G126T/T136M/D173L/
R176H/R205P/T207E, N12D/G25D/D55P/G126T/T136Y/
R205P/T207E/K212E, N12D/G25D/A44D/D55P/G126T/
T136Y/S187N/R205P/T207E/K212E, N12E/G25D/A44D/
D55P/G126S/T136Y/S187N/R205P/T207E, N12D/G25D/
A44D/D55P/G126T/T136Y/S187N/R205P/T207E, and
N12D/G25D/A44D/D55P/S86Q/G126K/T136Y/D173E/
R176H/S187N/R205P/T207E.

6. The composition according to claim 1, wherein said endoglucanase enzyme has at least 95% sequence identity to an amino acid sequence selected from the group consisting of SEQ ID NO:3, SEQ ID NO:5, SEQ ID NO:7, SEQ ID NO:19, SEQ ID NO:21, and SEQ ID NO:23.

7. The composition according to claim 1, wherein said amino acid substitutions comprise G25D/A44S/V171I/M172K/H182Q/K212N.

8. The composition according to claim 1, wherein said amino acid substitutions comprise G25D/K212N.

9. The composition according to claim 1, wherein said amino acid substitutions comprise N12S/G25D/H182Q/K212N.

10. The composition according to claim 1, wherein said amino acid substitutions comprise G25D/D55P/R205P.

11. The composition according to claim 1, wherein said amino acid substitutions comprise N12E/G25S/D55P/G126T/T136Y/R205P/T207E.

12. The composition according to claim 1, wherein said amino acid substitutions comprise N12E/G25S/D55P/G126T/T136Y/R205P/T207E/K212N.

13. The composition according to claim 1 comprising amino acid substitutions G25D/A44S/V171I/M172K/H182Q/K212N, and further comprising at least one amino acid substitution selected from the group consisting of N12S, N40S, Q65G, N138T, I139V, S160A, A161G, W175F, Y184F, M194L, T214S, N12D, N12E, N12G, N12T, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

14. The composition according to claim 1 comprising amino acid substitutions G25D/K212N, and further comprising at least one amino acid substitution selected from the group consisting of N12S, N40S, A44S, Q65G, N138T, I139V, S160A, A161G, V171I, M172K, W175F, H182Q, Y184F, M194L, T214S, N12D, N12E, N12G, N12T, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

15. The composition according to claim 1 comprising amino acid substitutions N12S/G25D/H182Q/K212N, and further comprising at least one amino acid substitution selected from the group consisting of N40S, A44S, Q65G, N138T, I139V, S160A, A161G, V171I, M172K, W175F, Y184F, M194L, T214S, A44D, D55I, D55P, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, R205P, R205Y, T207E, and N218S.

16. The composition according to claim 1 comprising amino acid substitutions G25D/D55P/R205P, and further comprising at least one amino acid substitution selected from the group consisting of N12S, N40S, A44S, Q65G, N138T, I139V, S160A, A161G, V171I, M172K, W175F, H182Q, Y184F, M194L, K212N, T214S, N12D, N12E, N12G, N12T, A44D, P80G, S86A, S86H, S86Q, A104D, G126I, G126K, G126N, G126R, G126S, G126T, G126V, Q128F, Q128R, T136M, T136R, T136Y, E145A, E145M, T152Q, I164T, T165D, T165Y, G169S, G169T, D173E, D173N, D173P, R176H, T179L, T179Y, N181S, S187N, T207E, K212E, and N218S.

17. The composition according to claim 1 comprising amino acid substitutions N12E/G25S/D55P/G126T/T136Y/R205P/T207E, and further comprising at least one amino acid substitution selected from the group consisting of N40S, A44S, Q65G, N138T, I139V, S160A, A161G, V171I, M172K, W175F, H182Q, Y184F, M194L, K212N, T214S, A44D, P80G, S86A, S86H, S86Q, A104D, Q128F, Q128R, E145A, E145M, T152Q, I164T, T165D, T165Y, G169S, G169T, D173E, D173N, D173P, R176H, T179L, T179Y, N181S, S187N, K212E, and N218S.

18. The composition according to claim 1 comprising amino acid substitutions N12E/G25S/D55P/G126T/T136Y/R205P/T207E/K212N, and further comprising at least one amino acid substitution selected from the group consisting of N40S, A44S, Q65G, N138T, I139V, S160A, A161G, V171I, M172K, W175F, H182Q, Y184F, M194L, T214S, A44D, P80G, S86A, S86H, S86Q, A104D, Q128F, Q128R, E145A, E145M, T152Q, I164T, T165D, T165Y, G169S, G169T, D173E, D173N, D173P, R176H, T179L, T179Y, N181S, S187N, and N218S.

* * * * *